(12) United States Patent
Schabbauer et al.

(10) Patent No.: US 9,867,875 B2
(45) Date of Patent: *Jan. 16, 2018

(54) METHODS AND COMPOSITIONS FOR MODULATING THE IMMUNE SYSTEM WITH ARGINASE I

(71) Applicant: Bio-Cancer Treatment International Limited, Shatin (HK)

(72) Inventors: Gernot Schabbauer, Vienna (AT); Stephen Bluml, Vienna (AT); Emine Sahin-Heco, Vienna (AT); Paul Cheng, Shatin (HK); Li Chen, Shatin (HK)

(73) Assignee: BIO-CANCER TREATMENT INTERNATIONAL LIMITED, Shatin (HK)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,264

(22) Filed: May 18, 2016

(65) Prior Publication Data

US 2016/0367648 A1 Dec. 22, 2016

Related U.S. Application Data

(63) Continuation of application No. 14/697,835, filed on Apr. 28, 2015.

(60) Provisional application No. 61/985,924, filed on Apr. 29, 2014.

(51) Int. Cl.
| | |
|---|---|
| *A61K 38/50* | (2006.01) |
| *C12N 9/78* | (2006.01) |
| *A61K 9/00* | (2006.01) |
| *A61K 47/48* | (2006.01) |

(52) U.S. Cl.
CPC ............ *A61K 38/50* (2013.01); *A61K 9/0019* (2013.01); *A61K 47/48215* (2013.01); *C12N 9/78* (2013.01); *C12Y 305/03001* (2013.01)

(58) Field of Classification Search
None
See application file for complete search history.

(56) References Cited

U.S. PATENT DOCUMENTS

| | | | | |
|---|---|---|---|---|
| 7,951,366 B2 * | 5/2011 | Cheng | ............... | C12N 9/78 424/94.6 |
| 2004/0234517 A1 * | 11/2004 | Bowman | ............... | C12N 15/113 424/94.63 |
| 2008/0248018 A1 | 10/2008 | Cheng et al. | | |
| 2009/0047268 A1 | 2/2009 | Kakkis et al. | | |
| 2013/0295073 A1 | 11/2013 | Cheng | | |
| 2014/0112902 A1 | 4/2014 | Foster et al. | | |
| 2015/0315561 A1 | 11/2015 | Schabbauer et al. | | |

FOREIGN PATENT DOCUMENTS

| | | |
|---|---|---|
| AU | 2003250371 A1 | 1/2004 |
| CN | 1918298 A | 2/2007 |
| CN | 101357986 A | 2/2009 |
| CN | 103184208 A | 7/2013 |
| CN | 103184209 A | 7/2013 |
| CN | 103402537 A | 11/2013 |
| EP | 1517699 A1 | 3/2005 |
| EP | 1908478 A1 | 4/2008 |
| EP | 2654776 A1 | 10/2013 |
| IL | 165858 A | 12/2010 |
| JP | 2013172743 A | 9/2013 |
| JP | 5307042 B2 | 10/2013 |
| NZ | 537774 A | 1/2007 |
| WO | WO 2013/097658 * | 7/2013 |
| WO | WO-2013097568 A1 | 7/2013 |
| WO | WO-2013097657 A1 | 7/2013 |
| WO | WO-2014001956 A2 | 1/2014 |

OTHER PUBLICATIONS

Munder, et al. 2006. Suppression of T-cell functions by human granulocyte arginase. Blood 108: 1627-1634.*
Rotondo, et al. 2011. Exocytosis of azurophil and arginase 1-containing granules by activated polymorphonuclear neutrophils is required to inhibit T lymphocyte proliferation. J. Leukoc. Biol. 89: 721-727.*
Pesce, et al. 2009. Arginase-1-expressing macrophages suppress Th2 cytokine-driven inflammation and fibrosis. PLoS Pathog. 5: e1000371.*
Peranzoni, et al. 2007. Role of arginine metabolism in immunity and immunopathology. Immunobiology 212: 795-812.*
Phillips et al., "Aberrant Reactive Oxygen and Nitrogen Species Generation in Rheumatoid Arthritis (RA): Causes and Consequences for Immune Function, Cell Survival, and Therapeutic Intervention", Antioxidants & Redox Signaling, 2010, vol. 12, No. 6, pp. 743-785. DOI: 10.1089=ars.2009.2607.*
Aksoy, et al. 2012. The p110delta isoform of the kinase PI(3)K controls the subcellular compartmentalization of TLR4 signaling and protects from endotoxic shock. Nat. Immunol. 13: 1045-1054.
Ansel, et al. Pharmaceutical Dosage Forms and Drug Delivery Systems. Seventh Edition, Lippincott Williams & Wilkins, 1999.
Bansal, et al., Arginine availability, arginase, and the immune response, Curr. Opin. Clin. Nutr. Metab. Care, Mar. 31, 2003 6(2):223-228.
Barron, et al. 2013. Role of arginase 1 from myeloid cells in th2-dominated lung inflammation. PLoS One 8: e61961.
Baumann, et al. 2005. Glucocorticoids inhibit activation-induced cell death (AICD) via direct DNA-dependent repression of the CD95 ligand gene by a glucocorticoid receptor dimer. Blood 106: 617-625.

(Continued)

*Primary Examiner* — Suzanne M Noakes
(74) *Attorney, Agent, or Firm* — Wilson Sonsini Goodrich & Rosati

(57) ABSTRACT

Methods and compositions comprising recombinant Arginase I proteins which are capable of depleting the plasma arginine levels in a subject are disclosed. The methods and compositions can be used to modulate the activity of the immune system in a subject. Modulation of the immune system is useful in the treatment of immune disorders and in preventing rejection of a transplanted organ, tissue, or cell. The methods and compositions can also be used to treat a bone condition of a subject.

30 Claims, 33 Drawing Sheets

(56) References Cited

OTHER PUBLICATIONS

Biswas, et al. 2010. Macrophage plasticity and interaction with lymphocyte subsets: cancer as a paradigm. Nat. Immunol. 11: 889-896.
Chaurasia, et al. 2010. Phosphoinositide-dependent kinase 1 provides negative feedback inhibition to Toll-like receptor-mediated NF-kappaB activation in macrophages. Mol. Cell Biol. 30: 4354-4366.
Cheng, et al. 2007. Pegylated recombinant human arginase (rhArg-peg5,000mw) inhibits the in vitro and in vivo proliferation of human hepatocellular carcinoma through arginine depletion. Cancer Res. 67: 309-317.
Clausen, et al. 1999. Conditional gene targeting in macrophages and granulocytes using LysMcre mice. Transgenic Res. 8: 265-277.
Corraliza, et al. Increased expression of arginase II in patients with different forms of arthritis. Implications of the regulation of nitric oxide. The Journal of rheumatology 29.11 (2002): 2261-2265.
Domingues, et al. 2010. Functional and pathogenic differences of Th1 and Th17 cells in experimental autoimmune encephalomyelitis. PLoS One 5: e15531.
El Kasmi, et al. 2008. Toll-like receptor-induced arginase 1 in macrophages thwarts effective immunity against intracellular pathogens. Nat. Immunol. 9: 1399-1406.
Engelman, et al. 2006. The evolution of phosphatidylinositol 3-kinases as regulators of growth and metabolism. Nat. Rev. Genet. 7: 606-619.
Ferguson, et al. 2007. PI(3)Kgamma has an important context-dependent role in neutrophil chemokinesis. Nat. Cell Biol. 9: 86-91.
Fukao, et al. 2003. PI3K and negative regulation of TLR signaling. Trends Immunol. 24: 358-363.
Gennaro, et al. Remington: The Science and Practice of Pharmacy. Nineteenth Edition, Mack Publishing Company, 1995.
Gordon, et al. 2010. Alternative activation of macrophages: mechanism and functions. Immunity 32: 593-604.
Guha, et al. 2002. The phosphatidylinositol 3-kinase-Akt pathway limits lipopolysaccharide activation of signaling pathways and expression of inflammatory mediators in human monocytic cells. J. Biol. Chem. 277: 32124-32132.
Gunzl, et al. 2010. Anti-inflammatory properties of the PI3K pathway are mediated by IL-10/DUSP regulation. J. Leukoc. Biol. 88: 1259-1269.
Hasko, et al. 2000. Spermine differentially regulates the production of interleukin-12 p40 and interleukin-10 and suppresses the release of the T helper 1 cytokine interferon-gamma. Shock 14: 144-149.
Heit, et al. 2008. PTEN functions to 'prioritize' chemotactic cues and prevent 'distraction' in migrating neutrophils. Nat. Immunol. 9: 743-752.
Hermeling, et al. Structure-Immunogenicity Relationships of Therapeutic Proteins. Pharmaceutical Research, vol. 21, No. 6, Jun. 2004.
Highfill, et al. 2010. Bone marrow myeloid-derived suppressor cells (MDSCs) inhibit graft-versus-host disease (GVHD) via an arginase-1-dependent mechanism that is up-regulated by interleukin-13. Blood 116: 5738-5747.
Holden, et al. Chorismate lyase: kinetics and engineering for stability. Biochim Biophys Acta. Jan. 31, 2002; 1594(1):160-7.
Hoover, J. Remington's Pharmaceutical Sciences. Mack Publishing Co., Seventeenth Edition, 1985.
International search report and written opinion dated Aug. 3, 2015 for PCT Application No. CN2015077654.
Lassmann, et al. 2011. The molecular basis of neurodegeneration in multiple sclerosis. FEBS Lett. 585: 3715-3723.
Liberman, et al. Pharmaceutical Dosage Forms. Marcel Decker, New York, 1980.
Luyendyk, et al. 2008. Genetic analysis of the role of the PI3K-Akt pathway in lipopolysaccharide-induced cytokine and tissue factor gene expression in monocytes/macrophages. J. Immunol. 180: 4218-4226.
Makarenkova, et al. 2006. CD11b+/Gr-1+ myeloid suppressor cells cause T cell dysfunction after traumatic stress. J. Immunol. 176: 2085-2094.
Martin, et al. 2005. Toll-like receptor-mediated cytokine production is differentially regulated by glycogen synthase kinase 3. Nat. Immunol. 6: 777-784.
Munder, et al. 1999. Th1/Th2-regulated expression of arginase isoforms in murine macrophages and dendritic cells. J. Immunol. 163: 3771-3777.
Munder, et al. 2005. Arginase I is constitutively expressed in human granulocytes and participates in fungicidal activity. Blood 105: 2549-2556.
Munder, M. 2009. Arginase: an emerging key player in the mammalian immune system. Br. J. Pharmacol. 158: 638-651.
Pauleau, et al. 2004. Enhancer-mediated control of macrophage-specific arginase I expression. J. Immunol. 172: 7565-7573.
Rath, et al. Metabolism via Arginase or Nitric Oxide Synthase: Two Competing Arginine Pathways in Macrophages. Front Immunol. 2014; 5: 532. Published online Oct. 27, 2014. Prepublished online Oct. 7, 2014. doi: 10.3389/fimmu.2014.00532.
Rauh, et al. 2005. SHIP represses the generation of alternatively activated macrophages. Immunity 23: 361-374.
Rosenberg, A. Effects of Protein Aggregates: An Immunologic Perspective. The AAPS Journal 2006; 8(3) Article 59.
Ruffell, et al. 2009. A CREB-C/EBPbeta cascade induces M2 macrophage-specific gene expression and promotes muscle injury repair. Proc. Natl. Acad. Sci. U. S A 106: 17475-17480.
Rutschman, et al. 2001. Cutting edge: Stat6-dependent substrate depletion regulates nitric oxide production. J. Immunol. 166: 2173-2177.
Schabbauer, et al. 2004. PI3K-Akt pathway suppresses coagulation and inflammation in endotoxemic mice. Arterioscler. Thromb. Vasc. Biol. 24: 1963-1969.
Schabbauer, et al. 2010. Myeloid PTEN promotes inflammation but impairs bactericidal activities during murine pneumococcal pneumonia. J. Immunol. 185: 468-476.
Srdjan, et al., Modulation of nitric oxide synthase by arginase and methylated arginines during the acute phase of experimental multiple sclerosis, J. Neurological Sciences, 2012, 318:106-111.
Srdjan et al., The Importance of Nitric Oxide and Arginase in the Pathogenesis of Acute Neuroinflammation: Are Those Contra Players with the Same Direction, Neurotoxicity Research, Apr. 24, 2014, 26:392-399.
Suzuki, et al. 2001. T cell-specific loss of Pten leads to defects in central and peripheral tolerance. Immunity 14: 523-534.
Wang, et al. 2011. Convergence of the mammalian target of rapamycin complex 1- and glycogen synthase kinase 3-beta-signaling pathways regulates the innate inflammatory response. J. Immunol. 186: 5217-5226.
Zhang, et al. 1997. Spermine inhibits proinflammatory cytokine synthesis in human mononuclear cells: a counterregulatory mechanism that restrains the immune response. J. Exp. Med. 185: 1759-1768.
Gaffen, et al., Role of IL-17 in the Pathogenesis of Rheumatoid Arthritis, Curr Rheumatol Rep. Oct. 2009, 11(5): 365-370.
Notice of allowance dated Aug. 7, 2017 for U.S. Appl. No. 14/697,835.
Office action dated Jan. 20, 2017 for U.S. Appl. No. 14/697,835.

* cited by examiner

FIGURE 2, PANEL A

FIGURE 2, PANEL B

FIGURE 2, PANEL C

FIGURE 2, PANEL D

FIGURE 2, PANEL E

FIGURE 2, PANEL F

FIGURE 2, PANEL G    FIGURE 2, PANEL H    FIGURE 2, PANEL I

FIGURE 2, PANEL J    FIGURE 2, PANEL K

FIGURE 6, PANEL A

FIGURE 6, PANEL B

FIGURE 6, PANEL C

FIGURE 6, PANEL D

FIGURE 6, PANEL E

FIGURE 6, PANEL F

FIGURE 6, PANEL G

FIGURE 12, PANEL A

FIGURE 12, PANEL B

FIGURE 12, PANEL C

FIGURE 12, PANEL D

FIGURE 13, PANEL A

FIGURE 13, PANEL B

FIGURE 13, PANEL C

FIGURE 13, PANEL D

FIGURE 13, PANEL E

FIGURE 13, PANEL F

Panel A

Panel B

SEQUENCE LISTING

```
<160> NUMBER OF SEQ ID NOS: 32

<210> SEQ ID NO 1
<211> LENGTH: 322
<212> TYPE: PRT
<213> ORGANISM: Homo sapiens

<400> SEQUENCE: 1

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300
```

Gly Leu Ala Arg Glu Gly Asn His Lys Pro Ile Asp Tyr Leu Asn Pro
305                 310                 315                 320

Pro Lys

<210> SEQ ID NO 2
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Ala Phe
    290                 295                 300

Gly Leu Ala Arg Glu Gly Asn His Lys Pro Ile Asp Tyr Leu Asn Pro
305                 310                 315                 320

Pro Lys

-continued

```
<210> SEQ ID NO 3
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Ala Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys

<210> SEQ ID NO 4
<211> LENGTH: 322
<212> TYPE: PRT
<213> ORGANISM: Artificial Sequence
<220> FEATURE:
<223> OTHER INFORMATION: Description of Artificial Sequence: Synthetic
```

<400> SEQUENCE: 4

```
Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Ala Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys
```

<210> SEQ ID NO 5
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Ser Ala Lys Ser Arg Thr Ile Gly Ile Ile Gly Ala Pro Phe Ser
1               5                   10                  15
```

-continued

Lys Gly Gln Pro Arg Gly Gly Val Glu Glu Gly Pro Thr Val Leu Arg
                20                  25                  30

Lys Ala Gly Leu Leu Glu Lys Leu Lys Glu Gln Glu Cys Asp Val Lys
            35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Ala Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Ala Phe
    290                 295                 300

Gly Leu Ala Arg Glu Gly Asn His Lys Pro Ile Asp Tyr Leu Asn Pro
305                 310                 315                 320

Pro Lys

<210> SEQ ID NO 6
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
                20                  25                  30

Lys Ala Gly Leu Leu Glu Lys Leu Lys Glu Gln Glu Ala Asp Val Lys
            35                  40                  45

Asp Tyr Gly Asp Leu Pro Phe Ala Asp Ile Pro Asn Asp Ser Pro Phe
            50                   55                  60

Gln Ile Val Lys Asn Pro Arg Ser Val Gly Lys Ala Ser Glu Gln Leu
 65                  70                  75                  80

Ala Gly Lys Val Ala Glu Val Lys Lys Asn Gly Arg Ile Ser Leu Val
                 85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
            115                 120                 125

Ile Asn Thr Pro Leu Thr Thr Thr Ser Gly Asn Leu His Gly Gln Pro
130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
            195                 200                 205

Gly Lys Val Met Glu Glu Thr Leu Ser Tyr Leu Leu Gly Arg Lys Lys
210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
            275                 280                 285

Val Thr Arg Thr Val Asn Thr Ala Val Ala Ile Thr Leu Ala Ala Phe
290                 295                 300

Gly Leu Ala Arg Glu Gly Asn His Lys Pro Ile Asp Tyr Leu Asn Pro
305                 310                 315                 320

Pro Lys

<210> SEQ ID NO 7
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ser Ala Lys Ser Arg Thr Ile Gly Ile Ile Gly Ala Pro Phe Ser
 1               5                  10                  15

Lys Gly Gln Pro Arg Gly Gly Val Glu Glu Gly Pro Thr Val Leu Arg
                20                  25                  30

Lys Ala Gly Leu Leu Glu Lys Leu Lys Glu Gln Glu Ala Asp Val Lys
            35                  40                  45

Asp Tyr Gly Asp Leu Pro Phe Ala Asp Ile Pro Asn Asp Ser Pro Phe
            50                  55                  60

Gln Ile Val Lys Asn Pro Arg Ser Val Gly Lys Ala Ser Glu Gln Leu
 65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
130                 135                 140

Val Ser Phe Leu Leu Lys Glu Leu Lys Gly Lys Ile Pro Asp Val Pro
145                 150                 155                 160

Gly Phe Ser Trp Val Thr Pro Ala Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys

<210> SEQ ID NO 8
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Ala Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

-continued

```
Arg Val His Pro Asp Leu Gly Val Ile Trp Val Asp Ala His Thr Asp
        115                 120                 125
Ile Asn Thr Pro Leu Thr Thr Thr Ser Gly Asn Leu His Gly Gln Pro
130                 135                 140
Val Ser Phe Leu Leu Lys Glu Leu Lys Gly Lys Ile Pro Asp Val Pro
145                 150                 155                 160
Gly Phe Ser Trp Val Thr Pro Ala Ile Ser Ala Lys Asp Ile Val Tyr
                165                 170                 175
Ile Gly Leu Arg Asp Val Asp Pro Gly Glu His Tyr Ile Leu Lys Thr
            180                 185                 190
Leu Gly Ile Lys Tyr Phe Ser Met Thr Glu Val Asp Arg Leu Gly Ile
        195                 200                 205
Gly Lys Val Met Glu Glu Thr Leu Ser Tyr Leu Leu Gly Arg Lys Lys
    210                 215                 220
Arg Pro Ile His Leu Ser Phe Asp Val Asp Gly Leu Asp Pro Ser Phe
225                 230                 235                 240
Thr Pro Ala Thr Gly Thr Pro Val Val Gly Gly Leu Thr Tyr Arg Glu
                245                 250                 255
Gly Leu Tyr Ile Thr Glu Glu Ile Tyr Lys Thr Gly Leu Leu Ser Gly
            260                 265                 270
Leu Asp Ile Met Glu Val Asn Pro Ser Leu Gly Lys Thr Pro Glu Glu
        275                 280                 285
Val Thr Arg Thr Val Asn Thr Ala Val Ala Ile Thr Leu Ala Ala Phe
    290                 295                 300
Gly Leu Ala Arg Glu Gly Asn His Lys Pro Ile Asp Tyr Leu Asn Pro
305                 310                 315                 320
Pro Lys
```

<210> SEQ ID NO 9
<211> LENGTH: 329
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 9

```
Met His His His His His Met Ser Ala Lys Ser Arg Thr Ile Gly
1               5                   10                  15
Ile Ile Gly Ala Pro Phe Ser Lys Gly Gln Pro Arg Gly Gly Val Glu
            20                  25                  30
Glu Gly Pro Thr Val Leu Arg Lys Ala Gly Leu Leu Glu Lys Leu Lys
        35                  40                  45
Glu Gln Glu Cys Asp Val Lys Asp Tyr Gly Asp Leu Pro Phe Ala Asp
    50                  55                  60
Ile Pro Asn Asp Ser Pro Phe Gln Ile Val Lys Asn Pro Arg Ser Val
65                  70                  75                  80
Gly Lys Ala Ser Glu Gln Leu Ala Gly Lys Val Ala Glu Val Lys Lys
                85                  90                  95
Asn Gly Arg Ile Ser Leu Val Leu Gly Gly Asp His Ser Leu Ala Ile
            100                 105                 110
Gly Ser Ile Ser Gly His Ala Arg Val His Pro Asp Leu Gly Val Ile
        115                 120                 125
Trp Val Asp Ala His Thr Asp Ile Asn Thr Pro Leu Thr Thr Thr Ser
    130                 135                 140
```

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Cys Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205

Glu Val Asp Arg Leu Gly Ile Gly Lys Val Met Glu Glu Thr Leu Ser
    210                 215                 220

Tyr Leu Leu Gly Arg Lys Arg Pro Ile His Leu Ser Phe Asp Val
225                 230                 235                 240

Asp Gly Leu Asp Pro Ser Phe Thr Pro Ala Thr Gly Thr Pro Val Val
                245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
        275                 280                 285

Leu Gly Lys Thr Pro Glu Glu Val Thr Arg Thr Val Asn Thr Ala Val
    290                 295                 300

Ala Ile Thr Leu Ala Cys Phe Gly Leu Ala Arg Glu Gly Asn His Lys
305                 310                 315                 320

Pro Ile Asp Tyr Leu Asn Pro Pro Lys
                325

<210> SEQ ID NO 10
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met His His His His His Met Ser Ala Lys Ser Arg Thr Ile Gly
1               5                   10                  15

Ile Ile Gly Ala Pro Phe Ser Lys Gly Gln Pro Arg Gly Gly Val Glu
                20                  25                  30

Glu Gly Pro Thr Val Leu Arg Lys Ala Gly Leu Leu Glu Lys Leu Lys
            35                  40                  45

Glu Gln Glu Cys Asp Val Lys Asp Tyr Gly Asp Leu Pro Phe Ala Asp
    50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
        115                 120                 125

Trp Val Asp Ala His Thr Asp Ile Asn Thr Pro Leu Thr Thr Thr Ser
    130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Cys Ile

```
                     165                 170                 175
Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205

Glu Val Asp Arg Leu Gly Ile Gly Lys Val Met Glu Glu Thr Leu Ser
210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
            245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
            275                 280                 285

Leu Gly Lys Thr Pro Glu Glu Val Thr Arg Thr Val Asn Thr Ala Val
290                 295                 300

Ala Ile Thr Leu Ala Ala Phe Gly Leu Ala Arg Glu Gly Asn His Lys
305                 310                 315                 320

Pro Ile Asp Tyr Leu Asn Pro Pro Lys
            325

<210> SEQ ID NO 11
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met His His His His His Met Ser Ala Lys Ser Arg Thr Ile Gly
1               5                   10                  15

Ile Ile Gly Ala Pro Phe Ser Lys Gly Gln Pro Arg Gly Gly Val Glu
            20                  25                  30

Glu Gly Pro Thr Val Leu Arg Lys Ala Gly Leu Leu Glu Lys Leu Lys
        35                  40                  45

Glu Gln Glu Cys Asp Val Lys Asp Tyr Gly Asp Leu Pro Phe Ala Asp
50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
            85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
        115                 120                 125

Trp Val Asp Ala His Thr Asp Ile Asn Thr Pro Leu Thr Thr Thr Ser
130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Ala Ile
            165                 170                 175

Ser Ala Lys Asp Ile Val Tyr Ile Gly Leu Arg Asp Val Asp Pro Gly
            180                 185                 190
```

```
Glu His Tyr Ile Leu Lys Thr Leu Gly Ile Lys Tyr Phe Ser Met Thr
            195                 200                 205

Glu Val Asp Arg Leu Gly Ile Gly Lys Val Met Glu Glu Thr Leu Ser
210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
            245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
            275                 280                 285

Leu Gly Lys Thr Pro Glu Glu Val Thr Arg Thr Val Asn Thr Ala Val
290                 295                 300

Ala Ile Thr Leu Ala Cys Phe Gly Leu Ala Arg Glu Gly Asn His Lys
305                 310                 315                 320

Pro Ile Asp Tyr Leu Asn Pro Pro Lys
            325

<210> SEQ ID NO 12
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met His His His His His Met Ser Ala Lys Ser Arg Thr Ile Gly
1               5                   10                  15

Ile Ile Gly Ala Pro Phe Ser Lys Gly Gln Pro Arg Gly Gly Val Glu
                20                  25                  30

Glu Gly Pro Thr Val Leu Arg Lys Ala Gly Leu Leu Glu Lys Leu Lys
            35                  40                  45

Glu Gln Glu Ala Asp Val Lys Asp Tyr Gly Asp Leu Pro Phe Ala Asp
50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
            115                 120                 125

Trp Val Asp Ala His Thr Asp Ile Asn Thr Pro Leu Thr Thr Thr Ser
130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Cys Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
            195                 200                 205

Glu Val Asp Arg Leu Gly Ile Gly Lys Val Met Glu Glu Thr Leu Ser
210                 215                 220
```

```
Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
            245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
        275                 280                 285

Leu Gly Lys Thr Pro Glu Glu Val Thr Arg Thr Val Asn Thr Ala Val
    290                 295                 300

Ala Ile Thr Leu Ala Cys Phe Gly Leu Ala Arg Glu Gly Asn His Lys
305                 310                 315                 320

Pro Ile Asp Tyr Leu Asn Pro Pro Lys
                325
```

<210> SEQ ID NO 13
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met His His His His His Met Ser Ala Lys Ser Arg Thr Ile Gly
1               5                   10                  15

Ile Ile Gly Ala Pro Phe Ser Lys Gly Gln Pro Arg Gly Gly Val Glu
                20                  25                  30

Glu Gly Pro Thr Val Leu Arg Lys Ala Gly Leu Leu Glu Lys Leu Lys
            35                  40                  45

Glu Gln Glu Cys Asp Val Lys Asp Tyr Gly Asp Leu Pro Phe Ala Asp
    50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
    115                 120                 125

Trp Val Asp Ala His Thr Asp Ile Asn Thr Pro Leu Thr Thr Thr Ser
130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Ala Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
    195                 200                 205

Glu Val Asp Arg Leu Gly Ile Gly Lys Val Met Glu Glu Thr Leu Ser
    210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
```

```
            245                 250                 255
Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
        275                 280                 285

Leu Gly Lys Thr Pro Glu Glu Val Thr Arg Thr Val Asn Thr Ala Val
        290                 295                 300

Ala Ile Thr Leu Ala Ala Phe Gly Leu Ala Arg Glu Gly Asn His Lys
305                 310                 315                 320

Pro Ile Asp Tyr Leu Asn Pro Pro Lys
                325

<210> SEQ ID NO 14
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met His His His His His Met Ser Ala Lys Ser Arg Thr Ile Gly
1               5                   10                  15

Ile Ile Gly Ala Pro Phe Ser Lys Gly Gln Pro Arg Gly Gly Val Glu
                20                  25                  30

Glu Gly Pro Thr Val Leu Arg Lys Ala Gly Leu Leu Glu Lys Leu Lys
            35                  40                  45

Glu Gln Glu Ala Asp Val Lys Asp Tyr Gly Asp Leu Pro Phe Ala Asp
        50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
        115                 120                 125

Trp Val Asp Ala His Thr Asp Ile Asn Thr Pro Leu Thr Thr Thr Ser
130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Cys Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205

Glu Val Asp Arg Leu Gly Ile Gly Lys Val Met Glu Glu Thr Leu Ser
    210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
                245                 250                 255

Gly Gly Leu Thr Tyr Arg Glu Gly Leu Tyr Ile Thr Glu Glu Ile Tyr
            260                 265                 270
```

```
Lys Thr Gly Leu Leu Ser Gly Leu Asp Ile Met Glu Val Asn Pro Ser
            275                 280                 285

Leu Gly Lys Thr Pro Glu Glu Val Thr Arg Thr Val Asn Thr Ala Val
290                 295                 300

Ala Ile Thr Leu Ala Ala Phe Gly Leu Ala Arg Glu Gly Asn His Lys
305                 310                 315                 320

Pro Ile Asp Tyr Leu Asn Pro Pro Lys
                325

<210> SEQ ID NO 15
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met His His His His His Met Ser Ala Lys Ser Arg Thr Ile Gly
1               5                   10                  15

Ile Ile Gly Ala Pro Phe Ser Lys Gly Gln Pro Arg Gly Gly Val Glu
                20                  25                  30

Glu Gly Pro Thr Val Leu Arg Lys Ala Gly Leu Leu Glu Lys Leu Lys
            35                  40                  45

Glu Gln Glu Ala Asp Val Lys Asp Tyr Gly Asp Leu Pro Phe Ala Asp
50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
        115                 120                 125

Trp Val Asp Ala His Thr Asp Ile Asn Thr Pro Leu Thr Thr Thr Ser
130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Ala Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205

Glu Val Asp Arg Leu Gly Ile Gly Lys Val Met Glu Glu Thr Leu Ser
210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
                245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
        275                 280                 285

Leu Gly Lys Thr Pro Glu Glu Val Thr Arg Thr Val Asn Thr Ala Val
290                 295                 300
```

Ala Ile Thr Leu Ala Cys Phe Gly Leu Ala Arg Glu Gly Asn His Lys
305                 310                 315                 320

Pro Ile Asp Tyr Leu Asn Pro Pro Lys
                325

<210> SEQ ID NO 16
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met His His His His His Met Ser Ala Lys Ser Arg Thr Ile Gly
1               5                   10                  15

Ile Ile Gly Ala Pro Phe Ser Lys Gly Gln Pro Arg Gly Gly Val Glu
                20                  25                  30

Glu Gly Pro Thr Val Leu Arg Lys Ala Gly Leu Leu Glu Lys Leu Lys
            35                  40                  45

Glu Gln Glu Ala Asp Val Lys Asp Tyr Gly Asp Leu Pro Phe Ala Asp
50                  55                  60

Ile Pro Asn Asp Ser Pro Phe Gln Ile Val Lys Asn Pro Arg Ser Val
65                  70                  75                  80

Gly Lys Ala Ser Glu Gln Leu Ala Gly Lys Val Ala Glu Val Lys Lys
                85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
        115                 120                 125

Trp Val Asp Ala His Thr Asp Ile Asn Thr Pro Leu Thr Thr Thr Ser
130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Ala Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205

Glu Val Asp Arg Leu Gly Ile Gly Lys Val Met Glu Glu Thr Leu Ser
    210                 215                 220

Tyr Leu Leu Gly Arg Lys Lys Arg Pro Ile His Leu Ser Phe Asp Val
225                 230                 235                 240

Asp Gly Leu Asp Pro Ser Phe Thr Pro Ala Thr Gly Thr Pro Val Val
                245                 250                 255

Gly Gly Leu Thr Tyr Arg Glu Gly Leu Tyr Ile Thr Glu Glu Ile Tyr
            260                 265                 270

Lys Thr Gly Leu Leu Ser Gly Leu Asp Ile Met Glu Val Asn Pro Ser
        275                 280                 285

Leu Gly Lys Thr Pro Glu Glu Val Thr Arg Thr Val Asn Thr Ala Val
    290                 295                 300

Ala Ile Thr Leu Ala Ala Phe Gly Leu Ala Arg Glu Gly Asn His Lys
305                 310                 315                 320

Pro Ile Asp Tyr Leu Asn Pro Pro Lys

```
<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcctctact ccattcttcc c                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actcccacca atgaacaaac                                                20

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcgcgattat cttctatatc ttcag                                          25

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctcgaccag tttagttacc c                                              21

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tattagccaa tattagccaa tattagccaa tattagcca                           39

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tggctaatat tggctaatat tggctaatat tggctaata                           39
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acaccgccaa atttaactgc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtgaagaacc cacggtctgt                                              20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttctccagt gtagccatcc tt                                           22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctggattggc aagaagttcc                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccctccttct gctctgtgtc                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tacaccagtc cgtcccttct                                              20

```
<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctggttgtca ggggagtgtt                                                      20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tctgggtaca agatccctga a                                                    21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cccttctcat ctgcatctcc                                                      20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caaacttggt gtggatgtcg                                                      20
```

METHODS AND COMPOSITIONS FOR MODULATING THE IMMUNE SYSTEM WITH ARGINASE I

CROSS-REFERENCE

This application is a continuation of U.S. patent application Ser. No. 14/697,835, filed on Apr. 28, 2015, which claims the benefit of U.S. Provisional Patent Application Ser. No. 61/985,924, filed on Apr. 29, 2014, which is incorporated herein by reference in its entirety.

SEQUENCE LISTING

The instant application contains a Sequence Listing which has been submitted in ASCII format via EFS-Web and is hereby incorporated by reference in its entirety, Said ASCII copy, created on Jul. 16, 2015, is named 46106-701.201_SL/txt and is 50,705 bytes in size.

BACKGROUND OF THE INVENTION

The immune system functions to protect the body against harmful antigens, bacteria, viruses, toxins, blood or tissues from another person or species, and cancer cells. Immune system disorders can lead to hyperactivity or hypoactivity of the immune system. In cases of immune system hyperactivity, the body attacks and damages its own tissues. In cases of immune system hypoactivity, also known as immune deficiency, the body's ability to fight foreign antigens is diminished, which often leads to a greater vulnerability to infections.

The enzyme arginase metabolizes L-arginine to L-ornithine and urea. Besides its fundamental role in the hepatic urea cycle, arginase is expressed in some cells of the immune system of some mammals. However, it is unclear if interferences with L-arginine metabolism can be used to treat immune conditions. Importantly, several challenges exist in formulating exogenous Arginases as a therapeutic agent that is suitable for clinical administration.

SUMMARY OF THE INVENTION

In some embodiments, the invention provides a method of treating an inflammatory disease in a subject in need thereof, the method comprising administering to the subject a therapeutically-effective amount of a purified Arginase or a functional fragment thereof.

In some embodiments, the invention provides a method of modulating inflammation, the method comprising administering to a subject a therapeutically-effective amount of a purified Arginase, or a functional fragment thereof, wherein the administration modulates the inflammation.

In some embodiments, the purified Arginase is recombinant Arginase. In some embodiments, the recombinant Arginase is pegylated. In some embodiments, a functional fragment of the recombinant Arginase is pegylated. In some embodiments, the pegylated recombinant Arginase is recombinant human Arginase I, or a functional fragment thereof.

In some embodiments, the invention provides a method of modulating inflammation, the method comprising administering to a subject a therapeutically-effective amount of a purified pegylated recombinant human Arginase I, or a functional fragment thereof, wherein the administration modulates the inflammation.

In some embodiments, the invention provides a use of a purified recombinant arginase, or a functional fragment thereof, in the preparation of a medicament for treating an inflammatory disease in a subject.

In some embodiments, the invention provides a pharmaceutical composition comprising a purified pegylated recombinant human Arginase I protein, or a functional fragment thereof, and at least one polyethylene glycol oligomer. In some embodiments, the pegylated recombinant human Arginase I protein comprises at least two polyethylene glycol oligomers, wherein each polyethylene glycol oligomer weighs from about 20 kilodaltons to about 40 kilodaltons. In some embodiments the pegylated recombinant Arginase I protein, or a functional fragment thereof, comprises from about 4 to about 13 polyethylene glycol oligomers, wherein each polyethylene glycol oligomer weighs about 5 kilodaltons.

In some embodiments, the purified pegylated recombinant human Arginase I, or a functional fragment thereof, modulates inflammation by inhibiting T-cell polarization. In some embodiments, the purified pegylated recombinant human Arginase I, or a functional fragment thereof, inhibits T-cell polarization by modulating cytokine release. In some embodiments, the purified pegylated recombinant human Arginase I, or a functional fragment thereof, modulates expression of Interleukin 6 (IL-6). In some embodiments, the purified pegylated recombinant human Arginase I, or a functional fragment thereof, modulates expression of Interferon gamma (INFγ). In some embodiments, the administration of the purified pegylated recombinant human Arginase I, or a functional fragment thereof, depletes the level of arginine in the plasma of a subject to below 10 μM.

In some embodiments, the pharmaceutical composition and method provide a method for treating an autoimmune disorder. In some embodiments, the autoimmune disorder is multiple sclerosis. In some embodiments, the autoimmune disorder is rheumatoid arthritis.

In some embodiments, the disclosure provides a method of treating a bone condition in a subject in need thereof, the method comprising administering to the subject a therapeutically-effective amount of a purified Arginase, or functional fragment thereof. In some cases, the bone condition is osteoporosis. In other cases, the bone condition is inflammation.

In some embodiments, the purified recombinant human Arginase I is SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. In some embodiments, the recombinant human Arginase I is pegylated.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
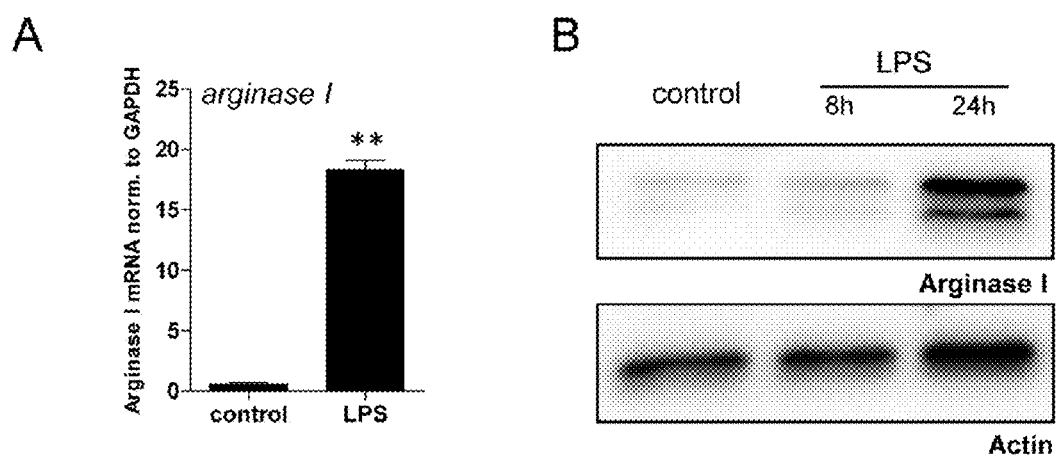
FIG. 1 illustrates the upregulation of Arginase I by LPS in macrophages.

Most living beings are exposed to a number of different antigens every day. However some animals possess immune systems that are capable of responding to such antigens, and protecting against the initiation or formation of disease. To function properly, an immune system must detect a wide variety of antigens, such as virus(es), parasitic worm(s), or allergen(s) and initiate a response in the body against foreign substances, abnormal cells and/or tissues. In a response to an unknown antigen, a healthy immune system begins to produce antibodies.

In some diseases however, an immune system can start producing antibodies that instead of fighting infections, attack the body's own tissues. This can lead to autoimmune diseases. Cancerous growths, including malignant cancerous growths, can also be recognized by the innate immune cells of a subject and trigger an immune response. The activation of innate immune cells triggers numerous intracellular signaling pathways, which require tight control in order to mount an adequate immune response.

Arginase I is a key element of the urea cycle, which converts arginine to urea, and is predominately active in the liver. Arginase I also play a functional role in the immune system. T-cells for instance are dependent on the semi-essential amino acid arginine to mature and respond to infections. Expression of Arginase I in innate immune cells leads to depletion of arginine levels from a physiological system under inflammatory conditions. For example, Arginase I expression in myeloid cells can lead to T-cell anergy and prevent T-helper cell functions.

In mice, Arginase I is expressed by cells of monocytic origin. In humans, Arginase I is constitutively expressed in granulocytes/neutrophils and participates in fungicidal activity. Arginase I expressing macrophages are considered by some to be alternatively activated or M2 macrophages, involved in tissue regeneration and repair but also in the immune defense against multicellular pathogens and parasites. Arginase I expression in murine myeloid cells is regulated by Th2 cytokines IL-4/IL-13. However, it is unclear if human Arginase I and the murine Arginase I work by a similar mechanism of action.

The PI3K/PTEN signaling pathway plays a functional role in numerous physiologically important processes such as innate immunity, cell survival, proliferation, migration and metabolism. The Phosphatidylinositol-3 Kinase (PI3K) signaling pathway can downregulate the expression and release of pro-inflammatory cytokines in some cells. These signaling processes are strictly regulated by the lipid phosphatase PTEN, an antagonist of the PI3K pathway. PTEN is a tumor suppressor that is responsible for the elevated production of cytokines such as Interleukin 6 (IL-6) in response to Toll like receptor (TLR) agonists. PI3K activation is considered to be pro-inflammatory and modulation of the PI3K pathway is indispensable for proper guidance of immune cells to the site of infection or inflammation.

We describe herein experiments characterizing the addition of recombinant pegylated Arginase I to cultured cells and mouse models. The experiments demonstrate that extracellular Arginase I can exert potent anti-inflammatory effects on immune cells. Transfer experiments of conditioned media derived from naïve PTEN$^{-/-}$ macrophages, containing high amounts of Arginase I, showed reduced expression of pro-inflammatory T-cell polarizing cytokines in cultured cells and animal models.

The invention disclosed herein provides compositions and methods for treating conditions associated with the immune system by administrating recombinant Arginase I proteins to a subject to modulate the PI3K/PTEN signaling pathway and cytokine secretion. In some embodiments, the invention disclosed herein provides a method of modulating inflammation by administering to a subject a therapeutically-effective amount of a purified pegylated recombinant human Arginase I.

The disclosure demonstrates that a functional consequence of sustained Arginase I expression in a physiological system is the formation of a hypo-inflammatory environment by diminished function of T-cell mediated pathophysiologic effects in vitro and in vivo. The finding provides a robust and effective method for the modulation of an immune system. Such modulation provides an effective treatment for a variety of immune conditions, such as multiple sclerosis and rheumatoid arthritis. In addition, modulation of the immune system with a recombinant Arginase of the disclosure can be used alongside surgical procedures, for example, to provide a hypo-inflammatory environment that reduces the likelihood of cell/tissue rejection during organ transplantation.

In some aspects, the disclosure provides a method of modulating inflammation, the method comprising administering to a subject a therapeutically-effective amount of a purified pegylated recombinant human Arginase I, or a functional fragment thereof. In some cases, the purified pegylated recombinant human Arginase I, or functional fragment thereof, modulates inflammation by inhibiting T-cell polarization. In some cases, the purified pegylated recombinant human Arginase I inhibits T-cell polarization by modulating cytokine release.

Another aspect of the disclosure provides a pharmaceutical composition comprising a purified recombinant human Arginase I protein conjugated to at least one polyethylene glycol oligomer. In some cases, the at least one polyethylene glycol oligomer is methoxy poly(ethylene glycol).

The disclosure also demonstrates a functional role for Arginases in bone physiology. Bone formation is a multi-complex procedure that includes many stages, and each one of them presents as a potential target for therapeutic intervention. Inflammation can also interfere with the ability of a vertebrate body to repair bone mass. In some aspects, the disclosure demonstrates that expression of Arginase I is lost during osteoclastogenesis, and addition of a recombinant Arginase I during osteoclast differentiation can modulate at least osteoclastogenesis. The disclosure also demonstrates that blockage if osteoclastogenesis is dependent on the catalytic functions of recombinant Arginase I. The findings suggest that modulation of Arginase expression can provide an effective treatment for a variety of bone conditions, including osteoporosis. Modulation of Arginase I expression can also provide an effective treatment for osteoporosis by reducing chronic inflammation in the bone, which can be an aggravating factor in osteoporosis.

Methods of Treating Immune Disorders, Bone Conditions, and Cancers.

The methods, compositions, and kits of this disclosure may comprise a method to treat, arrest, reverse, or ameliorate a disease. In some cases, the disease may be an autoimmune disease. In some cases, the disease may be a bone condition, such as osteoporosis. In some cases, the modulation is achieved by administrating a therapeutically-effective dose of a recombinant Arginase protein or a functional fragment thereof. In some cases, the protein is recombinant human Arginase I or a functional fragment thereof.

Arginase I is an important modulator of the innate and adaptive immune responses. A plurality of subjects afflicted with immune system disorders and cancers can benefit from the use of a recombinant human Arginase I. Subjects can be humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, infants.

Also recognized herein is the therapeutic potential of a recombinant Arginase protein in treating various bone conditions, such as osteoporosis or inflammation in the bones. The strength and integrity of the vertebrate skeleton, e.g., the human skeleton, depends on a delicate equilibrium between bone resorption by osteoclasts and bone formation by osteoblasts. In osteoporosis, this balance shifts in favor of osteoclasts, and bone resorption exceeds bone formation. In some cases, a recombinant Arginase protein, or fragment thereof, can shift the balance between osteoclast and osteoblast formation.

The activity of a plurality of cells in the immune system can be modulated by a recombinant Arginase I. Non-limiting examples of cells whose activity can be modulated by recombinant Arginase I include: B cells; CD4; CD8; blood cells, including red blood cells and white blood cells; dendritic cells, including dendritic antigen presenting cells; macrophages; memory B cells; memory T cells; monocytes; natural killer cells; neutrophil granulocytes; T-helper cells; and T-killer cells. The activity of a plurality of additional cells can also be modulated by a recombinant Arginase I. Non-limiting examples of cells whose activity can be modulated by recombinant arginase I include hematopoietic stem cells, osteoclasts, osteoblasts, osteoprogenitor, osteocytes, and precursors or derivatives thereof.

Examples of immune diseases or conditions that can be treated with a purified Arginase disclosed herein include rheumatoid arthritis, multiple sclerosis, experimental autoimmune encephalomyelitis, psoriasis, uveitis, diabetes mellitus type 1, systemic lupus erythematosus (SLE), eczema, scleroderma, ulcerative proctitis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, HIV, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis, acute inflammatory conditions, chronic inflammatory conditions, and cancer.

In some embodiments, a bone condition can be treated with a purified Arginase. Non-limiting examples of bone conditions include: osteoporosis, Paget's disease, osteogenesis imperfecta, fibrous dysplasis, or osteomyelitis. In some cases, the bone condition is associated with a misregulation in osteoclast or osteoblast function.

In some embodiments, a cancer is susceptible to treatment with a purified Arginase. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

The treatment may comprise treating a subject (e.g. a patient with a disease and/or a lab animal with a condition) with an Arginase of the disclosure. The disease may be an autoimmune disease. The disease may be an inflammatory disease. The subject may be a human. Treatment may be provided to the subject before clinical onset of disease. Treatment may be provided to the subject after clinical onset of disease. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can comprise administering to a subject a pharmaceutical composition, such as one or more of the pharmaceutical compositions described throughout the disclosure. A treatment can comprise modulating the levels of endogenous arginine in vivo.

Mutant Recombinant Arginases.

Sustained expression of Arginase I proteins can be used clinically to provide a hypo-inflammatory environment in vitro and in vivo (Further described, for instance, in Example 1, and FIGS. 1-6). However, one challenge encountered in formulating a purified Arginase for therapeutic purposes is the formation of protein aggregates in solution due to inter-chain disulfide bond formation. To overcome some of the challenges in preparing a purified Arginase that is suitable for clinical administration, a series of mutations were performed in the sequence of a wild-type human Arginase I. TABLE 1 describes various site-specific mutants of human Arginase I that have been designed to reduce the aggregation of a purified recombinant Arginase I in solution. TABLE 1 also describes various human Arginase I sequences comprising a molecular tag (SEQ ID NO: 9-16).

TABLE 1

| SEQ ID NO: | Sequence |
|---|---|
| SEQ ID NO: 1 | MSAKSRTIGI IGAPFSKGQP RGGVEEGPTV LRKAGLLEKL KEQECDVKDY GDLPFADIPN DSPFQIVKNP RSVGKASEQL AGKVAEVKKN GRISLVLGGD HSLAIGSISG HARVHPDLGV IWVDAHTDIN TPLTTTSGNL HGQPVSFLLK ELKGKIPDVP GFSWVTPCIS AKDIVYIGLR DVDPGEHYIL KTLGIKYFSM TEVDRLGIGK VMEETLSYLL GRKKRPIHLS FDVDGLDPSF TPATGTPVVG GLTYREGLYI TEEIYKTGLL SGLDIMEVNP SLGKTPEEVT RTVNTAVAIT LACFGLAREG NHKPIDYLNP PK |
| SEQ ID NO: 2 | MSAKSRTIGI IGAPFSKGQP RGGVEEGPTV LRKAGLLEKL KEQECDVKDY GDLPFADIPN DSPFQIVKNP RSVGKASEQL AGKVAEVKKN GRISLVLGGD HSLAIGSISG HARVHPDLGV IWVDAHTDIN TPLTTTSGNL HGQPVSFLLK ELKGKIPDVP GFSWVTPCIS AKDIVYIGLR DVDPGEHYIL KTLGIKYFSM TEVDRLGIGK VMEETLSYLL GRKKRPIHLS FDVDGLDPSF TPATGTPVVG GLTYREGLYI TEEIYKTGLL SGLDIMEVNP SLGKTPEEVT RTVNTAVAIT LAAFGLAREG NHKPIDYLNP PK |

TABLE 1-continued

| SEQ ID NO: | Sequence |
|---|---|
| SEQ ID NO: 3 | MSAKSRTIGI IGAPFSKGQP RGGVEEGPTV LRKAGLLEKL<br>KEQECDVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LACFGLAREG NHKPIDYLNP PK |
| SEQ ID NO: 4 | MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPCIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LACFGLAREG NHKPIDYLNP PK |
| SEQ ID NO: 5 | MSAKSRTIGI IGAPFSKGQP RGGVEEGPTV LRKAGLLEKL<br>KEQECDVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LAAFGLAREG NHKPIDYLNP PK |
| SEQ ID NO: 6 | MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPCIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LAAFGLAREG NHKPIDYLNP PK |
| SEQ ID NO: 7 | MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LACFGLAREG NHKPIDYLNP PK |
| SEQ ID NO: 8 | MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LAAFGLAREG NHKPIDYLNP PK |
| SEQ ID NO: 9 | MHHHHHH MSAKSRTIGI IGAPFSKGQP RGGVEEGPTV LRKAGLLEKL<br>KEQECDVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPCIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LACFGLAREG NHKPIDYLNP PK |
| SEQ ID NO: 10 | MHHHHHH MSAKSRTIGI IGAPFSKGQP RGGVEEGPTV LRKAGLLEKL<br>KEQECDVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPCIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LAAFGLAREG NHKPIDYLNP PK |
| SEQ ID NO: 11 | MHHHHHH MSAKSRTIGI IGAPFSKGQP RGGVEEGPTV LRKAGLLEKL<br>KEQECDVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF |

TABLE 1-continued

| SEQ ID NO: | Sequence |
|---|---|
| | TPATGTPVVG GLTYREGLYI TEEIYKTGLL SGLDIMEVNP<br>SLGKTPEEVT RTVNTAVAIT LACFGLAREG NHKPIDYLNP PK |
| SEQ ID NO: 12 | MHHHHHH MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPCIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LACFGLAREG NHKPIDYLNP PK |
| SEQ ID NO: 13 | MHHHHHH MSAKSRTIGI IGAPFSKGQP RGGVEEGPTV LRKAGLLEKL<br>KEQECDVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LAAFGLAREG NHKPIDYLNP PK |
| SEQ ID NO: 14 | MHHHHHH MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPCIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LAAFGLAREG NHKPIDYLNP PK |
| SEQ ID NO: 15 | MHHHHHH MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LACFGLAREG NHKPIDYLNP PK |
| SEQ ID NO: 16 | MHHHHHH MSAKSRTIGI IGAPFSKGQP RGGVEEGPTV LRKAGLLEKL<br>KEQEADVKDY GDLPFADIPN DSPFQIVKNP RSVGKASEQL<br>AGKVAEVKKN GRISLVLGGD HSLAIGSISG HARVHPDLGV<br>IWVDAHTDIN TPLTTTSGNL HGQPVSFLLK ELKGKIPDVP<br>GFSWVTPAIS AKDIVYIGLR DVDPGEHYIL KTLGIKYFSM<br>TEVDRLGIGK VMEETLSYLL GRKKRPIHLS FDVDGLDPSF<br>TPATGTPVVG GLTYREGLYI TEEIYKTGLL SGLDIMEVNP<br>SLGKTPEEVT RTVNTAVAIT LAAFGLAREG NHKPIDYLNP PK |

A mutant recombinant Arginase can comprise one or more mutations. Suitable amino acid modifications for improving the rheology of an Arginase I can be conservative or non-conservative mutations. A mutation can be made such that the encoded amino acid is modified to a polar, non-polar, basic or acidic amino acid. A recombinant Arginase of the invention can be a wild type human Arginase. A recombinant Arginase of the invention can be a mutated human Arginase. A recombinant Arginase I can be generated from recombinant DNA, for example with biomolecular engineering techniques. A purified Arginase I can be an arginase that is extracted from a crude extract, such as a whole cell lysate. A purified recombinant Arginase I can be an Arginase I that is purified from, for example, the crude extract of a biological system designed to express the recombinant Arginase I.

TABLE 1 discloses protein sequences of various mutant recombinant human Arginases I. SEQ ID NO: 1 corresponds to a wild-type human Arginase. SEQ ID NOs 2-8 are mutated sequences of SEQ ID NO: 1. SEQ ID NO: 2 comprises a C303→A303 mutation. SEQ ID NO: 3 comprises a C168→A168 mutation. SEQ ID NO: 4 comprises a C45→A45 mutation. SEQ ID NO: 5 comprises the C303→A303 and C168→A168 double mutations. SEQ ID NO: 6 comprises the C303→A303 and C45→A45 double mutations. SEQ ID NO: 7 comprises the C168→A168 and C45→A45 double mutations. SEQ ID NO: 8 comprises the C303→A303, C168→A168, and C45→A45 triple mutations.

A recombinant human Arginase I can have a molecular tag engineered into the recombinant nucleic acid sequence. A molecular tag can facilitate purification of a recombinant Arginase from a crude expression system. A molecular tag can be, for example, a polyhistidine tag, a glutathione-S-transferase (GST) tag, a maltose binding protein (MBP) tag, or a chitin binding protein (CBP) tag. In some embodiments, a molecular tag comprises a polyhistidine tag. A molecular tag can be present, for example, in the amino-terminus or in the carboxy terminus of a recombinant Arginase.

TABLE 1 also discloses protein sequences of various mutant recombinant human Arginases comprising a molecular tag. SEQ ID NO: 9 corresponds to a wild-type human Arginase comprising a polyhistidine tag. SEQ ID NOs: 10-16 are mutated sequences of SEQ ID NO: 1 comprising a tag. SEQ ID NO: 10 comprises a polyhistidine tag and a C303→A303 mutation. SEQ ID NO: 11 comprises a polyhistidine tag and a C168→A168 mutation. SEQ ID NO: 12 comprises a polyhistidine tag and a C45→A45 mutation. SEQ ID NO: 13 comprises a polyhistidine tag, the C303→A303, and the C168→A168 double mutations. SEQ ID NO: 14 comprises a polyhistidine tag, the C303→A303 and the C45→A45 double mutations. SEQ ID NO: 15 comprises a polyhistidine tag, the C168→A168 and the C45→A45 double mutations. SEQ ID NO: 16 comprises a polyhistidine tag, the C303→A303, the C168→A168, and the C45→A45 triple mutations. In some cases, a therapeutic recombinant human Arginase can be a functional fragment of an Arginase described in TABLE 1.

A recombinant Arginase, or a functional fragment thereof, can be expressed/produced, for example, in vivo from bacterial cells, insect cells, mammalian cells, synthetic cells, or in vitro from cell-free systems or chemical synthesis. A recombinant Arginase I can be coded by any combination of codons in the degenerate code. In some embodiments, nucleotides are replaced by taking note of the genetic code such that a codon is changed to a different codon that codes for the same amino acid residue. In some embodiments, altering the identity of a cysteine residue as described in TABLE 1 can result in a reduction of protein aggregation in solution of: about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In some embodiments, altering the identity of a cysteine residue as described in TABLE 1 can result in no greater than 1% aggregation, no greater than 2% aggregation, no greater than 5% aggregation, no greater than 10% aggregation, no greater than 15% aggregation, no greater than 20% aggregation, no greater than 25% aggregation, no greater than 30% aggregation, no greater than 35% aggregation, no greater than 40% aggregation, no greater than 45% aggregation, no greater than 50% aggregation, no greater than 55% aggregation, no greater than 60% aggregation, no greater than 65% aggregation, no greater than 70% aggregation, no greater than 75% aggregation, no greater than 80% aggregation, no greater than 85% aggregation, no greater than 90% aggregation, or no greater than 95% aggregation in solution.

In some cases, altering the identity of one or more amino acids can reduce the aggregation profile of a recombinant Arginase I in solution. In some cases, a recombinant Arginase I, or a functional fragment thereof, comprises 1 amino acid mutation, 2 amino acid mutations, 3 amino acid mutations, 4 amino acid mutations, 5 amino acid mutations, 6 amino acid mutations, 7 amino acid mutations, 8 amino acid mutations, 9 amino acid mutations, 10 amino acid mutations, 11 amino acid mutations, 12 amino acid mutations, 13 amino acid mutations, 14 amino acid mutations, 15 amino acid mutations, 16 amino acid mutations, 17 amino acid mutations, 18 amino acid mutations, 19 amino acid mutations, 20 amino acid mutations, 21 amino acid mutations, 22 amino acid mutations, 23 amino acid mutations, 24 amino acid mutations, 25 amino acid mutations, 26 amino acid mutations, 27 amino acid mutations, 28 amino acid mutations, 29 amino acid mutations, 30 amino acid mutations, 31 amino acid mutations, 32 amino acid mutations, 33 amino acid mutations, 34 amino acid mutations, 35 amino acid mutations, 36 amino acid mutations, 37 amino acid mutations, 38 amino acid mutations, 39 amino acid mutations, 40 amino acid mutations, 41 amino acid mutations, 42 amino acid mutations, 43 amino acid mutations, 44 amino acid mutations, 45 amino acid mutations, 46 amino acid mutations, 47 amino acid mutations, 48 amino acid mutations, 49 amino acid mutations, or 50 amino acid mutations.

A recombinant Arginase, or a functional fragment thereof, can be purified, for example, from bacterial cells, insect cells, mammalian cells, synthetic cells, or from cell-free systems. In some embodiments, the recombinant arginase is partially purified. In some embodiments, the recombinant arginase is substantially pure. In some embodiments, the recombinant arginase is at least 95% pure. In some embodiments, the recombinant arginase is 99% pure.

A purified recombinant arginase, or a functional fragment thereof, can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pegylated Recombinant Arginases.

An Arginase, or a functional fragment thereof, can be modified with one or more polyethylene glycol molecule(s) (PEGs). The covalent attachment of a PEG(s) oligomer to a drug or therapeutic protein can reduce the immunogenicity and antigenicity of the recombinant Arginase I from the subject's immune system. The covalent attachment of a PEG(s) oligomer to a drug or therapeutic protein can increase the hydrodynamic size of the recombinant Arginase, which can prolong the half-life of a pegylated recombinant human Arginase I in solution. PEG oligomers for use in the present invention can be, for example, $-(CH_2CH_2O)_n-$ or $-(CH_2CH_2O)_n-CH_2CH_2-$, but can also include polyalkylene glycols including, but not limited to polypropylene- or polybutylene glycols, methoxy poly(ethylene glycol), or methoxy poly(ethylene glycol) propionic acid (mPEG-acid) where n can be from about 1 to about 400.

An Arginase, or a functional fragment thereof, can be modified with various types of PEG molecules. In some embodiments, a PEG oligomer is methoxy poly(ethylene glycol) succinimidyl proprionate (mPEG-SPA). In some embodiments, a PEG oligomer is a methoxy poly(ethylene glycol) propionic acid (mPEG-acid). In some cases, the disclosure provides a pharmaceutical composition comprising, a purified recombinant human Arginase I protein and at least one polyethylene glycol oligomer. In some cases, the pegylated recombinant human Arginase I protein comprises at least two polyethylene glycol oligomers. In some cases the polyethylene glycol oligomer weighs from about 20 kilodaltons to about 40 kilodaltons. In some cases the pegylated recombinant human Arginase I protein comprises from about 4 polyethylene glycol molecules to about 13 polyethylene glycol oligomer. In some cases the polyethylene glycol oligomer weighs about 5 kilodaltons.

The covalent attachment of an Arginase, or a functional fragment thereof, to a polymer polyethylene glycol of interest can change the physicochemical characteristics of the Arginase. Examples of physicochemical characteristics that can be altered by binding to a PEG include immunogenicity, in vitro and in vivo biological activity, absorption rate and bioavailability, biodistribuition, pharmacokinetic (PK) and pharmacodynamic profiles (PD), and toxicity. In some embodiments, a pegylated Arginase has a reduced immunogenicity. —NH$_2$, —COOH, —OH, —SH, and disulfide bonds are examples of chemical groups in the amino acid side chain of an Arginase that could react with a PEG oligomer. The amine in the N-terminus and the carboxyl group in the C-terminus can also react with a PEG oligomer.

PEG reagents for protein pegylation can be activated PEGs. Activated PEGs can be used for amine pegylation, thiol pegylation, or N-terminal pegylation. PEG reagents are commercially available in different lengths, shapes and chemistry allowing them to react with particular functional groups of proteins for their covalent attachment. Non-limiting examples of commercial suppliers of PEG include NOF Corporation (Japan); SunBio (South Korea); Chirotech Technology Limited (UK); JenKem (China); Creative PEGWorks (USA), Sigma-Aldrich (Milwaukee, Wis.), Dendritech (Midland, Mich.), or Polysciences™ (Warrington, Pa.).

Non-limiting examples of commercially available PEGs suitable for use in the invention include, but are not limited to those available from Nektar Therapeutics, San Carlos, Calif., such as mPEG-NH$_2$ (Mw about 10 kDa, about 20 kDa), methoxy PEG Succinimidyl α-Methylbutanoate (SMB), SMB-PEG-SMB, methoxy PEG Succinimidyl Propionate (mPEG-SPA), Branched PEG N-Hydroxysuccinimide (mPEG2-NHS), mPEG-CM-HBA-NHS, NHS-HBA-CM-PEG-CM-HBA-NHS, mPEG-ButyrALD, ButyrALD-PEG-ButyrALD, Branched PEG ButyrALD (mPEG2-ButyrALD), Ortho-pyridylthioester (mPEG-OPTE), mPEG Maleimide (MAL), MAL-PEG-MAL, Branched PEG Maleimide (mPEG2-MAL), Forked Maleimide (mPEG-MAL2 and mPEG2-MAL2), mPEG-Ortho-pyridyldisulfide (mPEG-OPSS), OPSS-PEG-OPSS, mPEG-SH, SH-PEG-SH, Amine-PEG-Acid, Boc-PEG-NHS, Fmoc-PEG-NHS, MAL-PEG-NHS, Vinylsulfone-PEG-NHS, Acrylate-PEG-NHS Ester.

Non-limiting examples of PEGs that can be used in amine pegylation include, for example, PEGs manufactured by Jenken Technology USA such as: Y-shape PEG NHS Esters, Y-shape PEG Carboxyl, Glucose PEG NHS Ester, Galactose PEG NHS Ester, Methoxy PEG Succinimidyl Carboxymethyl Ester, Methoxy PEG Carboxyl, Methoxy PEG Succinimidyl Butanoate, Methoxy PEG Succinimidyl Hexanoate, Methoxy PEG Hexanoic Acid, Methoxy PEG Succinimidyl Succinamide, Methoxy PEG Succinimidyl Glutaramide, Methoxy PEG Succinimidyl Carbonate, Methoxy PEG Nitrophenyl Carbonate, Methoxy PEG Succinimidyl Succinate, Methoxy PEG Succinimidyl Glutarate. Non-limiting examples of PEGs that can be used in thiol pegylation include Y-shape PEG Maleimide, Methoxy PEG Maleimide, Methoxy PEG Vinylsulfone, Methoxy PEG Thiol. Non-limiting examples of PEGs that can be used in N-terminal pegylation include, for example, PEGs manufactured by Jenken Technology USA such as: Y-shape PEG Aldehyde, Y-shape PEG Acetaldehyde, Y-shape PEG Propionaldehyde, Methoxy PEG Propionaldehyde.

In some cases a recombinant Arginase, or a functional fragment thereof, can have a molecular weight that is small compared to the PEG oligomer to which it is attached. The molecular weight of a PEG oligomer can be, for example, no greater than 100 kilodaltons (kDa), no greater than 95 kilodaltons, no greater than 90 kilodaltons, no greater 85 than kilodaltons (kDa), no greater than 80 kilodaltons (kDa), no greater than 75 kilodaltons (kDa), no greater than 70 kilodaltons (kDa), no greater than 65 kilodaltons (kDa), no greater than 60 kilodaltons (kDa), no greater than 55 kilodaltons (kDa), no greater than 50 kilodaltons (kDa), no greater than 45 kilodaltons (kDa), no greater than 40 kilodaltons (kDa), no greater than 35 kilodaltons (kDa), no greater than 30 kilodaltons (kDa), no greater than 25 kilodaltons (kDa), no greater than 20 kilodaltons (kDa), no greater than 15 kilodaltons (kDa), no greater than 10 kilodaltons (kDa), no greater than 5 kilodaltons (kDa), no greater than 1 kilodalton (kDa), or no greater than 500 daltons (Da).

In some cases, the molecular weight of a PEG molecule can be greater than 500 daltons (Da), greater than 1 kilodalton (kDa), greater than 5 kilodaltons (kDa), greater than 10 kilodaltons (kDa), greater than 15 kilodaltons (kDa), greater than 20 kilodaltons (kDa), greater than 25 kilodaltons (kDa), greater than 30 kilodaltons (kDa), greater than 35 kilodaltons (kDa), greater than 40 kilodaltons (kDa), greater than 45 kilodaltons (kDa), greater than 50 kilodaltons (kDa), greater than 55 kilodaltons (kDa), greater than 60 kilodaltons (kDa), greater than 65 kilodaltons (kDa), greater than 70 kilodaltons (kDa), greater than 75 kilodaltons (kDa), greater than 80 kilodaltons (kDa), greater than 85 kilodaltons (kDa), greater than 90 kilodaltons (kDa), greater than 95 kilodaltons (kDa), greater than 100 kilodaltons (kDa).

In some cases the molecular weight of a PEG oligomer can be from about 1 kilodalton (kDa) to about 5 kilodaltons (kDa), from about 1 kilodalton (kDa) to about 10 kilodaltons (kDa), from about 10 kilodaltons (kDa) to about 20 kilodaltons (kDa), from about 10 kilodaltons (kDa) to about 30 kilodaltons (kDa), from about 10 kilodaltons (kDa) to about 40 kilodaltons (kDa), from about 10 kilodaltons (kDa) to about 50 kilodaltons (kDa), from about 20 kilodaltons (kDa) to about 30 kilodaltons (kDa), from about 20 kilodaltons (kDa) to about 40 kilodaltons (kDa), from about 20 kilodaltons (kDa) to about 50 kilodaltons (kDa), from about 30 kilodaltons (kDa) to about 40 kilodaltons (kDa), from about 30 kilodaltons (kDa) to about 50 kilodaltons (kDa).

In some embodiments, the molecular weight of a PEG oligomer is about 5 kilodaltons (kDa). In some embodiments, the molecular weight of a PEG oligomer is from about 20 kilodaltons (kDa) to about 40 kilodaltons (kDa).
Recombinant Arginases Modified with PEG Oligomer(s).

The present disclosure provides PEG oligomers that can be attached to recombinant Arginases, such as SEQ ID NOs: 1-16 to modify or improve rheology properties. PEG oligomers can also be attached to functional fragments of the recombinant Arginases. The improvements can lead to improved formulations. A PEG oligomer can be covalently attached to a recombinant Arginase. A PEG oligomer can be attached to the N-terminus, the C-terminus, or through a side-chain of the recombinant Arginase. For example, a PEG oligomer could be attached to a terminus of the amino acid sequence of the recombinant Arginase, or could be attached to a side chain, such as the side chain of a lysine, serine, threonine, cysteine, tyrosine, aspartic acid, or glutamic acid residue. The attachment can be via an amide bond, an ester bond, an ether bond, a carbamate bond, or a thioether bond.

Figure 14:
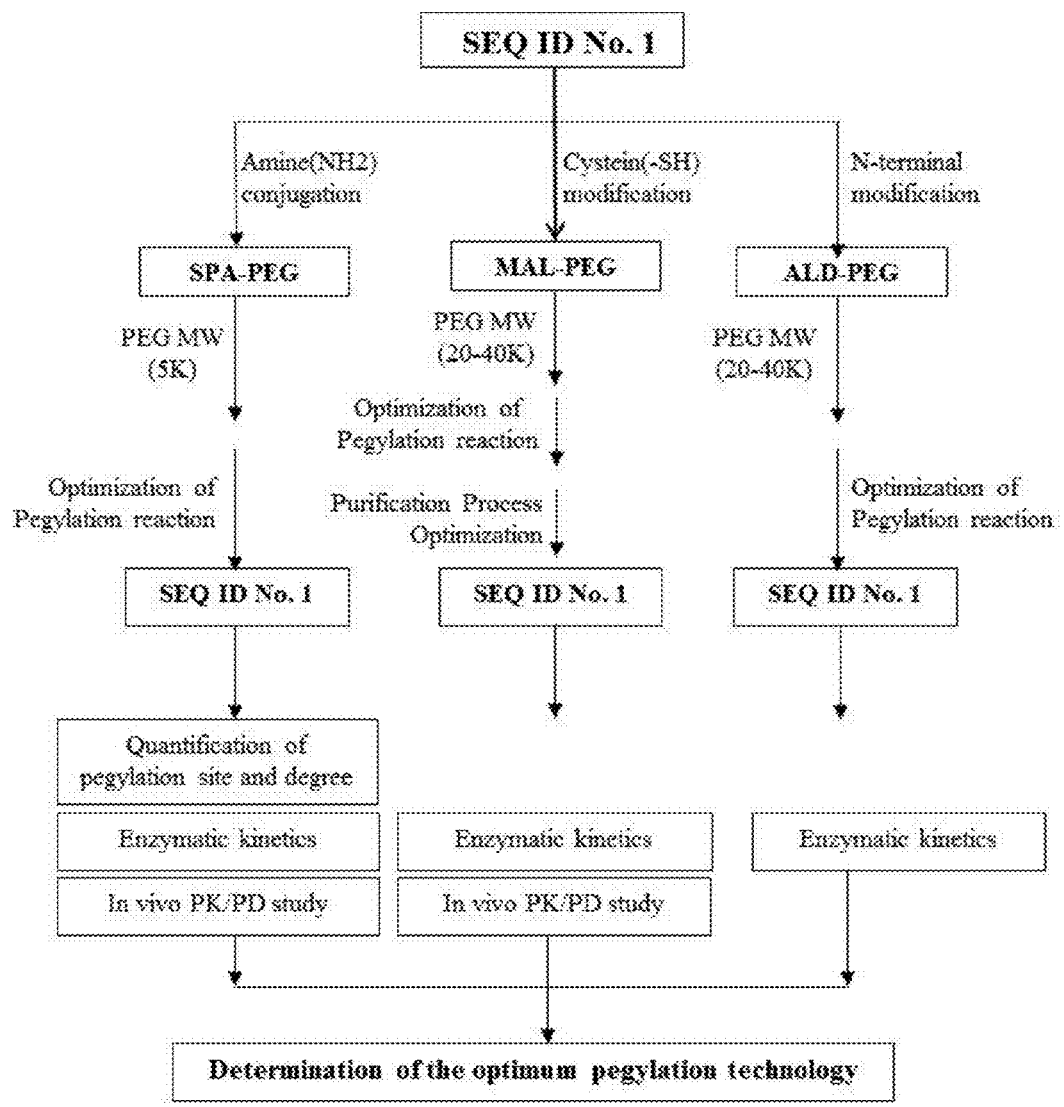
FIG. 14 is a schematic of a process utilized for optimizing a pharmaceutical composition comprising a purified Arginase I.

In some cases a polyethylene glycol molecule(s) is conjugated to a cysteine residue of a purified recombinant human Arginase I. In some cases a polyethylene glycol molecule is conjugated to an amine residue of a purified recombinant human Arginase I protein. In some cases a polyethylene glycol molecule is conjugated to the N-terminus of a purified recombinant human Arginase I protein. FIG. 14 illustrates a process that was utilized to evaluate the pegylation of a recombinant human Arginase I.

Pharmaceutical Compositions.

A pharmaceutical composition of the invention can be a combination of any recombinant Arginase(s) described herein with other chemical components, such as carriers, stabilizers, diluents, dispersing agents, suspending agents, thickening agents, and/or excipients. The pharmaceutical composition facilitates administration of the recombinant Arginase to an organism. Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, and topical administration. A pharmaceutical composition can be administered in a local or systemic manner, for example, via injection of the recombinant Arginase directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the recombinant Arginase(s) in water-soluble form. Suspensions of the recombinant Arginase(s) can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduces the aggregation of the recombinant Arginase(s) to allow for the preparation of highly concentrated solutions. Alternatively, the recombinant Arginases can be lyophilized or in powder form for re-constitution with a suitable vehicle, e.g., sterile pyrogen-free water, before use. In some embodiments, a purified pegylated recombinant Arginase of the invention is administered intravenously.

The recombinant Arginase(s) can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of the recombinant Arginase(s) described herein are administered in pharmaceutical compositions to a subject suffering from a condition that affects the immune system. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes. The pharmaceutical compositions can include at least one pharmaceutically acceptable carrier, diluent, or excipient and compounds described herein as free-base or pharmaceutically-acceptable salt form.

Methods for the preparation of recombinant Arginase(s) comprising the compounds described herein include formulating the recombinant Arginase(s) with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a recombinant Arginase(s) is dissolved, emulsions comprising a recombinant Arginase(s), or a solution containing liposomes, micelles, or nanoparticles comprising a recombinant Arginase(s) as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

Methods of Administration.

Pharmaceutical compositions containing recombinant Arginase(s), or functional fragments of recombinant Arginases, described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Recombinant Arginases(s) can also be administered to lessen a likelihood of developing, contracting, or worsening a condition. Amounts effective for this use can vary based on the severity and course of the disease or condition, previous therapy, the subject's health status, weight, and response to the drugs, and the judgment of the treating physician. In some embodiments, the invention described herein provides a method of treating an inflammatory disease in a subject, the method comprising administering to the subject a therapeutically-effective amount of a purified recombinant arginase. In some embodiments, the inflammatory disease is rheumatoid arthritis. In some embodiments, the inflammatory disease is multiple sclerosis. In some embodiments, the inflammatory disease is a chronic or acute inflammation in a bone. In some embodiments, the purified recombinant arginase is a pegylated recombinant human Arginase I. In some embodiments, the human Arginase I is SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. In some embodiments, the pegylated recombinant human Arginase I comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

Multiple recombinant Arginase(s) can be administered in any order or simultaneously. In some cases, multiple functional fragments of recombinant Arginases can be administered in any order or simultaneously. If simultaneously, the multiple recombinant Arginase(s) can be provided in a single, unified form, such as an intravenous injection, or in multiple forms, for example, as multiple intravenous injections or pills. The recombinant Arginase(s) can be packed together or separately, in a single package or in a plurality of packages. One or all of the recombinant Arginase(s) can be given in multiple doses. If not simultaneous, the timing between the multiple doses may vary to as much as about a month.

Compounds and compositions of the invention can be packaged as a kit. In some embodiments, a kit includes written instructions on the use of the compounds and compositions. In some embodiments the invention provides a method of modulating inflammation, the method comprising administering to a subject a therapeutically-effective amount of a purified pegylated recombinant human Arginase I, wherein the administration modulates the inflammation. In some embodiments the therapeutically-effective amount of a purified pegylated recombinant human Arginase I is administered for at least 24 hours. In some embodiments the therapeutically-effective amount of a purified pegylated recombinant human Arginase I is administered for at least one week. In some embodiments the therapeutically-effective amount of a purified pegylated recombinant human Arginase I is administered for at least two weeks.

Recombinant Arginase(s), or functional fragments thereof, described herein can be administered before, during, or after the occurrence of a disease or condition, and the timing of administering the composition containing a recombinant Arginase(s) can vary. For example, the recombinant Arginase(s) can be used as a prophylactic and can be administered continuously to subjects with a propensity to conditions or diseases in order to lessen a likelihood of the occurrence of the disease or condition. The recombinant Arginase(s) can be administered to a subject during or as soon as possible after the onset of the symptoms. The administration of the recombinant Arginases(s) can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In some embodiments, the administration of a pegylated recombinant human Arginase I of the disclosure is an intravenous administration. A recombinant Arginase(s) can be administered as soon as is practicable after the onset of an immune disease or condition is detected or suspected, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. In some embodiments, a recombinant Arginase(s) can be administered for at least 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject. In some embodiments, pegylation of the recombinant Arginase modulates the half-life of the recombinant Arginase in vivo.

Dosages.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged tablets or capsules, and powders in vials or ampoules. Aqueous suspension compositions can be packaged in single-dose non-reclosable containers. Multiple-dose reclosable containers can be used, for example, in combination with a preservative or without a preservative. In some embodiments, the pharmaceutical composition does not comprise a preservative. Formulations for parenteral injection can be presented in unit dosage form, for example, in ampoules, or in multi-dose containers with a preservative.

A recombinant Arginase(s), or a functional fragment thereof, described herein can be present in a composition in a range of from about 1 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A recombinant Arginase(s), or a functional fragment thereof, described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

The therapeutically effective dose of a pegylated recombinant Arginase, or a functional fragment thereof, of the invention can be from about 1 ng/kg to about 10 ng/kg, from about 1 ng/kg to about 100 ng/kg, from about 1 ng/kg to about 1 mg/kg, from about 1 ng/kg to about 10 mg/kg, from about 1 ng/kg to about 100 mg/kg, from about 1 ng/kg to about 250 mg/kg, from about 1 ng/kg to about 500 mg/kg, from about 1 ng/kg to about 750 mg/kg, from about 1 ng/kg to about 1,000 mg/kg, from about 1 ng/kg to about 1,250 mg/kg, from about 1 ng/kg to about 1,500 mg/kg, from about 1 ng/kg to about 1,750 mg/kg, from about 1 ng/kg to about 2,000 mg/kg, from about 10 ng/kg to about 100 ng/kg, from about 10 ng/kg to about 1 mg/kg, from about 10 ng/kg to about 10 mg/kg, from about 10 ng/kg to about 100 mg/kg, from about 10 ng/kg to about 500 mg/kg, from about 10 ng/kg to about 750 mg/kg, from about 10 ng/kg to about 1,000 mg/kg, from about 10 ng/kg to about 1,250 mg/kg, from about 10 ng/kg to about 1,500 mg/kg, from about 10 ng/kg to about 2,000 mg/kg, from about 100 ng/kg to about 1 mg/kg, from about 100 ng/kg to about 10 mg/kg, from about 100 ng/kg to about 100 mg/kg, from about 100 ng/kg to about 250 mg/kg, from about 100 ng/kg to about 500 mg/kg, from about 100 ng/kg to about 750 mg/kg, from about 100 ng/kg to about 1,000 mg/kg, from about 100 ng/kg to about 1,250 mg/kg, from about 100 ng/kg to about 1,500 mg/kg, from about 100 ng/kg to about 1,750 mg/kg, from about 100 ng/kg to about 2,000 mg/kg, from about 1 mg/kg to about 10 mg/kg, from about 1 mg/kg to about 100 mg/kg, from about 1 mg/kg to about 500 mg/kg, from about 1 mg/kg to about 750 mg/kg, from about 1 mg/kg to about 1,000 mg/kg, from about 1 mg/kg to about 1,250 mg/kg, from about 1 mg/kg to about 1,500 mg/kg, from about 1 mg/kg to about 1,750 mg/kg, from about 1 mg/kg to about 2,000 mg/kg, from about 10 mg/kg to about 100 mg/kg, from about 10 mg/kg to about 500 mg/kg, from about 10 mg/kg to about 750 mg/kg, from about 10 mg/kg to about 1,000 mg/kg, from about 10 mg/kg to about 1,250 mg/kg, from about 10 mg/kg to about 1,500 mg/kg, from about 10 mg/kg to about 1,750 mg/kg, from about 10 mg/kg to about 2,000 mg/kg, from about 100 mg/kg to about 500 mg/kg, from about 100 mg/kg to about 750 mg/kg, from about 100 mg/kg to about 1,000 mg/kg, from about 100 mg/kg to about 1,250 mg/kg, from about 100 mg/kg to about 1,500 mg/kg, from about 100 mg/kg to about 1,750 mg/kg, from about 100 mg/kg to about 2,000 mg/kg, from about 500 mg/kg to about 750 mg/kg, from about 500 mg/kg to about 1,000 mg/kg, from about 500 mg/kg to about 1,250 mg/kg, from about 500 mg/kg to about 1,500 mg/kg, from about 500 mg/kg to about 1,750 mg/kg, from about 500 mg/kg to about 2,000 mg/kg, from about 750 mg/kg to about 1,000 mg/kg, from about 750 mg/kg to about 1,250 mg/kg, from about 750 mg/kg to about 1,500 mg/kg, from about 750 mg/kg to about 1,750 mg/kg, from about 750 mg/kg to about 2,000 mg/kg, from about 1,000 mg/kg to about 1,250 mg/kg, from about 1,000 mg/kg to about 1,500 mg/kg, from about 1,000 mg/kg to about 1,750 mg/kg, or from about 1,000 mg/kg to about 2,000 mg/kg.

In some embodiments, the therapeutically-effective amount of a purified pegylated recombinant human Arginase I, or a functional fragment thereof, is from about 1 mg/kg to about 10 mg/kg. In some embodiments, the therapeutically-effective amount of the purified pegylated recombinant human Arginase I is from about 10 mg/kg to about 100 mg/kg. In some embodiments, the therapeutically-effective amount of the purified pegylated recombinant human Arginase I, or a functional fragment thereof, is greater than 100 mg/kg.

Pharmacokinetic and Pharmacodynamic Measurements.

Pharmacokinetic and pharmacodynamic data can be obtained by various experimental techniques. Appropriate pharmacokinetic and pharmacodynamic profile components describing a particular composition can vary due to variations in drug metabolism in different subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined by calculating the average of all subject's measurements for each parameter measured.

A dose can be modulated to achieve a desired pharmacokinetic or pharmacodynamics profile, such as a desired or effective blood profile, as described herein. To better characterize the enzyme kinetics of recombinant human Arginase I in vitro the $K_m$, $V_{max}$, $K_{cat}$, and $K_{cat}/K_m$ of five different recombinant Arginases were measured. The summary of the enzyme kinetics study for five human recombinant Arginases is shown in TABLE 2.

TABLE 2

| Mutant | $K_m$ (mM) | $V_{max}$ (µmol * ml$^{-1}$ * min$^{-1}$) | $K_{cat}$ (sec$^{-1}$) | $K_{cat}/K_m$ (mM$^{-1}$sec$^{-1}$) |
|---|---|---|---|---|
| SEQ ID NO: 1 | 2.37 | 0.037 | 546.4 | 229.8 |
| SEQ ID NO: 5 | 1.80 | 0.027 | 397 | 220.4 |
| SEQ ID NO: 6 | 2.19 | 0.034 | 498 | 226.7 |
| SEQ ID NO: 8 | 2.59 | 0.038 | 562.8 | 216.8 |
| SEQ ID NO: 7 | 2.02 | 0.032 | 470.8 | 232.9 |

The pharmacokinetics parameters can be any parameters suitable for describing the plasma profiles of a recombinant Arginase I, or a functional fragment thereof, of the invention. For example, the pharmacokinetics profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing a recombinant Arginase I, or a functional fragment thereof. The $C_{max}$ can be, for example, not less than about 1 µg/mL; not less than about 5 µg/mL; not less than about 10 µg/mL; not less than about 15 µg/mL; not less than about 20 µg/mL; not less than about 25 µg/mL; not less than about 50 µg/mL; not less than about 75 µg/mL; not less than about 100 µg/mL; not less than about 200 µg/mL; not less than about 300 µg/mL; not less than about 400 µg/mL; not less than about 500 µg/mL; not less than about 600 µg/mL; not less than about 700 µg/mL; not less than about 800 µg/mL; not less than about 900 µg/mL; not less than about 1000 µg/mL; not less than about 1250 µg/mL; not less than about 1500 µg/mL; not less than about 1750 µg/mL; not less than about 2000 µg/mL; or any other $C_{max}$ appropriate for describing a pharmacokinetic profile of an Arginase described herein. The $C_{max}$ can be, for example, about 1 µg/mL to about 5,000 µg/mL; about 1 µg/mL to about 4,500 µg/mL; about 1 µg/mL to about 4,000 µg/mL; about 1 µg/mL to about 3,500 µg/mL; about 1 µg/mL to about 3,000 µg/mL; about 1 µg/mL to about 2,500 µg/mL; about 1 µg/mL to about 2,000 µg/mL; about 1 µg/mL to about 1,500 µg/mL; about 1 µg/mL to about 1,000 µg/mL; about 1 µg/mL to about 900 µg/mL; about 1 µg/mL to about 800 µg/mL; about 1 µg/mL to about 700 µg/mL; about 1 µg/mL to about 600 µg/mL; about 1 µg/mL to about 500 µg/mL; about 1 µg/mL to about 450 µg/mL; about 1 µg/mL to about 400 µg/mL; about 1 µg/mL to about 350 µg/mL; about 1 µg/mL to about 300 µg/mL; about 1 µg/mL to about 250 µg/mL; about 1 µg/mL to about 200 µg/mL; about 1 µg/mL to about 150 µg/mL; about 1 µg/mL to about 125 µg/mL; about 1 µg/mL to about 100 µg/mL; about 1 µg/mL to about 90 µg/mL; about 1 µg/mL to about 80 µg/mL; about 1 µg/mL to about 70 µg/mL; about 1 µg/mL to about 60 µg/mL; about 1 µg/mL to about 50 µg/mL; about 1 µg/mL to about 40 µg/mL; about 1 µg/mL to about 30 µg/mL; about 1 µg/mL to about 20 µg/mL; about 1 µg/mL to about 10 µg/mL; about 1 µg/mL to about 5 µg/mL; about 10 µg/mL to about 4,000 µg/mL; about 10 µg/mL to about 3,000 µg/mL; about 10 µg/mL to about 2,000 µg/mL; about 10 µg/mL to about 1,500 µg/mL; about 10 µg/mL to about 1,000 µg/mL; about 10 µg/mL to about 900 µg/mL; about 10 µg/mL to about 800 µg/mL; about 10 µg/mL to about 700 µg/mL; about 10 µg/mL to about 600 µg/mL; about 10 µg/mL to about 500 µg/mL; about 10 µg/mL to about 400 µg/mL; about 10 µg/mL to about 300 µg/mL; about 10 µg/mL to about 200 µg/mL; about 10 µg/mL to about 100 µg/mL; about 10 µg/mL to about 50 µg/mL; about 25 µg/mL to about 500 µg/mL; about 25 µg/mL to about 100 µg/mL; about 50 µg/mL to about 500 µg/mL; about 50 µg/mL to about 100 µg/mL; about 100 µg/mL to about 500 µg/mL; about 100 µg/mL to about 400 µg/mL; about 100 µg/mL to about 300 µg/mL; or about 100 µg/mL to about 200 µg/mL.

The $T_{max}$ of an Arginase I, or a functional fragment thereof, described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ of an Arginase I, or a functional fragment thereof, described herein can be, for example, not less than about 100 µg·hr/mL, not less than about 125 µg·hr/mL, not less than about 150 µg·hr/mL, not less than about 175 µg·hr/mL, not less than about 200 µg·hr/mL, not less than about 250 µg·hr/mL, not less than about 300 µg·hr/mL, not less than about 350 µg·hr/mL, not less than about 400 µg·hr/mL, not less than about 500 µg·hr/mL, not less than about 600 µg·hr/mL, not less than about 700 µg·hr/mL, not less than about 800 µg·hr/mL, not less than about 900 µg·hr/mL, not less than about 1000 µg·hr/mL, not less than about 2000 µg·hr/mL, not less than about 3000 µg·hr/mL, not less than about 4000 µg·hr/mL, not less than about 5000 µg·hr/mL, not less than about 6000 µg·hr/mL, not less than about 7000 µg·hr/mL, not less than about 8000 µg·hr/mL, not less than about 9000 µg·hr/mL, not less than about 10000 µg·hr/mL, not less than about 11000 µg·hr/mL, not less than about 12000 µg·hr/mL, not less than about 13000 µg·hr/mL, not less than about 14000 µg·hr/mL, not less than about 15000 µg·hr/mL, not less than about 16000 µg·hr/mL, not less than about 17000 µg·hr/mL, not less than about 18000 µg·hr/mL, not less than about 19000 µg·hr/mL, not less than about 20000 µg·hr/mL, not less than about 21000 µg·hr/mL, not less than about 22000 µg·hr/mL, not less than about 23000 µg·hr/mL, not less than about 24000 µg·hr/mL, not less than about 25000 µg·hr/mL, not less than about 26000 µg·hr/mL, not less than about 27000 µg·hr/mL, not less than about 28000 µg·hr/mL, not less than about 29000 µg·hr/mL, not less than about 30000 µg·hr/mL, not less than about 31000 µg·hr/mL, not less than about 32000 µg·hr/mL, not less than about 33000 µg·hr/mL, not less than about 34000 µg·hr/mL, not less than about 35000 µg·hr/mL, or any other $AUC_{(0-inf)}$ appropriate for describing a pharmacokinetic profile of an Arginase described herein.

The $AUC_{(0-inf)}$ of an Arginase I, or a functional fragment thereof, described herein can be, for example, about 1,000 µg·hr/mL to about 1,250 µg·hr/mL; about 1,250 µg·hr/mL to about 1,500 µg·hr/mL; about 1,500 µg·hr/mL to about 1,750 µg·hr/mL; about 1,750 µg·hr/mL to about 2,000 µg·hr/mL; about 2,000 µg·hr/mL to about 2,500 µg·hr/mL; about 2,500 µg·hr/mL to about 3,000 µg·hr/mL; about 3,000 µg·hr/mL to about 3,500 µg·hr/mL; about 3,500 µg·hr/mL to about 4,000 µg·hr/mL; about 4,000 µg·hr/mL to about 4,500 µg·hr/mL; about 4,500 µg·hr/mL to about 5,000 µg·hr/mL; about 5,000 µg·hr/mL to about 5,500 µg·hr/mL; about 5,500 µg·hr/mL to about 6,000 µg·hr/mL; about 6,000 µg·hr/mL to about 6,500 µg·hr/mL; about 6,500 µg·hr/mL to about 7,000 µg·hr/mL; about 7,000 µg·hr/mL to about 7,500 µg·hr/mL; about 7,500 µg·hr/mL to about 8,000 µg·hr/mL; about 8,000 µg·hr/mL to about 8,500 µg·hr/mL; about 8,500 µg·hr/mL to about 9,000 µg·hr/mL; about 9,000 µg·hr/mL to about 9,500 µg·hr/mL; about 9,500 µg·hr/mL to about 10,000 µg·hr/mL; about 10,000 µg·hr/mL to about 20,000 µg·hr/mL; about 20,000 µg·hr/mL to about 30,000 µg·hr/mL; about 30,000 µg·hr/mL to about 40,000 µg·hr/mL; about 40,000 µg·hr/mL to about 50,000 µg·hr/mL; about 50,000 µg·hr/mL to about 60,000 µg·hr/mL; about 60,000 µg·hr/mL to about 70,000 µg·hr/mL; about 70,000 µg·hr/mL to about 80,000 µg·hr/mL; about 80,000 µg·hr/mL to about 90,000 µg·hr/mL; or about 90,000 µg·hr/mL to about 100,000 µg·hr/mL.

The plasma concentration of a recombinant human Arginase I, or a functional fragment thereof, described herein can be, for example, not less than about 1 g/mL, not less than about 2 µg/mL, not less than about 3 µg/mL, not less than about 4 µg/mL, not less than about 5 µg/mL, not less than about 6 µg/mL, not less than about 7 µg/mL, not less than about 8 µg/mL, not less than about 9 µg/mL, not less than about 10 µg/mL, not less than about 11 µg/mL, not less than about 12 µg/mL, not less than about 13 µg/mL, not less than about 14 µg/mL, not less than about 15 µg/mL, not less than about 16 µg/mL, not less than about 17 µg/mL, not less than about 18 µg/mL, not less than about 19 µg/mL, not less than about 20 µg/mL, not less than about 21 µg/mL, not less than about 22 µg/mL, not less than about 23 µg/mL, not less than about 24 µg/mL, not less than about 25 µg/mL, not less than about 26 µg/mL, not less than about 27 µg/mL, not less than about 28 µg/mL, not less than about 29 µg/mL, not less than about 30 µg/mL, not less than about 31 µg/mL, not less than about 32 µg/mL, not less than about 33 µg/mL, not less than about 34 µg/mL, not less than about 35 µg/mL, not less than about 36 µg/mL, not less than about 37 µg/mL, not less than about 38 µg/mL, not less than about 39 µg/mL, not less than about 40 µg/mL, not less than about 41 µg/mL, not less than about 42 µg/mL, not less than about 43 µg/mL, not less than about 44 µg/mL, not less than about 45 µg/mL, not less than about 46 µg/mL, not less than about 47 µg/mL, not less than about 48 µg/mL, not less than about 49 µg/mL, not less than about 50 µg/mL, not less than about 51 µg/mL, not less than about 52 µg/mL, not less than about 53 µg/mL, not less than about 54 µg/mL, not less than about 55 µg/mL, not less than about 56 µg/mL, not less than about 57 µg/mL, not less than about 58 µg/mL, not less than about 59 µg/mL, not less than about 60 µg/mL, not less than about 61 µg/mL, not less than about 62 µg/mL, not less than about 63 µg/mL, not less than about 64 µg/mL, not less than about 65 µg/mL, not less than about 66 µg/mL, not less than about 67 µg/mL, not less than about 68 µg/mL, not less than about 69 µg/mL, not less than about 70 µg/mL, not less than about 71 µg/mL, not less than about 72 µg/mL, not less than about 73 µg/mL, not less than about 74 µg/mL, not less than about 75 µg/mL, not less than about 76 µg/mL, not less than about 77 µg/mL, not less than about 78 µg/mL, not less than about 79 µg/mL, not less than about 80 µg/mL, not less than about 81 µg/mL, not less than about 82 µg/mL, not less than about 83 µg/mL, not less than about 84 µg/mL, not less than about 85 µg/mL, not less than about 86 µg/mL, not less than about 87 µg/mL, not less than about 88 µg/mL, not less than about 89 µg/mL, not less than about 90 µg/mL, not less than about 91 µg/mL, not less than about 92 µg/mL, not less than about 93 µg/mL, not less than about 94 µg/mL, not less than about 95 µg/mL, not less than about 96 µg/mL, not less than about 97 µg/mL, not less than about 98 µg/mL, not less than about 99 µg/mL, not less than about 100 µg/mL, not less than about 105 µg/mL, not less than about 110 µg/mL, not less than about 115 µg/mL, not less than about 120 µg/mL, not less than about 125 µg/mL, not less than about 130 µg/mL, not less than about 135 µg/mL, not less than about 140 µg/mL, not less than about 145 µg/mL, not less than about 150 µg/mL, not less than about 155 µg/mL, not less than about 160 µg/mL, not less than about 165 µg/mL, not less than about 170 µg/mL, not less than about 175 µg/mL, not less than about 180 µg/mL, not less than about 185 µg/mL, not less than about 190 µg/mL, not less than about 195 µg/mL, not less than about 200 µg/mL, not less than about 205 µg/mL, not less than about 210 µg/mL, not less than about 215 µg/mL, not less than about 220 µg/mL, not less than about 225 µg/mL, not less than about 230 µg/mL, not less than about 235 µg/mL, not less than about 240 µg/mL, not less than about 245 µg/mL, not less than about 250 µg/mL, or any other plasma concentration of a compound described herein.

The plasma concentration can be, for example, about 1 µg/mL to about 2 µg/mL; about 1 µg/mL to about 5 µg/mL; about 5 µg/mL to about 10 µg/mL; about 10 µg/mL to about 25 µg/mL; about 25 µg/mL to about 50 µg/mL; about 50 µg/mL to about 75 µg/mL; about 75 ng/mL to about 100 µg/mL; about 100 µg/mL to about 150 µg/mL; about 100 µg/mL to about 200 µg/mL about 150 µg/mL to about 200 µg/mL; about 200 µg/mL to about 250 µg/mL; about 250 µg/mL to about 300 µg/mL; about 300 µg/mL to about 350 µg/mL; about 350 µg/mL to about 400 µg/mL; about 400 µg/mL to about 450 µg/mL; about 450 µg/mL to about 500 µg/mL; about 500 µg/mL to about 600 µg/mL; about 600 µg/mL to about 700 µg/mL; about 700 µg/mL to about 800 µg/mL; about 800 µg/mL to about 900 µg/mL; about 900 µg/mL to about 1,000 µg/mL; about 1,000 µg/mL to about 1,100 µg/mL; about 1,100 µg/mL to about 1,200 µg/mL; about 1,200 µg/mL to about 1,300 µg/mL; about 1,300 µg/mL to about 1,400 µg/mL; about 1,400 µg/mL to about 1,500 µg/mL; about 1,500 µg/mL to about 1,600 µg/mL; about 1,600 µg/mL to about 1,700 µg/mL; about 1,700 µg/mL to about 1,800 µg/mL; about 1,800 µg/mL to about 1,900 µg/mL; or about 1,900 µg/mL to about 2,000 µg/mL.

Example 1. Modulating the Immune System with Recombinant Arginase I

The following experiments were conducted to characterize the function of a purified Arginase in the modulation of an immune condition, such as a condition associated with an inflammation.

Materials and Methods.

Mice: floxed PTEN mice are described by Tak W. Mak (Suzuki, A. et al. 2001. T cell-specific loss of Pten leads to defects in central and peripheral tolerance. *Immunity* 14: 523-534). LysM cre mice were originally described by Clausen et al. (Clausen, B. E. et al. *Transgenic Res.* 8: 265-277). Littermate-controlled experiments were performed with 8-12-week-old wildtype, floxed PTEN cre positive and cre negative mice on a C57Bl/6 background, which were backcrossed for at least 10 generations. DBA mice were used in the collagen induced arthritis experiments. All animals were bred and housed in a SPF facility of the Medical University of Vienna with a 12 h/12 h day/night cycle and constant temperature. Mice of both sexes were used and no gender-specific differences were found.

Genotyping: mice were earmarked 3-4 weeks after birth. DNA from lysed (proteinase K lysis buffer) ear tissue was subjected to direct PCR using GoTaq Polymerase (Promega™). Specific PCRs were performed with following primers: PTEN primer: forward, 5'-CTCCTCTACTCCAT-TCTTCCC-3' (SEQ ID NO: 17), reverse, 5'-ACTCCCAC-CAATGAACAAAC-3' (SEQ ID NO: 18); cre primer: forward, 5'-TCGCGATTATCTTCTATATCTTCAG-3' (SEQ ID NO: 19), reverse, 5'-GCTCGACCAGTTTAGTTACCC-3' (SEQ ID NO: 20).

Preparation and cultivation of primary macrophages: thioglycollate-elicited peritoneal macrophages were generated by injection of 2 ml 4% thioglycollate (Sigma™) into the peritoneal cavity followed by peritoneal lavage with empty medium 3 days later. Isolated macrophages were seeded at a concentration of $1 \times 10^6$ cells/ml in RPMI-1640 medium (Invitrogen™) supplemented with 10% FCS, 1% penicillin/streptomycin/fungizone, 1% L-glutamine, and cultured at 37° C. in a 5% $CO_2$ atmosphere. Cells were allowed to recover overnight and in-vitro stimulations were carried out by supplementing the macrophage culture with following agents and cytokines: 100 ng/ml ultrapure *E. coli* O111:B4 lipopolysaccharide (LPS) (Invivogen™), 100 nM wortmannin (Sigma™), 10 or 200 µM N-hydroxy-L-arginine (Calbiochem™) or 5 ng/ml recombinant mouse IL-4/IL-13 (R&D Systems™). Stimulations were carried out for 3, 8 or 24 hrs for RNA extraction, ABCD assay or protein isolation and cytokine measurement, respectively.

Preparation and cultivation of bone marrow-derived dendritic cells (BMDC): bone marrow cells were flushed from femurs and tibias of indicated mice and cultivated in complete RPMI medium supplemented with 20 ng/ml recombinant mouse GM-CSF (R&D Systems™) at 37° C. in a 5% $CO_2$ atmosphere. Half of the medium was replaced with fresh medium supplemented with 20 ng/ml GM-CSF at day 3 and day 6 after isolation. Dendritic cells (DC) were harvested and activated at day 7 and the maturation status was determined by flow cytometry using fluorescent conjugated antibodies against CD80 (PE-Cy5™) and MHC-II (PerCP-eFluor 710™) (eBioscience™). Samples were incubated with the antibody-mix for 15 min at 4° C. and subsequently acquired on a LSRII Flow Cytometer (Beckton Dickinson™). Data were analyzed using FlowJo™ Software 10.0 (Treestar™) software.

Immunoblotting: cells were homogenized and lysed in Laemmli buffer. Proteins were separated by SDS-PAGE on a 10% denaturing polyacrylamide gel, which was stained with Coomassie Brilliant Blue (Thermo Scientific Pierce™) after electrophoresis. Proteins were blotted onto a polyvinylidene difluoride membrane (PVDF™, Millipore™) and, after blocking with 5% dry milk/0.1% Tween 20, incubated overnight with primary antibody. Following antibodies were used: chicken anti-Arginase 1 (kindly provided by Dr. Morris), rabbit antibodies against iNOS (NEB™), PTEN, STAT6, pSTAT6 (Cell Signaling Technology™), C/EBPβ (Santa Cruz Biotech) or β-Actin (Sigma™). After incubation for 2 hrs at room temperature (RT) with the respective peroxidase-conjugated secondary antibody and following development with SuperSignal West Femto (Pierce™), signals were detected using chemiluminescence (FluorChem HD2 chemiluminescence imager, Alpha Innotech™). Bands were analyzed according to their molecular weight.

Avidin-biotin complex DNA (ABCD) assay: cells were lysed with lysis buffer (10 mM Tris pH 8.0, 100 mM NaCl, 1 mM EDTA pH 8.0, 10% Glycerol, 0.5% NP-40, 1 mM DTT, protease-inhibitor, sonicated (6 impulses for 2 seconds), centrifuged and supernatants were incubated with buffer H (20 mM HEPES pH 7.9, 50 mM KCl, 20% Glycerol, 1 mM DTT, 0.1% NP-40), 2. µg 5'-biotinylated oligo and 20. µg herring sperm DNA for 5 min at 37° C. followed by incubation on ice for 1 h. For the competitor control (comp) a 10-fold excess of non-biotinylated oligo was added. The negative control (nc) contained cell lysate, herring sperm DNA and buffer H. Buffer H equilibrated streptavidin-agarose beads (Novagen™) were added to pulldowns and controls and then incubated for 30 min at 4° C. on a rotator. The beads were centrifuged, washed several times with buffer H, boiled in Laemmli buffer and separated by SDS-PAGE. C/EBPβ was detected by Western blot (Santa Cruz Biotech™). 5'-biotinylated and non-biotinylated oligos were ordered from MicroSynth: C/EBPβ_for: TAT TAG CCA ATA TTA GCC AAT ATT AGC CAA TAT TAG CCA (SEQ ID NO: 21), C/EBPβ_rev: TGG CTA ATA TTG GCT AAT ATT GGC TAA TAT TGG CTA ATA (SEQ ID NO: 22).

Total RNA isolation, reverse transcription and quantitative reverse transcriptase-polymerase chain reaction (qRT-PCR): Cells were homogenized and isolated with Trifast Reagent (PEQLAB Biotechnology GmbH™) following the manufacturer's instruction. cDNAs were transcribed using the High Capacity cDNA Reverse Transcription kit (Fermentas™) as indicated in the instruction manual. Expression of mRNA was quantified by real time PCR using Fast SYBR Green Master Mix (Applied Biosystems™) with the StepOne Real-Time PCR System (Applied Biosystems™) and primers in TABLE 3. Samples were assayed in duplicates dependent on the quality of their melting curves. Levels of target genes were normalized to HPRT or GAPDH and described as fold induction of unstimulated cells.

TABLE 3

| Target | Forward (5' to 3') | SEQ ID NO: | Reverse (5' to 3') | SEQ ID NO: |
|---|---|---|---|---|
| PTEN | ACA CCG CCA AAT TTA ACT GC | 23 | TAC ACC AGT CCG TCC CTT TC | 28 |
| Arginase 1 | GTG AAG AAC CCA CGG TCT GT | 24 | CTG GTT GTC AGG GGA GTG TT | 29 |

TABLE 3-continued

| Target | Forward (5' to 3') | SEQ ID NO: | Reverse (5' to 3') | SEQ ID NO: |
|---|---|---|---|---|
| Ym-1 | TTT CTC CAG TGT AGC CAT CCT T | 25 | TCT GGG TAC AAG ATC CCT GAA | 30 |
| Fizz-1 | CTG GAT TGG CAA GAA GTT CC | 26 | CCC TTC TCA TCT GCA TCT CC | 31 |
| Stabilin-1 | CCC TCC TTC TGC TCT GTG TC | 27 | CAA ACT TGG TGT GGA TGT CG | 32 |

Enzyme-linked immunoabsorbent assay (ELISA): Supernatant levels of selected cytokines secreted by lymphocytes or macrophages were measured by utilizing commercially available enzyme-linked immunosorbent assay (ELISA) (all from eBioscience) for the quantification of IL-2, IFN-γ, IL-6, IL-12/23 (p40/common subunit), and IL-17A according to the manufacturer's protocol. IL-6 and IL-12/23 were analyzed in the supernatants of macrophages 24 h after stimulation with LPS. IL-2, IFN-γ and IL-17A were measured in supernatants collected at day 4 of allogeneic mixed leucocyte reactions and of re-stimulated splenocytes and lymphocytes of Myelin oligodendrocyte glycoprotein (MOG)-immunized mice. Briefly, plates were coated with capture antibody, blocked, and diluted samples and standards were loaded for overnight incubation. Next, plates were incubated with detection antibody and then with Streptavidin-HRP (R&D Systems™) for development TMB 2—Component Microwell Peroxidase.

Induction of experimental autoimmune encephalomyelitis (EAE) and ex-vivo restimulation: Mice were assigned to 4 groups each consisting of 4 to 8 mice (see study design in TABLE 4). Briefly, for immunization mice were injected with 150 μl of an emulsion containing equal parts of $MOG_{35-55}$ (1 mg/ml, Charite Berlin™) and IFA (Sigma™) supplemented with 10 mg/ml Mycobacterium tuberculosis H37Ra (Difco™).

At time of immunization and second day after immunization 200 ng Pertussis toxin (Calbiochem™) were administered by the intraperitoneal route. For in vivo administration of purified recombinant human Arginase I mice were intravenously injected with either 10 mg/kg of body weight at days −4 and −2 prior immunization, or with 10 mg/kg or 1 mg/kg of body weight at days −4, −2 pre-, and 5 and 7 post-immunization. Mice were observed daily for clinical signs. Progression of EAE was divided in 4 clinical stages: grade 0: no signs, grade 1: complete floppy tail, grade 2: severe paraparesis, grade 3: tetraparesis, grade 4: moribund condition. For ex vivo stimulation lymphocytes and splenocytes were isolated and stimulated with 30 μg/ml of the cognate MOG-peptide for 3 days for proliferation analysis and cytokine measurements.

Mixed leucocyte reaction (MLR): Wildtype DCs were generated as described. One part of the cells was stimulated with 30 μg/ml purified recombinant human Arginase I (SEQ ID NO: 9) for 24 hrs at day 6 of differentiation, the other part acted as unstimulated control. MLR was performed on day 7 of differentiation in absence of purified recombinant human Arginase I (SEQ ID NO: 9), which was removed by accurate washing. Briefly all cells were activated and loaded with LPS (100 ng/ml, Invitrogen™) and Ovalbumin (50 μg/ml, Sigma™) for 4 hours, washed and co-cultivated with OT-II cells. Responder T cells were isolated from spleens of OT-II mice via positive magnetic cell sorting using a pan T-cell isolation kit (Miltenyi Biotec™), labeled with 7 μM $CFSE/1\times10^7$ cells according to the manufacturer's instructions (Sigma™). DCs (100 000 cells) were washed and plated on a 48-well along with responder T-cells (500 000 cells) in 500 μl total volume. On day 3 of the co-culture cells were harvested, fixed and subjected to intracellular staining. For proliferation cells were harvested in TruCount tubes and analyzed for CFSE dilution.

CD4* T cell phenotyping by flow cytometry: Cells were isolated from MLR in vitro cultures on day 3 and re-stimulated with PMA/ionomycin (Sigma™) together with Golgi-Stop (BD Biosciences™) and analyzed for intracellular cytokines. The following antibodies were used for cytokine staining: Anti-mouse CD4—PerCP (clone RM4-5, BD Pharmingen™), CD25—PE-Cy7 (clone PC61.5), IL-2—eFlour® 450 (clone JES6-5H4), IL-10—Alexa Flour® 647 (clone JES5-16E3), IL-17A—PE-Cy7 (clone 17B7), IFNγ-PE (clone XMG1.2, all from eBioscience™). Cell acquisition and data analysis was performed on a LSR 2 flow cytometer (BD Biosciences™) and FlowJo™ software Version 10.0 (Treestar™).

Statistics: Statistical significance of data was calculated by use of an unpaired two-tailed Student's t-test. Two way ANOVA analyses were used to analyze two groups over time. Statistical analysis was performed using GraphPad Prism software (GraphPad™ Software, La Jolla, USA). Results are presented as the mean+/−standard deviation. P-values <0.05 were considered statistically significant (p-values were expressed as follows: * p<0.05,  p<0.01, * p<0.001).

Results.

To better characterize the biological crosstalk between Arginase I expression and the activation of immune cells the expression profile of Arginase I mRNA under different conditions was investigated. We identified increased levels of Arginase I mRNA in a genome wide screen of PTEN deficient dendritic cells and littermate derived control cells. FIG. 1 illustrates the upregulation of Arginase I by LPS in macrophages. In FIG. 1, Thioglycollate elicited peritoneal macrophages (tPMs) were induced by E. coli O111:B4 LPS for 8 h and 24 h. Arginase I expression was increased on mRNA level 8 hours after LPS stimulation (FIG. 1, Panel A) and on protein level within 24 hours post LPS induction (FIG. 1, Panel B). These time points were selected for further analysis of LPS-mediated Arginase I expression in dependence of the PI3K/PTEN signaling pathway in macrophages.

Figure 2:
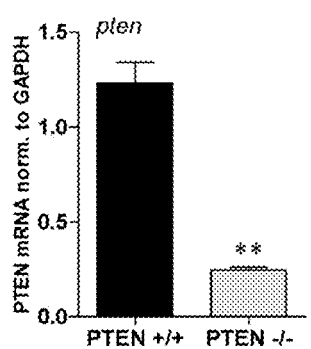
FIG. 2 illustrates an increase in Arginase I expression accompanied by loss of PTEN.
Figure 2:
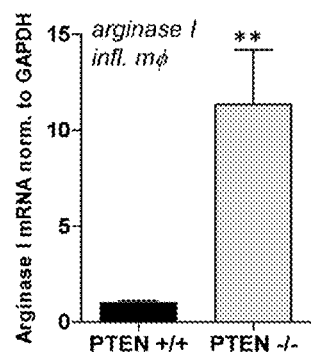
Figure 2:
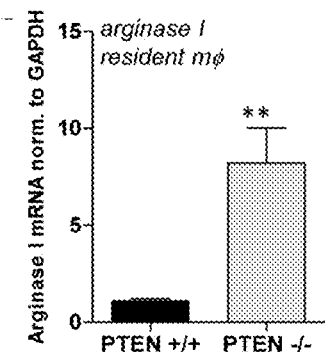
Figure 2:
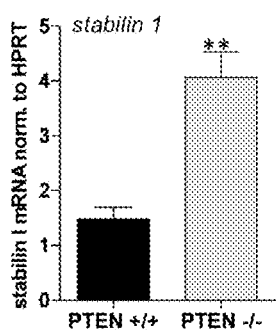
Figure 2:
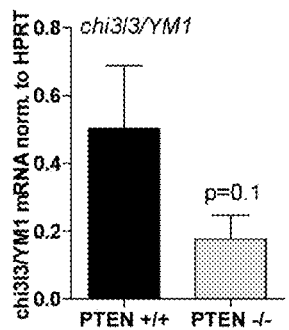
Figure 2:
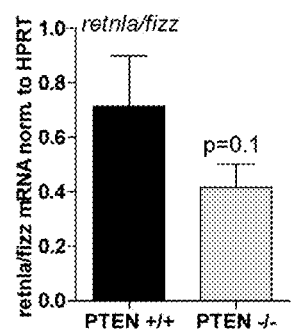
Figure 2:
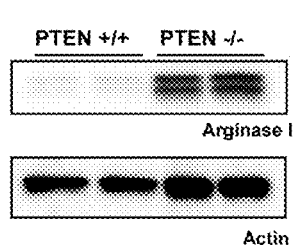
Figure 2:
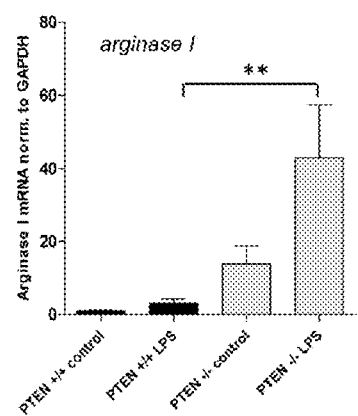
Figure 2:
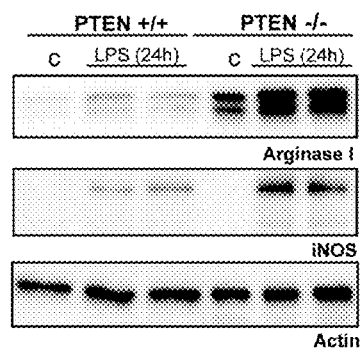
Figure 2:
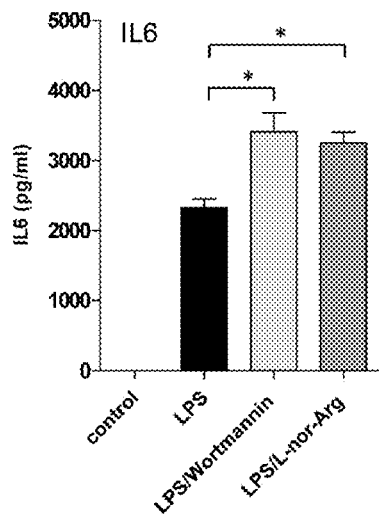
Figure 2:
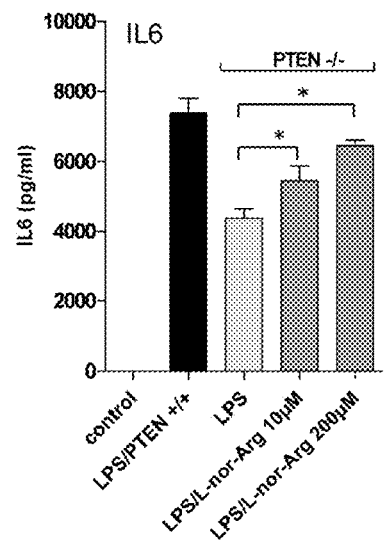

High expression of Arginase I in PTEN deficient macrophages suggested that one or more components of the signal transduction pathways involved in innate immunity could regulate, or be regulated, by Arginase I expression. FIG. 2 illustrates an increase in Arginase I expression accompanied by loss of PTEN. FIG. 2, panel A illustrates the marked upregulation of Arginase I mRNA in unstimulated, naïve PTEN deficient peritoneal macrophages. These experiments were performed in resident peritoneal macrophages and in sterile inflammation induced peritoneal macrophages (FIG. 2, panels B and C). In accordance with upregulated Arginase I mRNA expression, increased mRNA levels for stabilin 1 in unstimulated PTEN$^{-/-}$ tPMs (FIG. 2, panel D), and reduced expression of YM1 and FIZZ (FIG. 2, panels E and F) was observed. The increase in protein expression of Arginase I in PTEN negative cells was also confirmed.

To further evaluate the function of Arginase I in response to LPS induced signaling events the expression levels of Arginase I on mRNA and protein levels was analyzed 24 hours post LPS activation (FIG. 2, panels H and I). Wildtype macrophages harvested from littermate control mice showed slight upregulation of Arginase I. Notably the expression of the prominent M1 marker iNOS was also enhanced in LPS stimulated PTEN deficient macrophages.

The following experiments were conducted to further study the mechanisms of a broader immune-regulatory function of Arginase I in immune cells: 1) wildtype macrophages were stimulated with LPS; 2) stimulation was inhibited with the fungal PI3K inhibitor wortmannin, which has been reported to enhance cytokine synthesis upon LPS induction in vitro and in vivo (Guha, M., and N. Mackman. 2002. The phosphatidylinositol 3-kinase-Akt pathway limits lipopolysaccharide activation of signaling pathways and expression of inflammatory mediators in human monocytic cells. *J. Biol. Chem.* 277: 32124-32132); Schabbauer, G. et al. 2004. PI3K-Akt pathway suppresses coagulation and inflammation in endotoxemic mice. *Arterioscler. Thromb. Vasc. Biol.* 24: 1963-1969); and with 3) the Arginase inhibitor N-hydroxy-nor-L-arginine (L-nor-Arg). Inhibition of Arginase I significantly enhanced IL-6 production in macrophages (FIG. 2, panel J). The effects of the Arginase-specific inhibitor on the diminished cytokine production of PTEN$^{-/-}$ macrophages was also evaluated as compared to wildtype macrophages. Indeed a significant, but only partial, restoration of the wildtype IL-6 production was found upon treatment with L-nor-Arg in PTEN deficient tPMs (FIG. 2, panel K).

The pharmacologic Arginase inhibition and the ablation of the anti-inflammatory phenotype in PTEN deficient Arginase overexpressing tPMs support the claim that Arginase I contributes to the PI3K mediated modulation of inflammatory responses.

PTEN deletion in macrophages upregulates the transcription factor C/EBPβ, which is crucial for Arginase I promoter activation. To elucidate the molecular mechanism responsible for the PTEN-mediated gene regulation of Arginase I, several potential candidate transcription factors (TF) were analyzed. The most prominent regulator of Arginase I is STAT 6, which is activated by IL-4 and/or IL-13 in macrophages (Gordon, S., and F. O. Martinez. 2010. Alternative activation of macrophages: mechanism and functions. *Immunity* 32: 593-604). Unstimulated tPMs, either PTEN deficient cells or wild type cells derived from littermate control animals, did not show any overt changes in STAT6 total protein content or activated STAT6 as measured by phospho-specific STAT6 antibodies. Another candidate transcription factor is C/EBPβ, which has been shown to contribute to pattern recognition receptor-mediated regulation of Arginase I (El Kasmi, K. C. et al. 2008. Toll-like receptor-induced arginase 1 in macrophages thwarts effective immunity against intracellular pathogens. *Nat. Immunol.* 9: 1399-1406).

Figure 3:
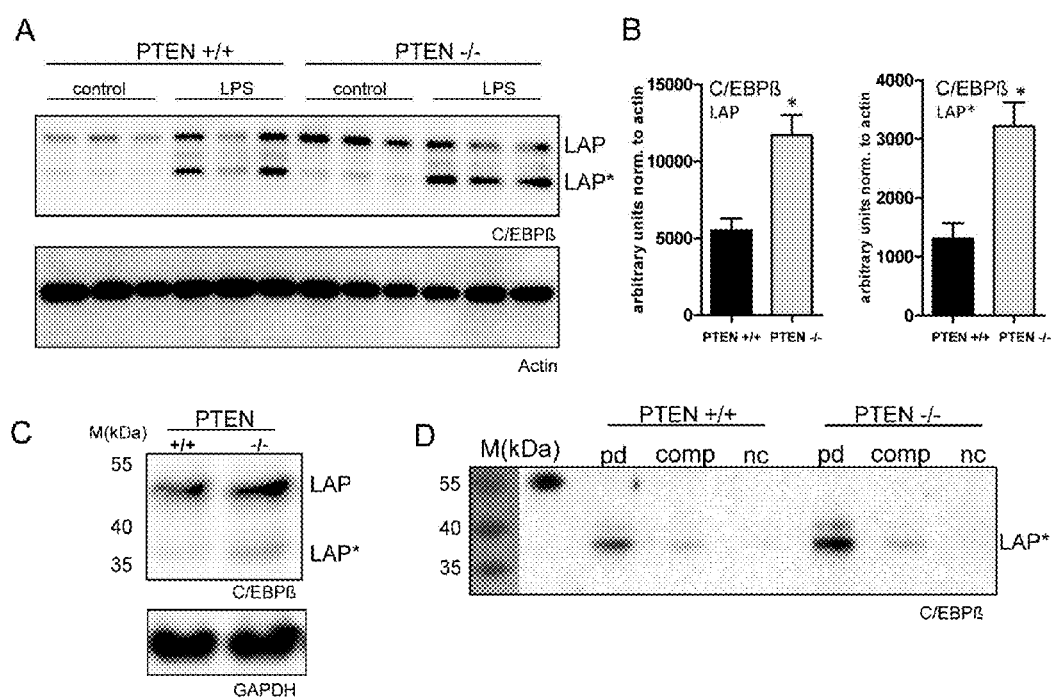
FIG. 3 illustrates the function of C/EBPβ in PTEN deficient macrophages.

To characterize mechanisms of modulating Arginase I expression by modulating upstream factors, the regulation of C/EBPβ by PTEN, and subsequent constitutive upregulation of Arginase I by C/EBPβ were analyzed. FIG. 3 illustrates the function of C/EBPβ in PTEN deficient macrophages. FIG. 3, panel A illustrates the upregulation of C/EBPβ protein in PTEN deficient tPMs. FIG. 3, panel B illustrates that the same result was obtained for two isoforms of C/EBPβ, LAP and LAP*. Further induction of the transcription factor was observed within 8 hours post LPS induction. However we could not identify an additional upregulation of C/EBPβ by PTEN deletion upon TLR4 activation at least at the time point we have evaluated (8 h). Since maximal Arginase I expression is observed 24 h after LPS induction, we cannot exclude C/EBPβ differential expression might occur earlier in activated PTEN deficient macrophages.

Due to the fact that C/EBPβ is a transcription factor acting on specific DNA elements, the binding of C/EBPβ to the Arginase enhancer element containing a number of different TF consensus binding sites was investigated. An avidin biotin coupled DNA (ABCD) binding assay was used to evaluate C/EBPβ DNA binding properties using biotinylated oligos spanning the C/EBPβ consensus site within the Arginase enhancer 3.8 kb upstream of the transcription start site. The suitability of this experimental system was tested in HEK cells overexpressing C/EBPβ. Overexpressed C/EBPβ efficiently bound the oligo which could be precipitated together with the transcription factor, in particular the LAP* isoform, bound to it. Next the effects of PTEN deficiency on C/EBPβ DNA binding in macrophages was analyzed. First the presence of C/EBPβ in the lysates used for the ABCD binding assays was verified. Equal input for the ABCD assay was determined by reproving against GAPDH (FIG. 3, panel C). Analysis of TF binding to the Arginase oligo suggests that in addition to increased protein levels enhanced binding of C/EBPβ occurred. LAP* was identified as the dominant isoform binding to the Arginase enhancer oligo (FIG. 3, panel D).

These data suggest a potential mechanism for PI3K/PTEN regulation of Arginase I expression via C/EBPβ.

Example 2. Extracellular Activity of Arginase I

To study the cellular site of action of Arginase I, supernatants (SN) of peritoneal macrophages were analyzed. Unexpectedly, Arginase I was released into the extracellular space. This is in contrast to Arginase I counterpart iNOS.

Figure 4:
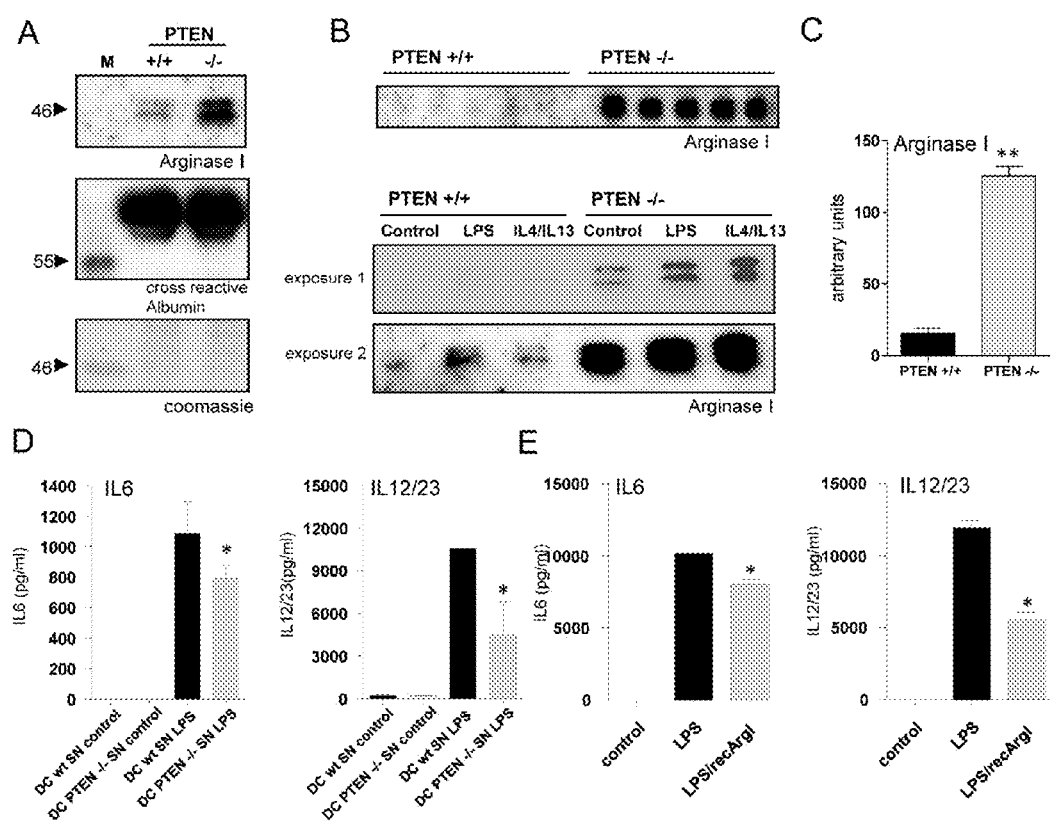
FIG. 4 illustrates that constitutive activation of PI3K promotes Arginase I expression and release into the extracellular space.

To further evaluate the role of Arginase I in cytokine production and the potential of antigen presenting cells to polarize T-cells, media conditioned to wildtype bone marrow derived GM-CSF differentiated dendritic cells was transferred and their inflammatory response to LPS was analyzed. FIG. 4 illustrates that constitutive activation of PI3K promotes Arginase I expression and release into the extracellular space. Surprisingly, the data indicates a downregulation in the protein levels of the T-cell polarizing cytokines IL-6 and IL-12 p40, the common subunit of IL-12 and IL-23 (further on denoted as IL-12/23), (FIG. 4, panel D). Next we attempted to mimic a physiological environment with high expression of Arginase I conditioned media from PTEN deficient macrophages, using purified recombinant human Arginase I (recArgI). In order to do so, dendritic cells stimulated by LPS were pre-incubated with purified recombinant human Arginase I. Reduced expression levels of IL-6 and IL-12/23 similar to the treatment with conditioned media was detected. The decrease in expression was more pronounced on IL-12/23 expression as compared to IL-6 (FIG. 4, panel E).

To further characterize the biological crosstalk between Arginase I expression and PTEN expression the expression of Arginase I and IL-4/IL-13 in PTEN deficient cells was measured. Deficiency of PTEN leads to highly increased expression levels of Arginase I, even in unstimulated peritoneal macrophages tPMs (FIG. 4, panel A). These findings were surprising and unexpected. To quantify the results, macrophages derived from 5 wildtype littermates and PTEN$^{-/-}$ animals were analyzed. A greater than 10-fold increase in extracellular Arginase I expression was detected in PTEN$^{-/-}$ macrophages (FIG. 4, panels B and C). In addition, we evaluated Arginase I secretion in response to LPS and in parallel to combined activation by IL-4 and IL-13. In both cases we observed increased secretion in PTEN deficient macrophages, which was also seen to a limited extent in wildtype cells (FIG. 4, panels B bottom).

The result indicates that Arginase I presence in the extracellular environment of macrophages might exhibit anti-inflammatory properties in a paracrine fashion.

Example 3. Free Arginase I Potently Inhibits T-Cell Polarization

To analyze the effects of recombinant human Arginase I on antigen presentation and T-cell polarizing properties, bone marrow derived GM-CSF differentiated wildtype dendritic cells were pre-conditioned with recombinant Arginase I overnight before the cells were loaded with Ovalbumin (Ova) and stimulated with LPS. To avoid potential effects on T-cells, recArgI was removed from the DCs by multiple washing steps before cultivating them together with isolated OT-II T-cells in a ratio 5:1. Treatment of dendritic cells with recombinant Arginase I in a concentration of 30 μg/ml did not alter the surface expression of prototypic DC activation markers CD80 and MHCII, as measured by flow cytometry.

Figure 5:
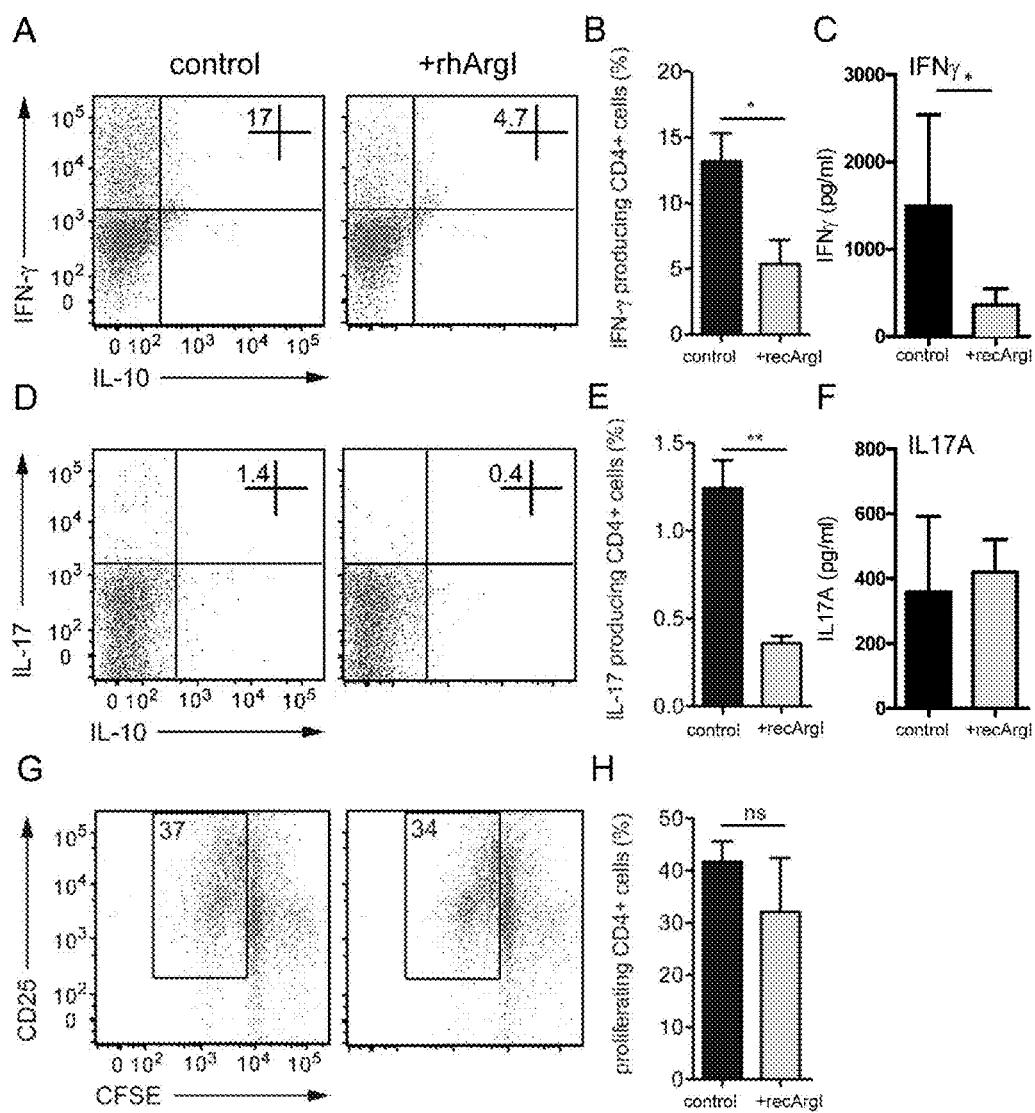
FIG. 5 illustrates inhibition of T-cell polarization by Arginase I.

The results of the MLR were evaluated after 3 days of co-culture of DCs and T-cells. FIG. 5 illustrates inhibition of T-cell polarization by Arginase I. We observed a significant reduction of Th1 and Th17 signature cytokines IFNγ (FIG. 5, panels A and B) and IL17A (FIG. 5, panels D and E) expressing CD4$^+$ T-cells. We note that IL-17 producing cells were present, but in low numbers. Analyzes of T-cell cytokines that were secreted during the MLR after LPS/Ova priming reveal significant differences in the release of IFNγ, whereas IL-17A was not significantly different (FIG. 5, panels C and F). Proliferation as measured by CFSE dilution in dividing T-cells was evaluated. However we did not find significant changes in the presence of recombinant Arginase I (FIG. 5, panels G and H). The data suggests that extracellular Arginase I in the presence of antigen-presenting cells ameliorates T-cell priming, thereby reducing the capacity to polarize preferentially in Th1 cells.

To further corroborate this hypothesis, the ability of recombinant Arginase I to inhibit T cell polarization in vivo in a clinically relevant model for T-cell mediated autoimmune disease was characterized.

Example 4. Recombinant Arginase I in the Treatment of Multiple Sclerosis

Autoimmune diseases are characterized by a deregulated immune system. The experimental autoimmune encephalomyelitis (EAE) mouse model is an art recognized animal model of multiple sclerosis. To study the ability of a recombinant Arginase I to module an immune response, the response of a mouse model for multiple sclerosis treated with a purified Arginase was characterized. The EAE mouse reflects some, but not all, features of the human autoimmune pathology (Lassmann, H., and H. J. van. 2011. The molecular basis of neurodegeneration in multiple sclerosis. *FEBS Lett.* 585: 3715-3723). EAE was induced in wildtype mice by immunization with MOG$_{35-55}$ peptide in CFA (Lassmann, H., and H. J. van. 2011. The molecular basis of neurodegeneration in multiple sclerosis. *FEBS Lett.* 585: 3715-3723). In addition pertussis toxin was administered.

The potential efficacy of recombinant Arginase I in ameliorating disease progression was characterized as follows: to determine a time-frame of treatment, while antigen presentation and T-cell polarization were still ongoing, Arginase was administered in two different concentrations before and shortly after immunization as described in TABLE 4.

TABLE 4

| | days (pre- or post-immunization) | | | | | | | | | | | | | | | | | | | | | |
|---|---|---|---|---|---|---|---|---|---|---|---|---|---|---|---|---|---|---|---|---|---|---|
| | -4 | -2 | 0 | 1 | 2 | 3 | 4 | 5 | 6 | 7 | 8 | 9 | 10 | 11 | 12 | 13 | 14 | 15 | 16 | 17 |
| Control: | | | | | | | | | | No treatment | | | | | | | | | | |
| Group 1: recArgI 10 mg/kg | + | + | | | | | | + | | + | | | | | | | | | | |
| Group 2: recArgI 1 mg/kg | + | + | | | | | | + | | + | | | | | | | | | | |
| Group 3: recArgI pre 10 mg/kg | + | + | | | | | | | | | | | | | | | | | | |

Figure 6:
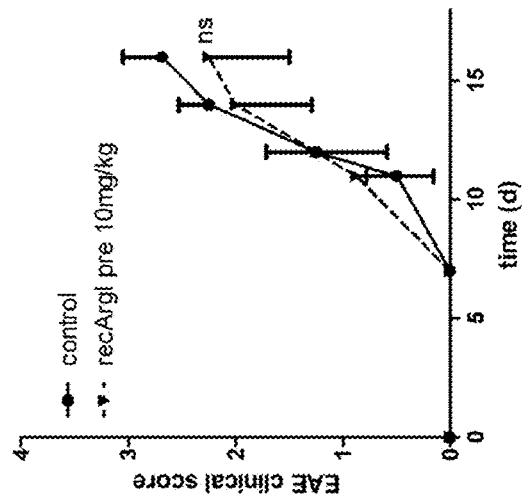
FIG. 6 illustrates results of a treatment of an art recognized model of multiple sclerosis, the experimental autoimmune encephalomyelitis (EAE) mouse, with recombinant human Arginase I.
Figure 6:
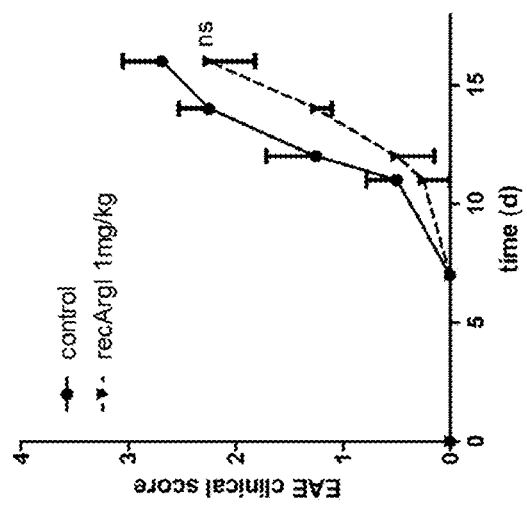
Figure 6:
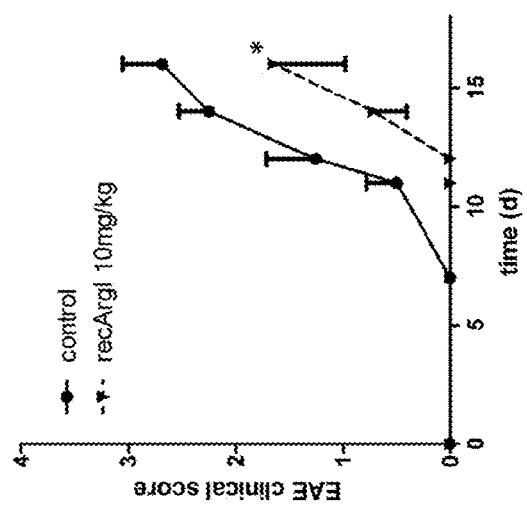
Figure 6:
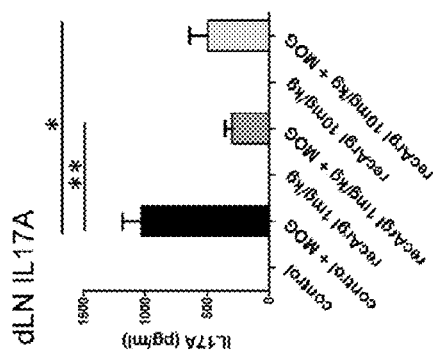
Figure 6:
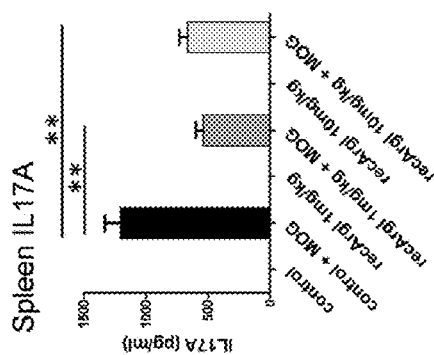
Figure 6:
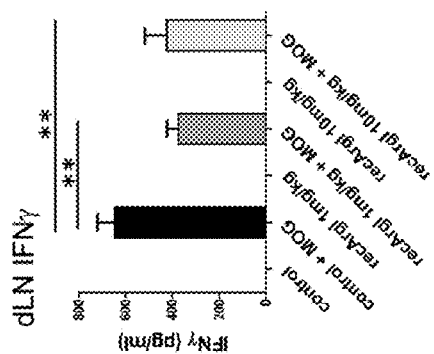
Figure 6:
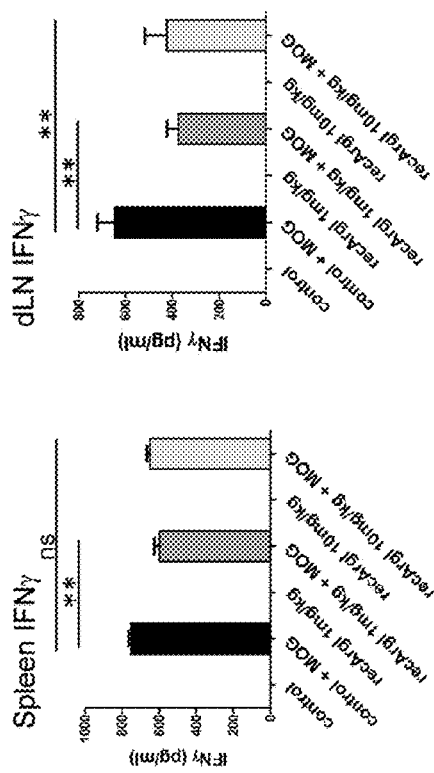

FIG. 6 illustrates results of a treatment of experimental autoimmune encephalomyelitis (EAE) with recombinant human Arginase I. The control group developed visible signs of EAE after 12 days, further increasing until day 17. Pretreatment with recombinant Arginase I (10 mg/kg) did not have any effect on the course of disease (FIG. 6, panel C). Pre- and post-treatment with recombinant Arginase I (10 mg/kg) in contrast was characterized by a significant reduction in the onset as well as the magnitude of the disease (FIG. 6, panel A). In the same experimental setup, a minimum therapeutically effective dose of a pegylated Arginase I (SEQ ID NO: 9) was tested (1 mg/kg). Treatment delayed the onset of disease, but disease progression and severity was not significantly inhibited by the treatment with the lower dose of the pegylated Arginase I (FIG. 6, panel B).

To analyze the MOG-specific T-cell response on a molecular level we harvested spleens and the draining lymph node (inguinal) and restimulated the splenocytes and the lymph node cells, derived from recombinant human Arginase-treated and control EAE mice, in vitro with the MOG$_{35-55}$ peptide. Restimulation of cells without further activation by exogenous stimuli led to a marked increase in IFNγ and IL-17A secretion into the supernatants (see control vs. control+MOG in FIG. 6, panels D-G). Interestingly we found highly significant differences for reduced IFNγ (FIG. 6, panels D and E) and IL-17A (FIG. 6, panels F and G) levels in both pre- and post-treatment groups (1 mg/kg as well as 10 mg/kg recombinant Arginase I) in particular in the draining lymph node. These data suggest that recombinant Arginase I treatment in the phase of antigen presentation at least at the higher concentration efficiently blunts EAE pathology in mice through a diminished capacity of CD4+ T cells to produce cytokines IFNγ and IL-17A indispensable for the development of EAE.

Example 5. Recombinant Arginase I in the Treatment of Rheumatoid Arthritis

Arthritis is an autoimmune condition associated with varied levels of pain, swelling, joint stiffness and sometimes a constant ache around the joint(s). There are over 100 different forms of arthritis, including rheumatoid arthritis, psoriatic arthritis, and related autoimmune diseases. Septic arthritis is caused by joint infection.

Figure 7:
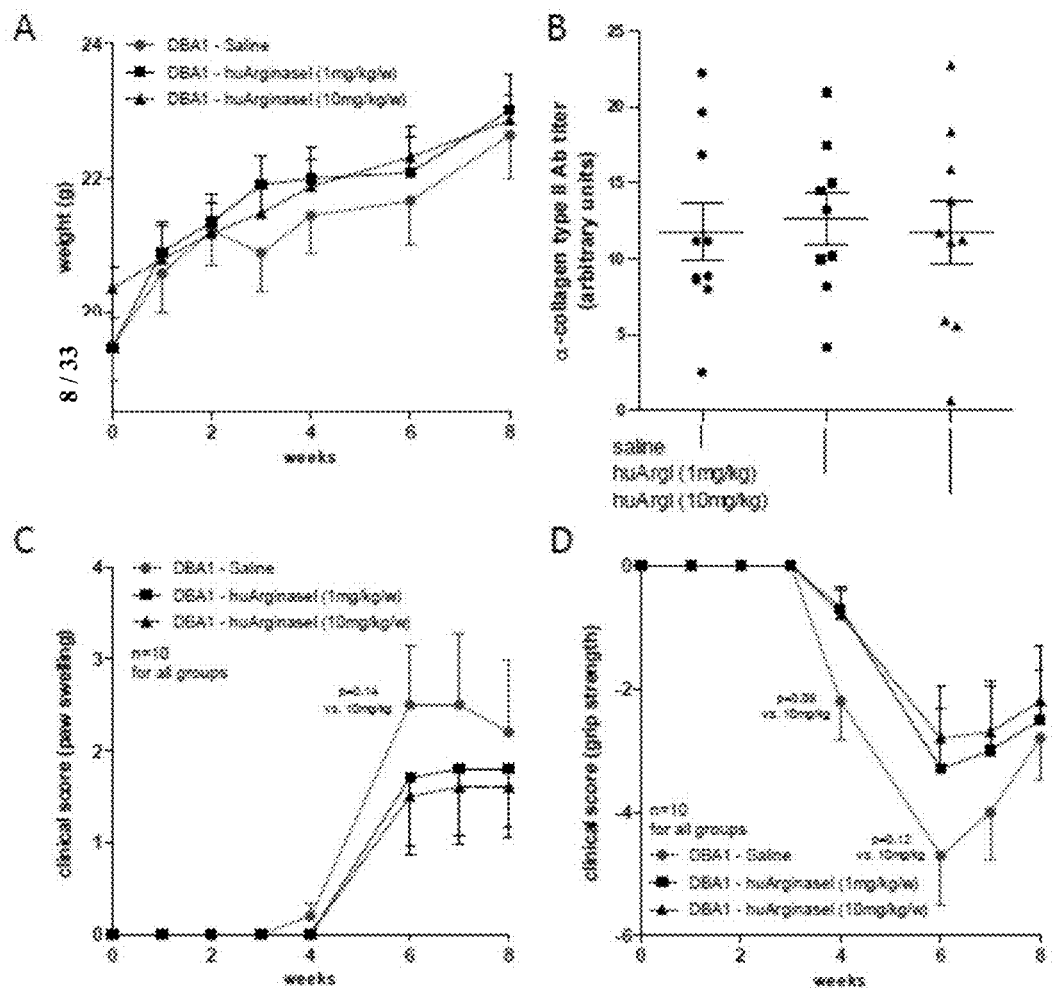
FIG. 7 depicts graphs measuring various clinical parameters of arthritic mice treated with recombinant human Arginase I.
Figure 8:
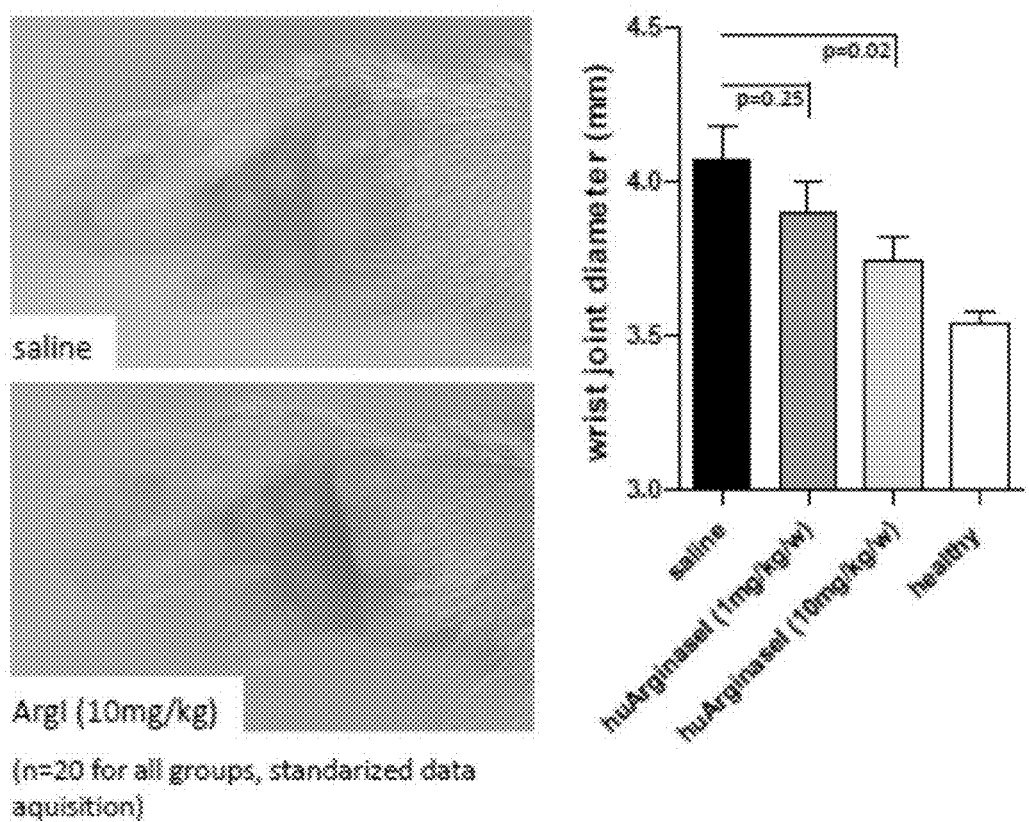
FIG. 8 illustrates the reduction of paw swelling in arthritic mice treated with recombinant human Arginase I.

The major complaint by individuals who have arthritis is joint pain. Pain is often a constant and may be localized to the joint affected. The pain from arthritis is due to inflammation that occurs around the joint, damage to the joint from disease, daily wear and tear of joint, muscle strains caused by inflammation. To evaluate the role of a recombinant human Arginase I in the treatment of arthritis we measured several clinical parameters of arthritic mice treated with the recombinant protein. FIG. 7 depicts graphs measuring various clinical parameters of arthritic mice treated with recombinant human Arginase I. FIG. 7, panel A illustrates the percentage variation in weigh of mice receiving either saline, 1 mg/kg/w or 10 mg/kg/w of recombinant human Arginase I. FIG. 7, panel B is a graph plotting the ca-collagen type II antibody titer (arbitrary units) of mice receiving the treatments previously described. FIG. 7, panels C and D are the measurements of two different clinical parameters of the same mice described above, namely, paw swelling and grip strength. The results suggest that weekly treatment of arthritic mice with recombinant human Arginase I ameliorate the disease but do not prevent disease progression. FIG. 8 is a photograph illustrating the reduction of paw swelling in arthritic mice with human recombinant human Arginase I. FIG. 8, panel A illustrates the swelling of an arthritic mice that received treatment with saline only. FIG. 8, panel B illustrates the swelling of an arthritic mice that received treatment with 10 mg/kg of pegylated human recombinant Arginase I. The statistical quantitation of the data suggests that treatment of arthritic mice with both 1 mg/kg and 10 mg/kg of recombinant human Arginase I reduces paw swelling, as measured by the decrease in wrist joint diameter.

Figure 9:
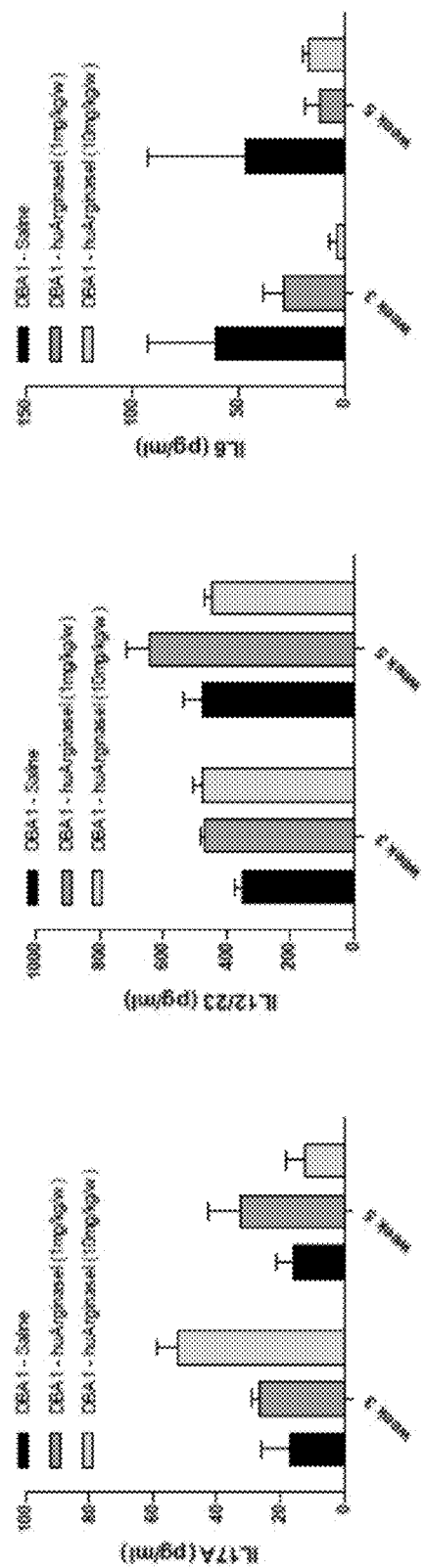
FIG. 9 illustrates the reduction of systemic release of Interleukin 6 (IL-6) in arthritic mice treated with human recombinant human Arginase I.
Figure 10:
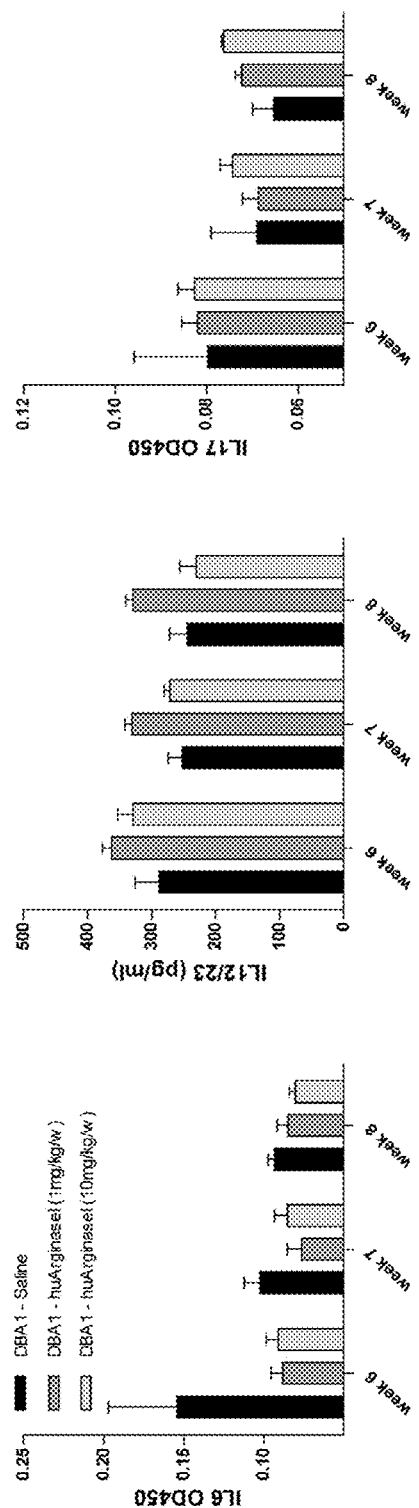
FIG. 10 depicts graphs measuring the expression of pro-inflammatory cytokines post collagen immunization.
Figure 11:
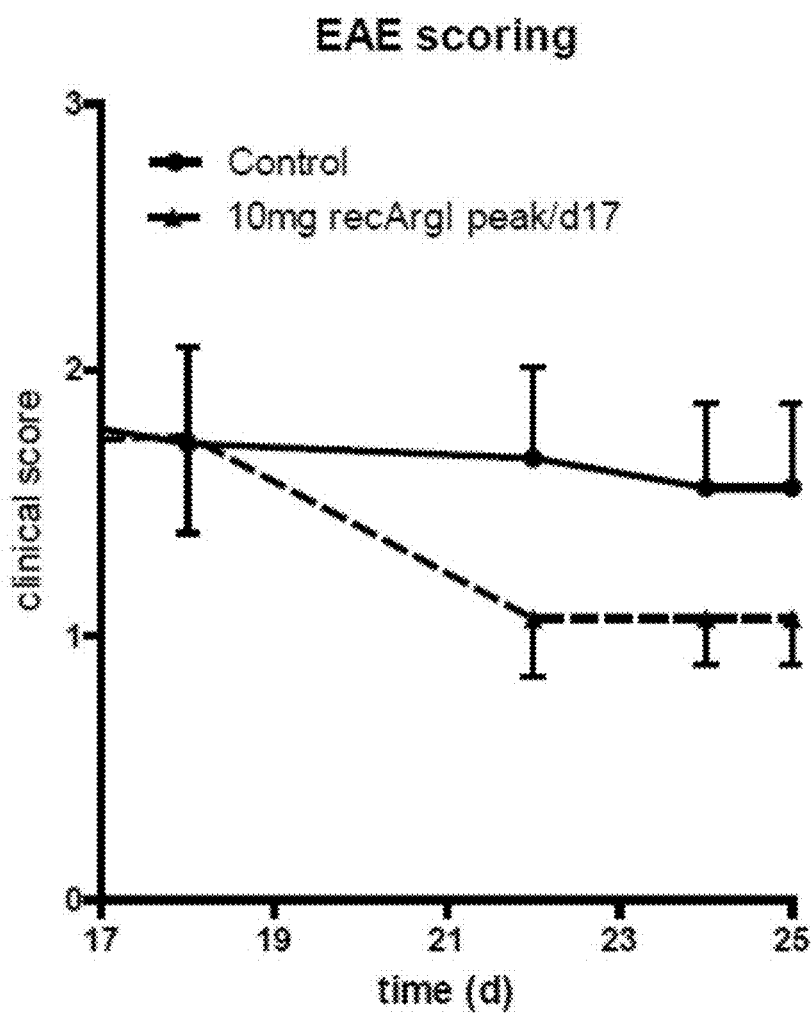
FIG. 11 is a graph depicting the clinical score of a mouse model of experimental autoimmune encephalomyelitis (EAE) treated with recombinant human Arginase I.

FIG. 9 corresponds to graphs illustrating the quantitation of different cytokines in arthritic mice. The animals in FIGS. 9 and 10 were treated with collagen immunization, which promoted arthritis in the mice. FIG. 9 panels A and B indicate that only a modest decrease in the levels of IL17A and IL12/23 is observed in the mice treated with recombinant human Arginase I. FIG. 9 panel C illustrates the reduction of systemic release of the inflammatory cytokine Interleukin 6 (IL-6) in arthritic mice treated with a recombinant human Arginase I. FIG. 10 panels A-C indicate that the levels of pro-inflammatory cytokines are not changed in collagen induced arthritis (CIA) in DBA mice. As a comparison to the arthritis treatment, FIG. 11 illustrates the clinical score of a mouse model of experimental autoimmune encephalomyelitis (EAE) treated with human recombinant human Arginase I (for further details, see Example 1). The results indicate that a purified recombinant human Arginase I can effectively treat conditions of the immune system.

Figure 12:
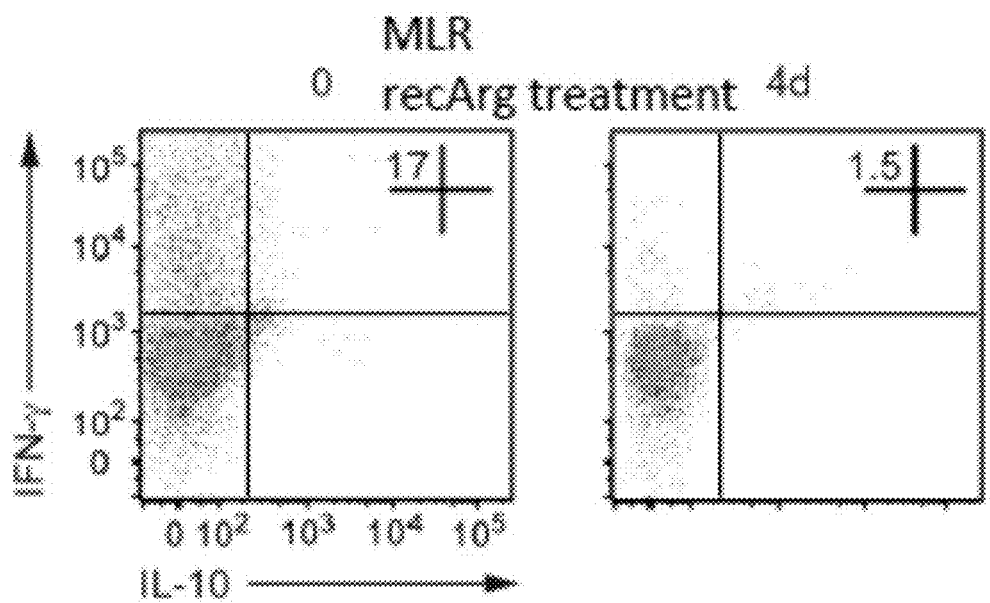
FIG. 12 depicts the fluorescence-activated cell sorting analysis of populations of immune cells in EAE mice treated with recombinant human Arginase I.
Figure 12:
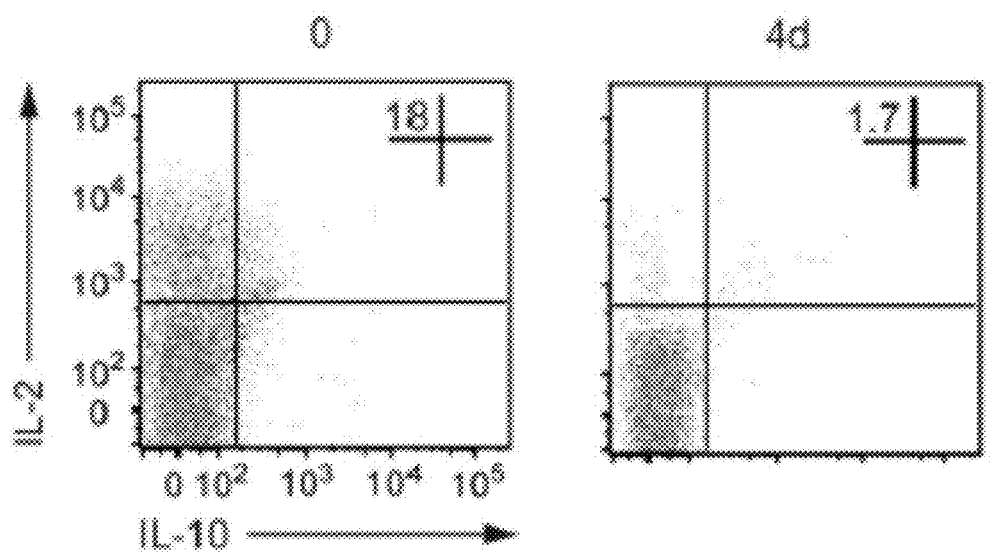
Figure 12:
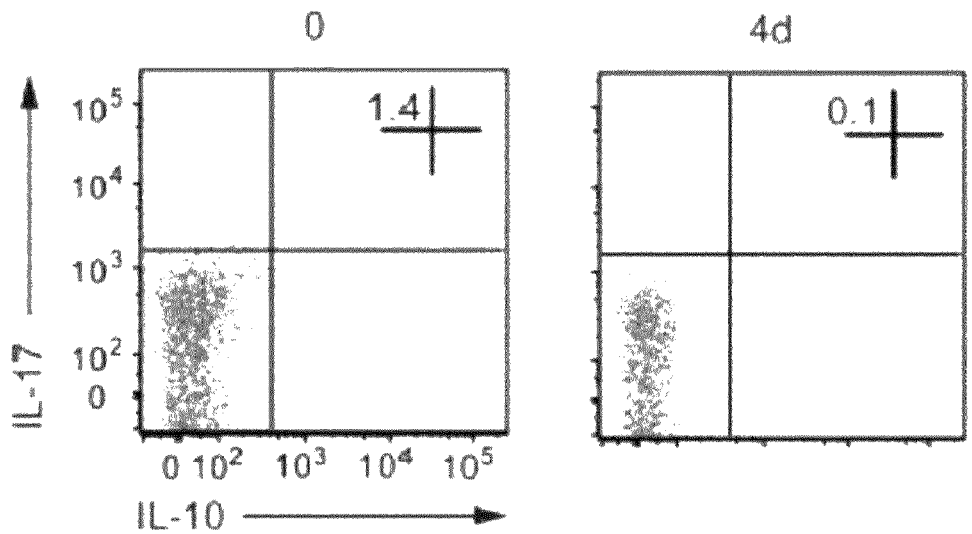
Figure 12:
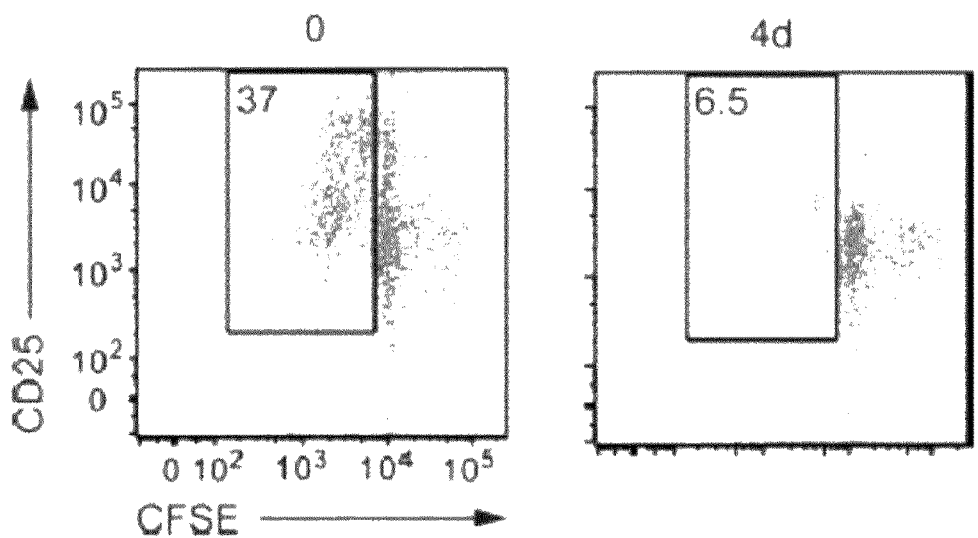
Figure 13:
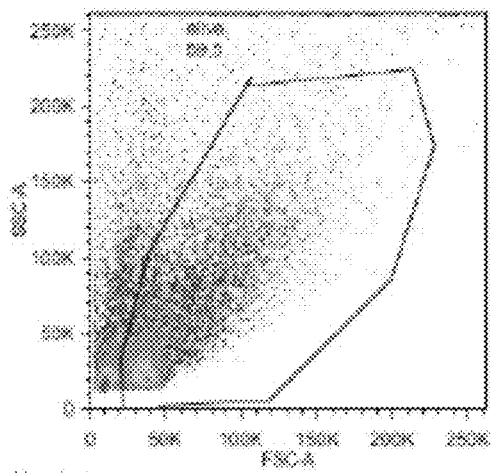
FIG. 13 depicts the results of fluorescence-activated cell sorting experiments indicating that treatment with recombinant human Arginase I prevents T-cell proliferation.
Figure 13:
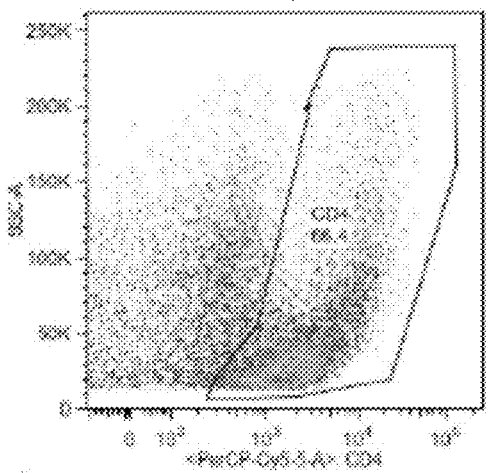
Figure 13:
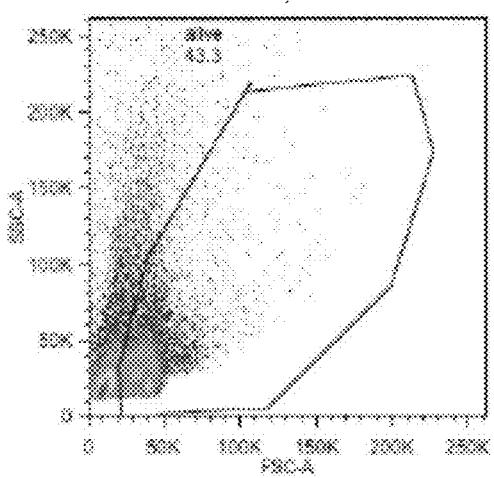
Figure 13:
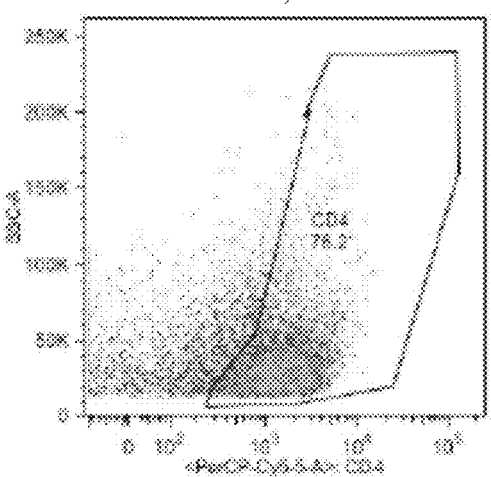
Figure 13:
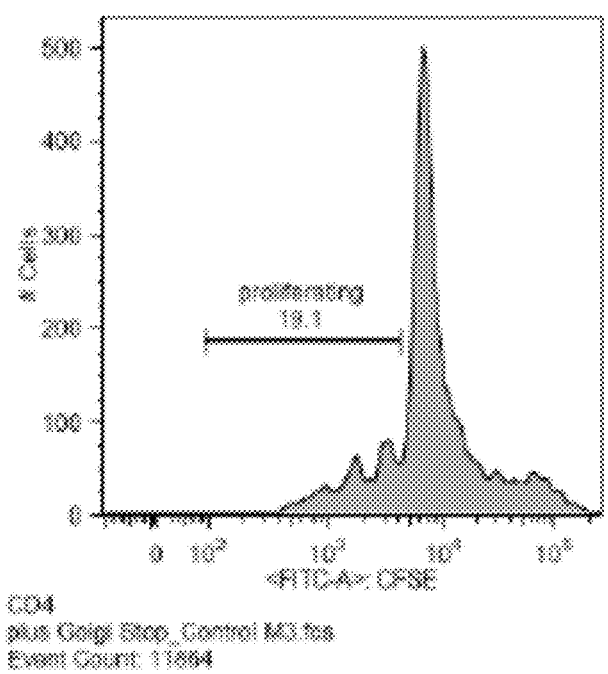
Figure 13:
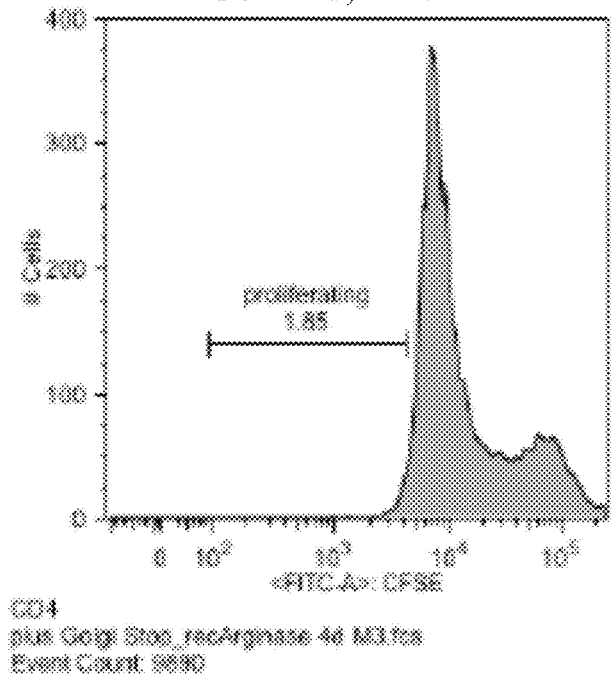

To test the effects of recombinant Arginase in an in vivo setting involving antigen presentation, cytokine release and T-cell polarization, fluorescent-activated cell sorting experiments were used to characterize populations of immune cells in EAE mice. Arginase treatment was performed after the disease progressed to a phenotype of partial hind limb paralysis and indicated that treatment with at least the recombinant arginase of SEQ ID NO. 9 could promote faster recovery. FIG. 12 depicts the fluorescence-activated cell sorting analysis of populations of immune cells in EAE mice treated with recombinant human Arginase I (FIG. 12, PANELS A-D). FIG. 13 depicts the results of fluorescence-activated cell sorting experiments indicating that treatment with recombinant human Arginase I prevents T-cell proliferation (FIG. 13, PANELS A-F).

Example 6. Pegylated Formulations of Recombinant Human Arginase I

In vitro and in vivo experiments point out the immune-modulatory properties of extracellular Arginase I. To formulate, evaluate, and optimize pharmaceutical compositions for the administration of recombinant human Arginase I in vivo several experiments characterizing the pegylation of recombinant Arginase I were conducted. Pegylation is the process of covalent attachment of polyethylene glycol (PEG) polymer chains to another molecule. The covalent attachment of PEG to a drug or therapeutic protein can reduce the immunogenicity and antigenicity of the recombinant Arginase I from the subject's immune system, and increase the hydrodynamic size of the recombinant Arginase, which can prolong the half-life of a pegylated recombinant human Arginase I in vivo.

FIG. 14 is a schematic of a process utilized for optimizing a pharmaceutical composition comprising a recombinant human Arginase I. Three different methods of covalent attachment of different sizes of PEG molecules to recombinant Arginase I molecules were tested. For illustrative purposes, FIG. 14 describes the attachment of distinct PEG molecules to SEQ ID NO: 1 by distinct methods, but it should be understood that the pegylation optimization strategy applies to any one of SEQ ID NOS. 1-16. FIG. 14 illustrates three methods of covalently attaching a PEG polymer chains to, for example SEQ ID No. 1, namely amine —NH$_2$ conjugation, cysteine (—SH) conjugation, and N-terminal modification. The pegylation of various mutant recombinant human Arginases at specific residues was optimized as described in FIG. 14.

Figure 15:
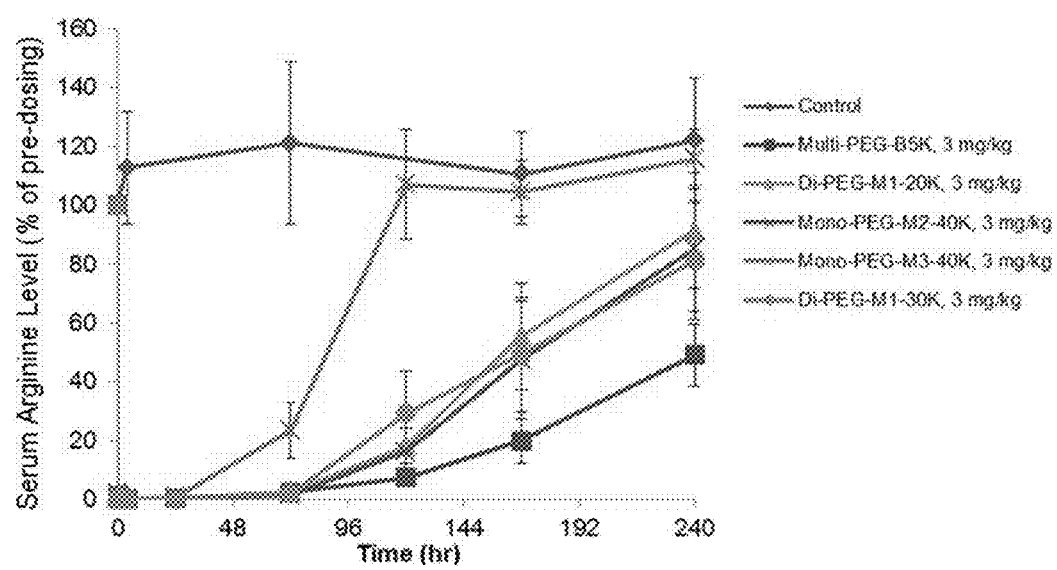
FIG. 15 is a graph illustrating the serum arginine depletion by a purified recombinant human Arginase I pegylated with mPEG-MAL (—SH modification).

TABLE 5 summarizes the pegylation of various mutant recombinant human Arginases by cysteine (—SH) conjugation. FIG. 15 shows the levels of serum Arginine depletion in Sprague Dawley rats obtained with the pegylated Arginases described in TABLE 5 with a single intravenous dose of 3 mg/kg.

TABLE 5

| SEQ ID NO. | MAL-PEG MW | Pegylated Products | Pegylation Site | No. of PEG |
|---|---|---|---|---|
| SEQ ID NO: 2 | 20K | M1-20K (45) | Cys45 | 1 |
| | | M1-20K (168) | Cys168 | 1 |
| | | M1-20K (45/168) | Cys45 & Cys168 | 2 |
| SEQ ID NO: 2 | 30K | M1-30K (45) | Cys45 | 1 |
| | | M1-30K (168) | Cys168 | 1 |
| | | M1-30K (45/168) | Cys45 & Cys168 | 2 |
| SEQ ID NO: 5 | 40K | M2-40K (45) | Cys45 | 1 |
| SEQ ID NO: 6 | 40K | M3-40K (168) | Cys168 | 1 |

The half-life $T_{1/2}$, peak plasma concentration after drug administration $C_{max}$, and the integral of the concentration-time curve after administration of a single dose AUC of pegylated SEQ ID NO. 2, SEQ ID NO. 5, SEQ ID NO. 6, and SEQ ID NO. 9. —SH modified pegylated arginases in six different rats is shown in TABLE 6. Each measurement was obtained after administration of a single intravenous dose of 3 mg/kg (mean±SD; n=6).

TABLE 6

| Pegylated Products | $T_{1/2}$ (hours) | $C_{max}$ (μg/mL) | $AUC_{last}$ (h * μg/mL) | $AUG_{0-\infty}$ (h * μg/mL) |
|---|---|---|---|---|
| M1-20K (45/168) | 28.8 ± 4.5 | 41.5 ± 9.5 | 1599.2 ± 183.8 | 1614.8 ± 188.8 |
| M1-30K (45/168) | 28.4 ± 8.4 | 32.4 ± 3.1 | 1113.6 ± 116.8 | 1192.9 ± 121.2 |
| M2-40K (45) | 27.5 ± 3.1 | 45.2 ± 5.1 | 2063.9 ± 161.5 | 2080.5 ± 163.8 |
| M3-40K (168) | 15.1 ± 0.6 | 82.7 ± 32.0 | 524.6 ± 32.6 | 541.1 ± 34.2 |
| SEQ ID NO: 9 | 31.5 ± 5.3 | 48.9 ± 12.6 | 1626.2 ± 631.8 | 1675.6 ± 644.7 |

Figure 16:
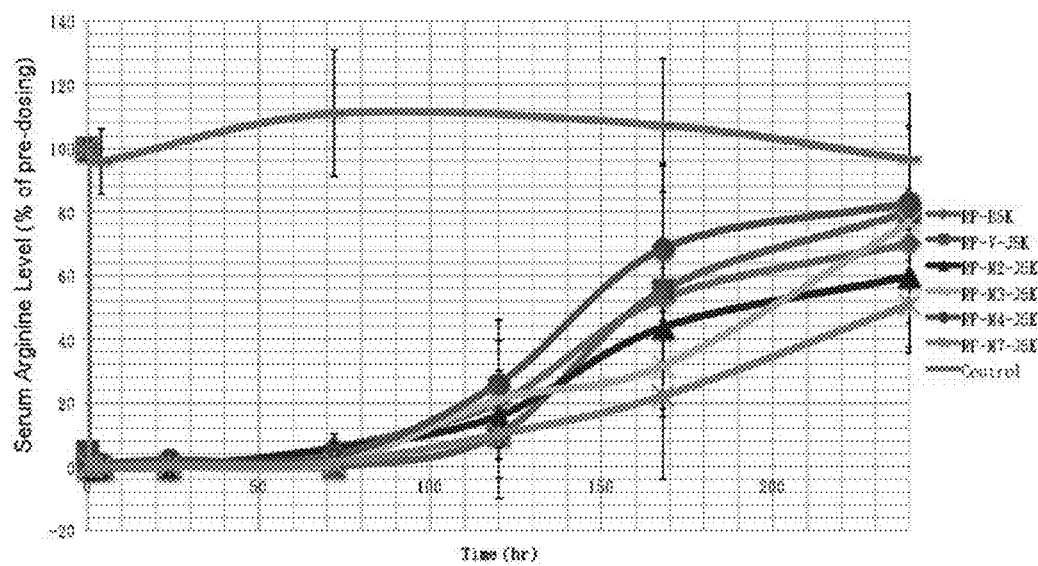
FIG. 16 is a graph illustrating the serum arginine depletion with various purified recombinant human Arginase(s) pegylated on Lys residues.
Figure 17:
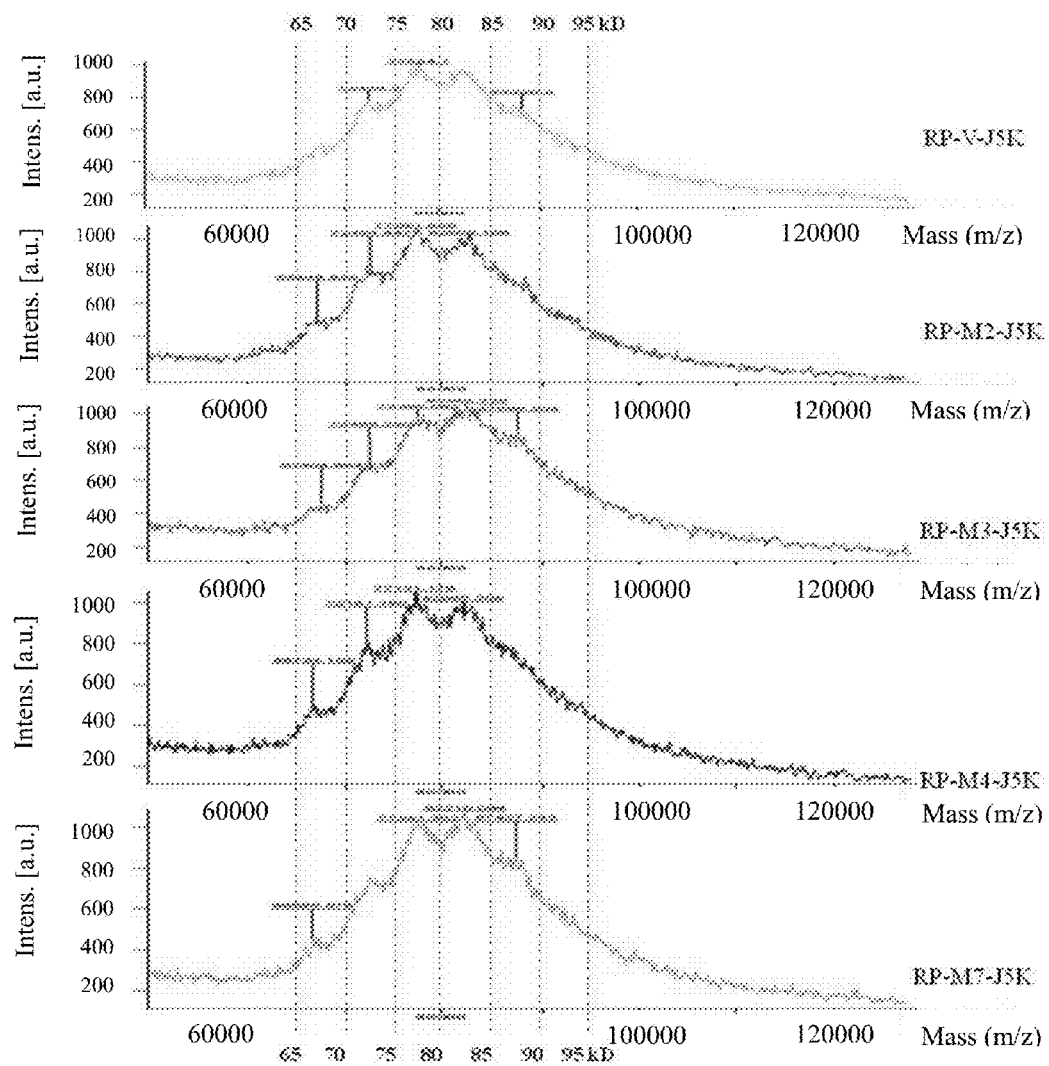
FIG. 17 is a graph illustrating the degree of pegylation of various purified recombinant human Arginase I proteins by amine ($-NH_2$) conjugation.

TABLE 7 summarizes the pegylation of various mutant recombinant human Arginases by amine (—NH$_2$) conjugation. FIG. 16 is a graph illustrating the serum arginine depletion by recombinant human Arginase I with various arginases pegylated on Lys residues. FIG. 17 is a graph illustrating the degree of pegylation of various recombinant human Arginase I proteins by amine (—NH$_2$) conjugation.

TABLE 7

| SEQ ID NO. | SPA-PEG MW | Pegylation Products | Pegylation Sites | Pegylation Ratio (MALDI-Tof) |
|---|---|---|---|---|
| SEQ ID NO: 5 | 5K | M2-5K (Lys) | Lys, NH$_2$ | 6-12 |
| SEQ ID NO: 6 | 5K | M3-5K (Lys) | Lys, NH$_2$ | 6-12 |
| SEQ ID NO: 8 | 5K | M4-5K (Lys) | Lys, NH$_2$ | 6-12 |
| SEQ ID NO: 7 | 5K | M7-5K (Lys) | Lys, NH$_2$ | 6-12 |

The half-life $T_2$, peak plasma concentration after drug administration $C_{max}$, and the integral of the concentration-time curve after administration of a single dose AUC of various amine (—NH$_2$) modified pegylated arginases in six different rats is shown in TABLE 8. Each measurement was obtained after administration of a single intravenous dose of 3 mg/kg (mean±SD; n=6). The pharmacokinetic data in rats indicates that pegylation of recombinant human Arginase I at multiple sites with low molecular weight PEGs, such as methoxy poly(ethylene glycol) succinimidyl proprionate (mPEG-SPA) can provide effective arginine depletion in vivo.

TABLE 8

| Pegylated Products | $T_{1/2}$ (hours) | $C_{max}$ (μg/mL) | $AUC_{last}$ (h * μg/mL) | $AUC_{INF}$ (h * μg/mL) |
|---|---|---|---|---|
| SEQ ID NO: 1 (pegylated with mPEG-SPA 5K) | 43.8 ± 4.4 | 42.2 ± 3.6 | 1918.7 ± 271.0 | 2687.0 ± 290.2 |
| M2-5K(Lys) | 40.7 ± 13.2 | 36.0 ± 6.0 | 1585.0 ± 184.8 | 2505.6 ± 534.8 |
| M3-5K(Lys) | 53.5 ± 14.2 | 34.4 ± 7.4 | 2675.3 ± 560.4 | 3577.4 ± 865.8 |
| M4-5K(Lys) | 59.5 ± 9.9 | 34.7 ± 8.7 | 2265.7 ± 659.8 | 3147.8 ± 673.0 |
| M7-5K(Lys) | 50.5 ± 13.0 | 56.5 ± 11.0 | 4574.6 ± 1268.2 | 4939.5 ± 1308.1 |
| SEQ ID NO: 9 (pegylated with mPEG-SPA 5K) | 35.5 ± 2.6 | 63.2 ± 5.1 | 3430.3 ± 361.5 | 3578.5 ± 415.1 |

In addition, enzyme kinetic parameters were measured for various mutant Arginases as described in TABLE 9. In sum, modification of recombinant human Arginases with small molecular weight PEGs does not result in a reduction of enzymatic activity.

TABLE 9

| Pegylated Products | $K_m$ (mM) | $V_{max}$ (μmol * mL$^{-1}$ * min$^{-1}$) | $K_{cat}$ (sec$^{-1}$) | $K_{cat}/K_m$ (mM$^{-1}$sec$^{-1}$) |
|---|---|---|---|---|
| M1-20K (45/168) | 1.76 | 0.0196 | 286.5 | 162.4 |
| M1-30K (45/168) | 1.92 | 0.0249 | 363.1 | 188.8 |
| M2-40K (45) | 1.87 | 0.0252 | 367 | 196.1 |
| M3-40K (168) | 2.07 | 0.0263 | 383.1 | 185.1 |
| M2-5K (Lys) | 2.05 | 0.0254 | 370 | 180.8 |
| M3-5K (Lys) | 2.03 | 0.0345 | 503.2 | 246.9 |
| M7-5K (Lys) | 1.79 | 0.0314 | 459.2 | 255.2 |
| SEQ ID NO: 9 | 2.12 | 0.0293 | 426.8 | 202.3 |

Figure 18:
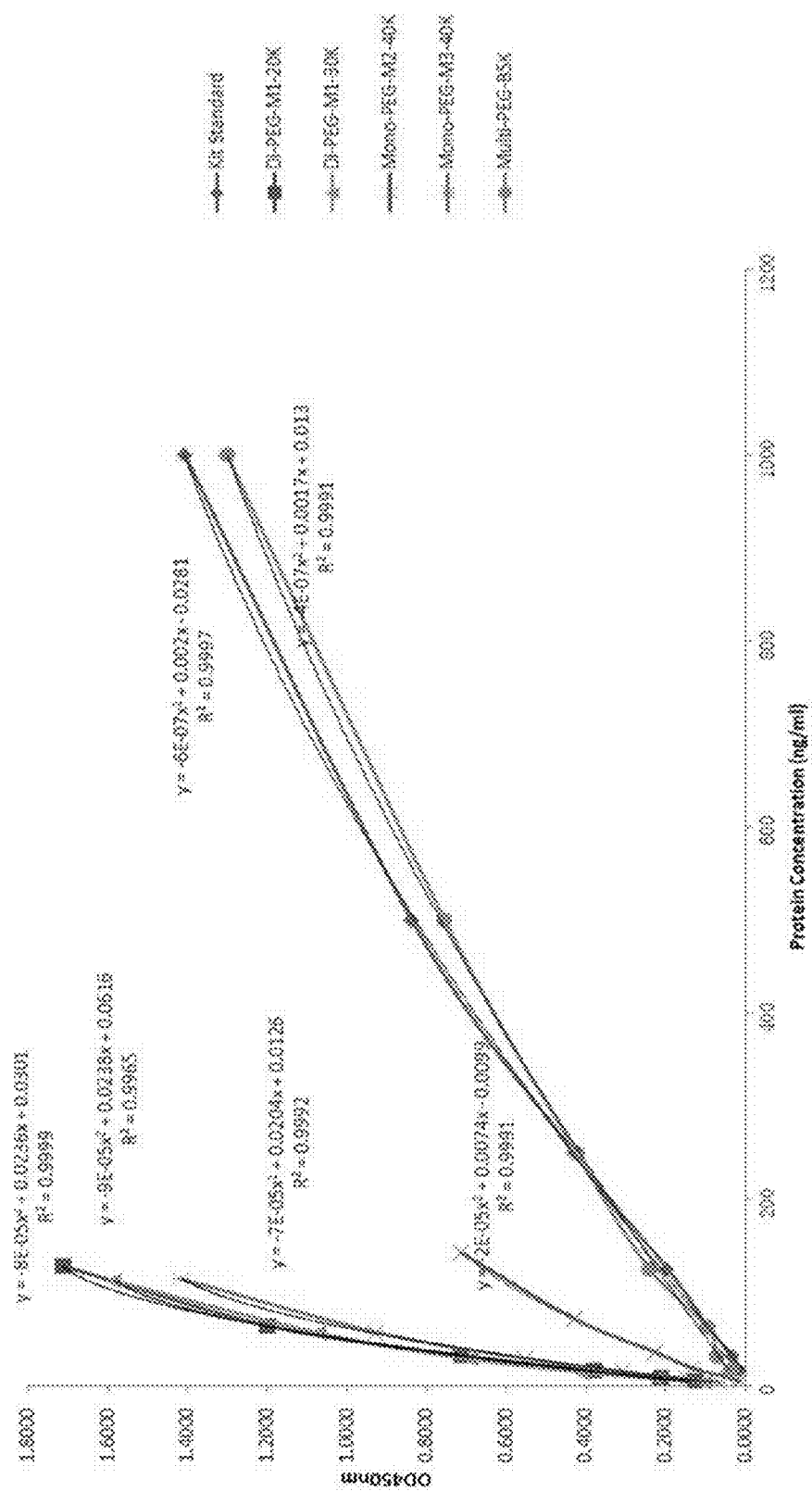
FIG. 18 is a graph illustrating the epitope analysis of a purified pegylated recombinant human Arginase I.

FIG. 18 is a graph illustrating the epitope analysis of a pegylated recombinant human Arginase I.

Example 7. Recombinant Arginase I in the Treatment of Human Autoimmune Conditions As disclosed in previous examples, Arginase I functions as an immunemodulating protein on intra- and extra-cellular levels. Pharmacological interference with arginase mediated L-arginine depletion can effectively ameliorate swelling, pain, and joint stiffness in art recognized models of Multiple Sclerosis and Rheumatoid Arthritis (Examples 4 and 5).

Rheumatoid arthritis (RA) is characterized as a chronic, inflammatory disease in which the immune system destroys synovial joints and accessory structures. Due to the progressive nature of RA, this autoimmune condition can cause extra-articular complications within several organ systems. Administration of a recombinant Arginase I of the disclosure can be used for the treatment of rheumatoid arthritis in a human.

Any one of the recombinant human Arginases disclosed in SEQ ID NOS: 1 through 16 can be used for the treatment of an autoimmune condition in a human, such as multiple sclerosis or rheumatoid arthritis. The purified Arginase can be pegylated. In some embodiments, the purified Arginase is pegylated via amine conjugation with a methoxy poly(ethylene glycol) succinimidyl proprionate (mPEG-SPA) oligomer that weighs about 5 kDa (Example 6). In other embodiments, the purified Arginase can by pegylated with any other suitable PEG oligomer.

Pegylation of the purified Arginase(s) can provide a pharmaceutical composition for the treatment of RA that has low immunogenicity, for instance, the pegylation of recombinant human Arginase I at multiple sites with low molecular weight PEGs, such as (5 kDa mPEG-SPA oligomers) effectively reduced the exposure of epitopes resulting in an effective treatment with low immunogenecity. Various PEG oligomers disclosed herein can be used to effectively reduce the exposure of epitopes of an Arginase of the disclosure.

Example 8. Recombinant Arginase I in Organ Transplantation

Immune suppression dampens an abnormal immune response in autoimmune diseases but it can also reduce a normal immune response to prevent rejection of transplanted organs or cells. Immunomodulator drugs are important in the management of organ transplantation. Any one of the recombinant human Arginases disclosed in SEQ ID NOs: 1-16 can be used as an immunomodulator in the management of organ transplantation. In some embodiments, the recombinant Arginase is pegylated. In some embodiments, the recombinant Arginase is pegylated via amine conjugation with a methoxy poly(ethylene glycol) succinimidyl proprionate (mPEG-SPA) oligomer that weighs about 5 kDa. In other embodiments, the purified Arginase can by pegylated with any other suitable PEG oligomer. Pegylation of the recombinant Arginase can provide a pharmaceutical composition for the treatment of RA that has low immunogenicity: the pegylation of recombinant human Arginase I at multiple sites with low molecular weight PEGs, such as (5 kDa mPEG-SPA oligomers) can effectively reduce the exposure of epitopes resulting in the reduction of immunogenicity. Various PEG oligomers disclosed herein can be used to effectively reduce the exposure of epitopes of an Arginase of the disclosure.

Example 9. Treatment of Experimental Autoimmune Encephalomvelitis (EAE) with Recombinant Human Arginase I The experimental autoimmune encephalomyelitis (EAE) mouse is an art recognized model of multiple sclerosis. EAE is also widely used as an animal model for T-cell-mediated autoimmune diseases.

Figure 19:
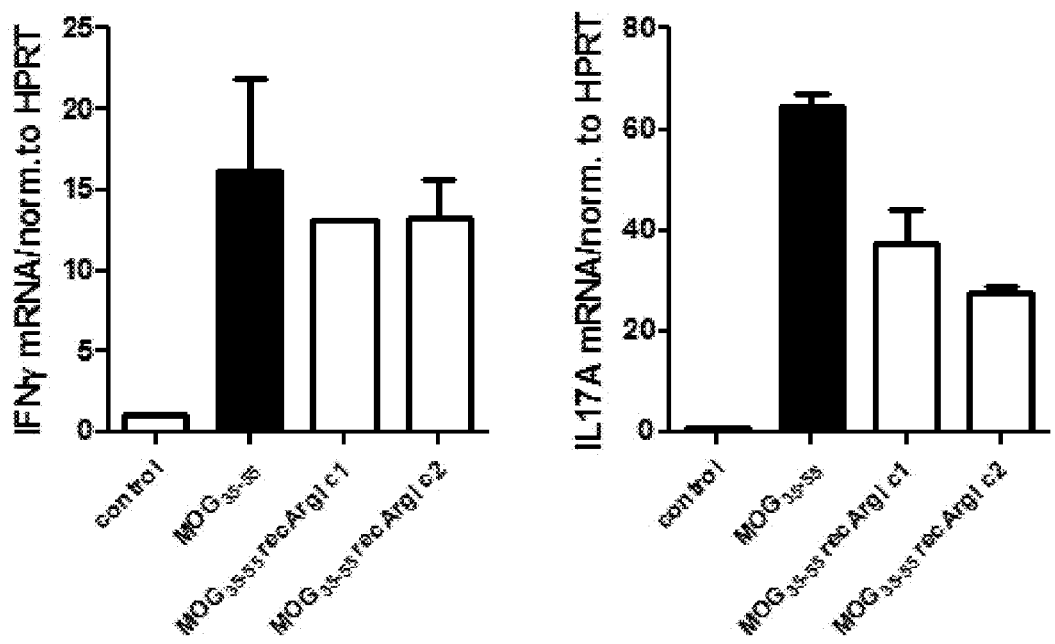
FIG. 19 illustrates IFNγ and IL-17A mRNA expression levels from myelin oligodendrocyte glycoprotein (MOG) restimulated T-cells inhibited with purified human Arginase I.
Figure 20:
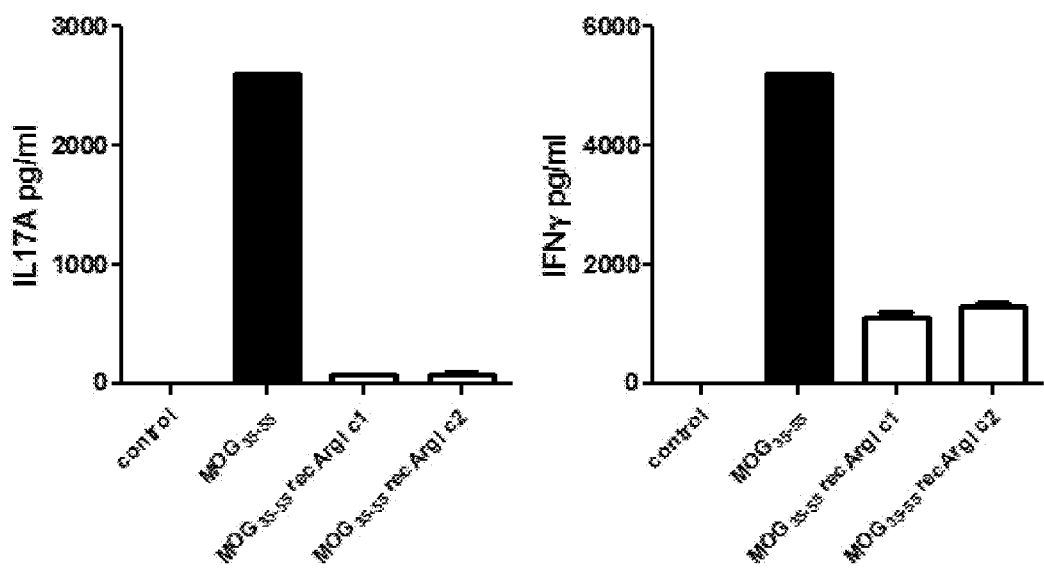
FIG. 20 illustrates IFNγ and IL-17A protein expression levels from myelin oligodendrocyte glycoprotein (MOG) restimulated T-cells inhibited with purified human Arginase I.

To investigate the effectiveness of treating an inflammatory disease in a subject with a therapeutically-effective amount of a recombinant Arginase, the effectiveness of a pegylated recombinant human Arginase I, SEQ ID NO: 9, in modulating the mRNA and protein expression of Interferon gamma and IL-17A in stimulated T-cells was investigated (treatment protocol and T-cell isolation was as described in Example 1). FIG. 19 illustrates IFNγ and IL-17A mRNA expression levels from myelin oligodendrocyte glycoprotein (MOG) restimulated Tcells inhibited with purified human Arginase I. FIG. 20 illustrates IFNγ and IL-17A protein expression levels from myelin oligodendrocyte glycoprotein (MOG) restimulated Tcells inhibited with purified human Arginase I. FIGS. 19 and 20 illustrate a significant reduction in mRNA and protein levels of IFNγ and IL-17A in MOG stimulated Tcells.

Figure 21:
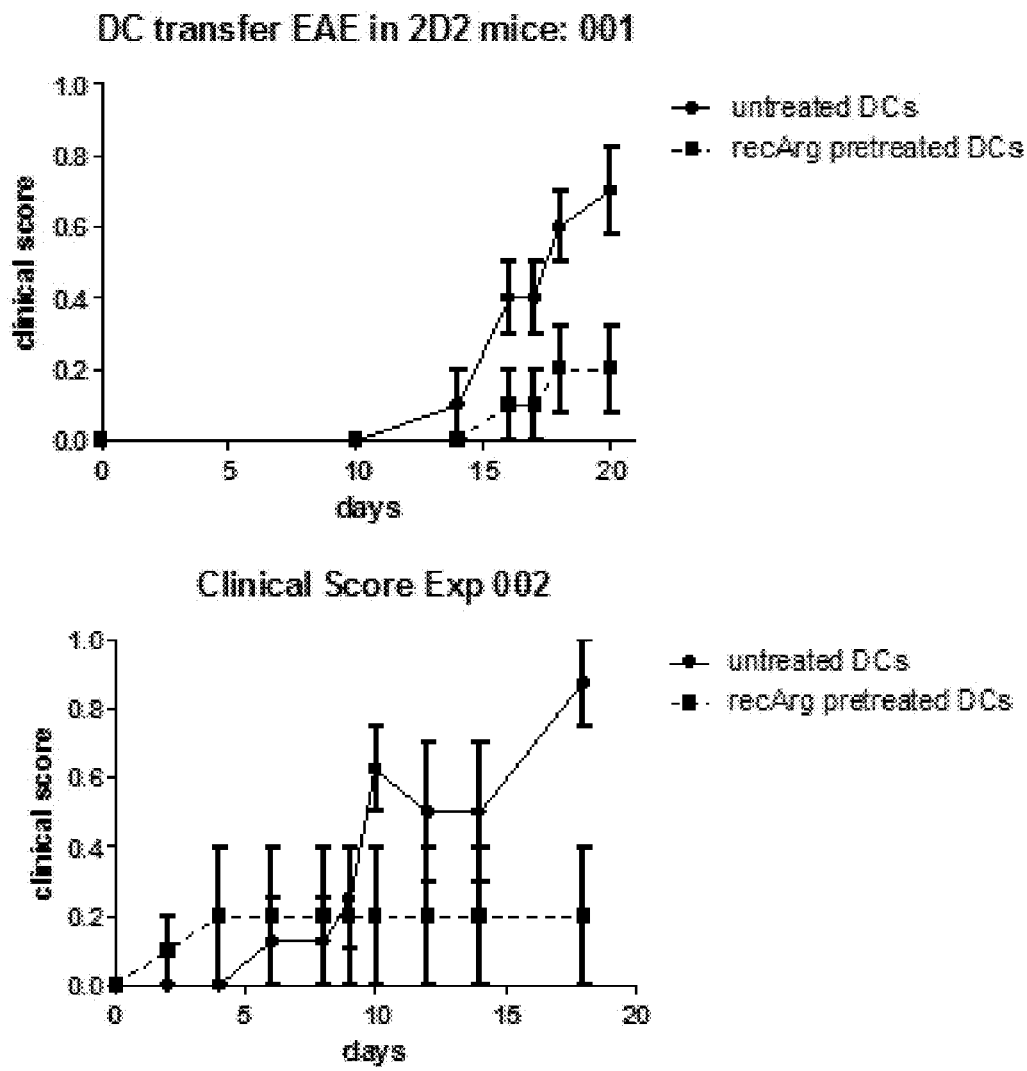
FIG. 21 illustrates improvements in clinical score of experimental autoimmune encephalomyelitis (EAE) mice treated with a recombinant human Arginase I.

FIG. 21 illustrates improvements in clinical scores of experimental autoimmune encephalomyelitis (EAE) mice treated with recombinant human Arginase I. In this experiment, antigen-presenting cells were treated with pegylated recombinant human Arginase I, SEQ ID NO: 9, ex vivo and transplanted back into EAE mice. FIG. 21, Panel A, illustrates the clinical score of EAE mice that were not challenged with CFA and pertussis prior to receiving ex vivo stimulated antigen presenting cells. FIG. 21, Panel A, illustrates a delayed improvement in the clinical score of the mice that had not been challenged with CFA and pertussis.

FIG. 21, Panel B, illustrates the clinical score of EAE mice that were challenged with CFA and pertussis prior to receiving ex vivo stimulated antigen presenting cells. FIG. 21, Panel B, illustrates a more rapid clinical score improvement.

Example 10. Modulation of Osteoclast Differentiation with Recombinant Human Arginase I In healthy bone, bone formation and bone resorption are processes involved in the normal remodeling of bone. In the process of remodeling, cells called osteoclasts resorb bone tissues whereas cells called osteoblasts deposit new bone tissue. Osteoclasts are important in the remodeling, maintenance, and repair of bones of the vertebral skeleton. For instance, osteoclast dysfunction has been associated with osteoporosis.

Figure 22:
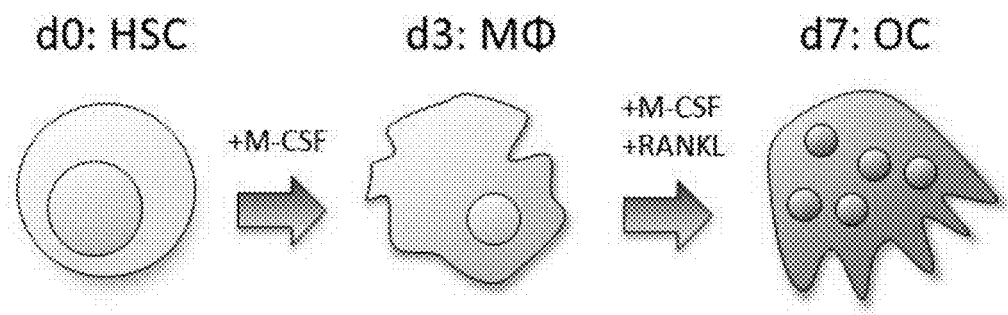
FIG. 22 is a schematic of an osteoclast differentiation assay.
Figure 23:
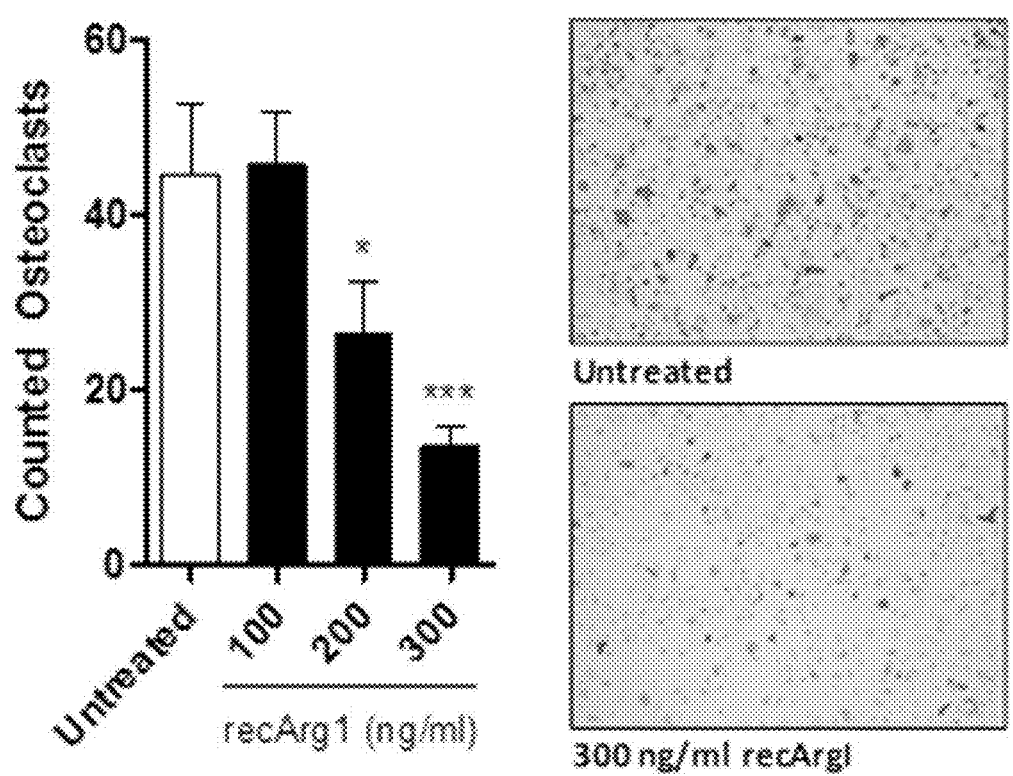
FIG. 23 is a graph illustrating an osteoclast assay of differentiated wildtype bone marrow derived macrophages treated with a recombinant human Arginase I.

An osteoclast differentiation assay was employed to assess the ability of the recombinant human Arginase disclosed in SEQ ID NO: 9 to modulate osteoclast differentiation. FIG. 22 is an schematic of an osteoclast differentiation assay. On day 0 of the differentiation assay, bone marrow cells were isolated from male mice with standard techniques, i.e., bone marrow cells were flushed with PBS from the fibia, plated in 10 cm tissue culture dishes and treated with 100 ng/ml of M-CSF. After 3 days of differentiation induced by the M-CSF, cells were harvested and plated at a density of 100,000 cells/ml. The plated cells were subsequently treated with 50 ng/ml RANKL and 30 ng/ml M-CSF. At days 7-8 of the differentiation protocol osteoclasts were TRAP-stained and counted. FIG. 23, Panel A is a graph enumerating the number of osteoclasts with at least three nuclei that were counted in an osteoclast differentiation assay. As shown in FIG. 23, Panel A, bone marrow cells were treated with recombinant Arginase I on days 3 and 6 of the differentiation protocol and together with RANKL incubation. FIG. 23, Panel B is a representative microscopy picture illustrating Tartrate-resistant acid phosphatase (TRAP) staining of cells in control dish (untreated) and cells that were treated with 300 ng/ml of the recombinant human Arginase of SEQ ID NOs: 9. The TRAP staining is a marker for osteoclasts. The data is presented as mean±SEM and n=two mice per group, and corresponds to two independent experiments. Three technical replicates were performed in each independent experiment. * represent p<0.05, *** represent p<0.001. B.

Figure 24:
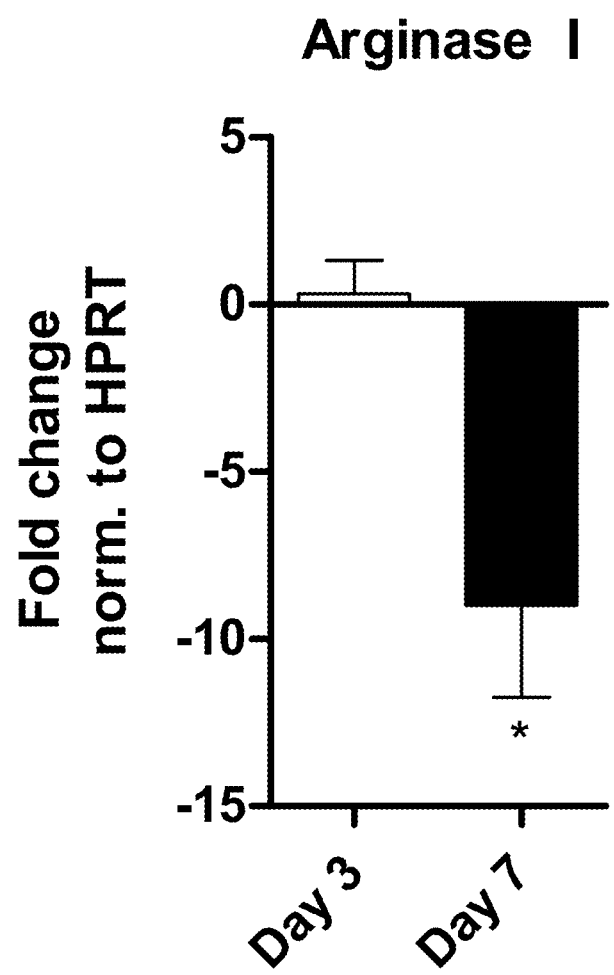
FIG. 24 is a graph demonstrating that expression of Arginase I can be lost during osteoclastogenesis.

The expression levels of endogenous Arginase I mRNA were monitored by qPCR at different time points during the differentiation protocol. FIG. 24 is a graph illustrating the expression levels of Arginase I in control cells on days 3 and 7 of the differentiation protocol as compared to the levels of the housekeeping control gene HPRT. The sequence of the Arginase primers used is disclosed in TABLE 3. FIG. 24 illustrates that expression of Arginase I is lost during osteoclastogenesis. Messenger RNA levels of Arginase I decrease after addition of RANKL on day 3 of osteoclast differentiation. The data of FIG. 24 is presented as mean±SEM and n=5 mice per group, and are two combined independent experiments. * Represents p<0.05.

Figure 25:
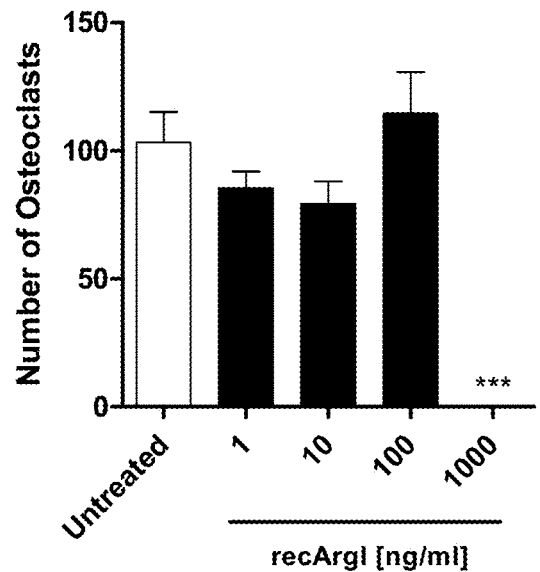
FIG. 25 illustrates that addition of recombinant Arginase I during osteoclast differentiation can modulate osteoclast formation.
Figure 25:
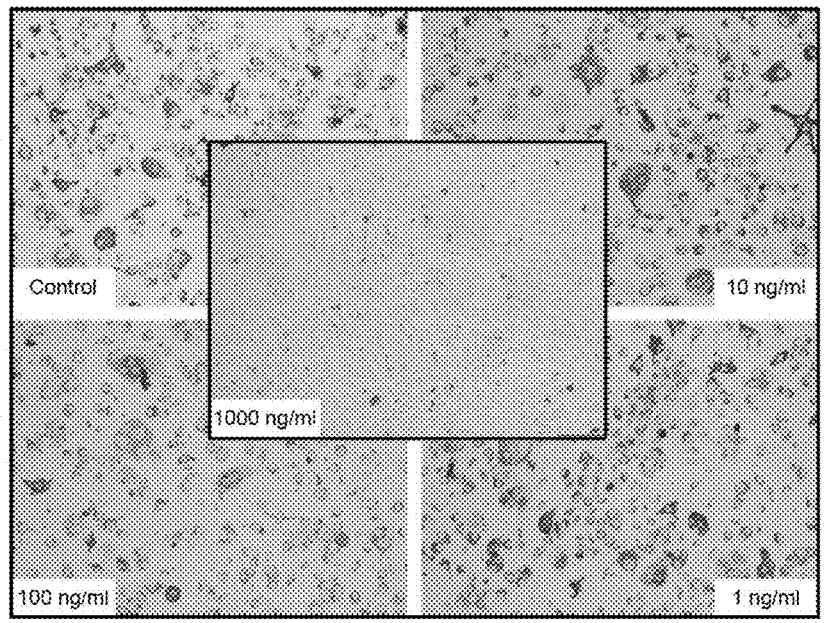

To assess the ability of recombinant Arginase I to modulate osteoclast differentiation, increasing dosages of the recombinant human Arginase of SEQ ID NOs: 9 were added to different petri dishes on days 3 and day 6 of the differentiation protocol. The experimental protocol used is as follows (a minimum of three different petri dishes received each treatment): a) a control dish was not treated with recombinant human Arginase; b) a first experimental dish was treated with a dose of 1 ng/ml of the recombinant human Arginase on days 3 and day 6 of the differentiation protocol; c) a second experimental dish was treated with a dose of 10 ng/ml of the recombinant human Arginase on days 3 and day 6 of the differentiation protocol; d) a third experimental dish was treated with a dose of 100 ng/ml of the recombinant human Arginase on days 3 and day 6 of the differentiation protocol; e) a fifth experimental dish was treated with a dose of 1,000 ng/ml (1 µg/ml) of the recombinant human Arginase on days 3 and day 6 of the differentiation protocol. FIG. 25 illustrates that addition of recombinant human Arginase I (SEQ ID NO. 9) during days 3 and 6 of osteoclast differentiation can modulate osteoclast formation. FIG. 25, Panel A shows that addition of 1,000 ng/ml of recombinant human Arginase I (SEQ ID NO. 9) inhibited osteoclast formation. FIG. 25, Panel B illustrates representative microscope pictures of the cells treated with the dosages of the recombinant human Arginase I (SEQ ID NO. 9) described in a)-e). A recombinant human Arginase I (SEQ ID NO. 9) can block osteoclastogenesis in a dose dependent manner at concentrations between 100 and 300 ng/ml. FIG. 25, Panel B illustrates that cells incubated with 1,000 ng/ml appear morphologically as TRAP negative macrophages despite of incubation with RANKL. The data in FIG. 25 is presented as mean±SEM and n=6 mice per group, and are three combined independent experiments, *** represents p<0.001.

Figure 26:
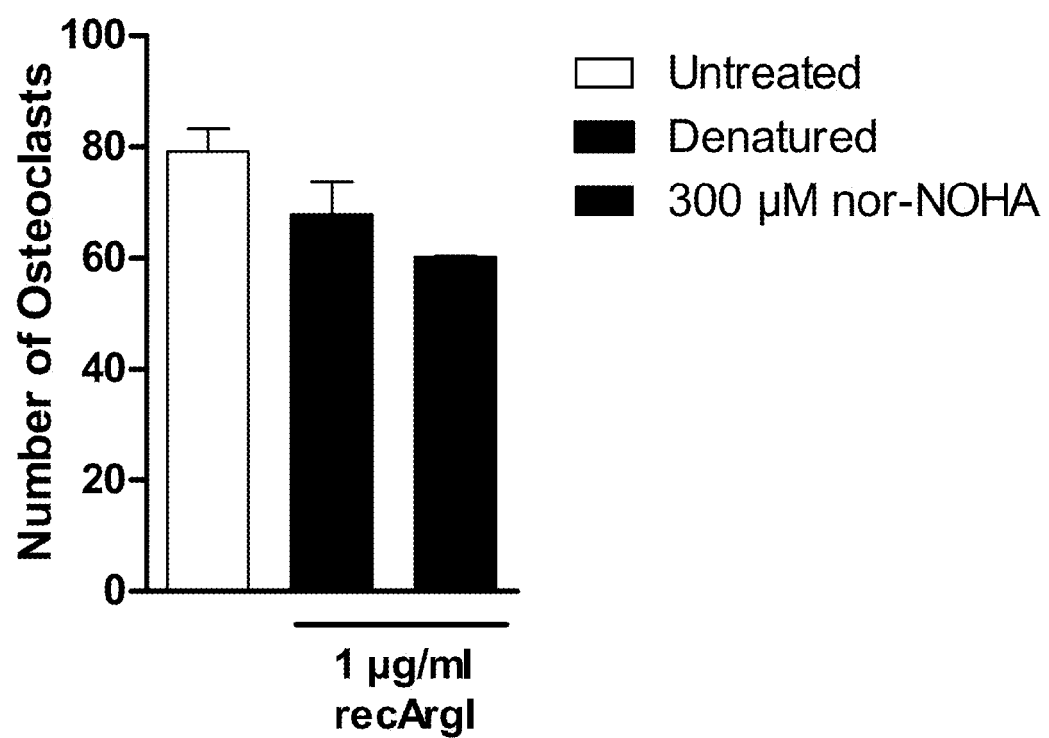
FIG. 26 is a graph illustrating that blockage of osteoclastogenesis can be dependent on the catalytic functions of recombinant human Arginase I (recArgI).

To assess the direct effects of the recombinant human Arginase I (SEQ ID NO. 9) in modulating osteoclast differentiation, the differentiation protocol described above was performed with the addition of untreated, denatured, and enzymatically inactivated recombinant human Arginase I (SEQ ID NO. 9). The assay assessed the ability of denatured and enzymatically inactivated Arginase I in promoting or inhibiting osteoclast formation. The Arginase I enzyme was either a) heat denatured (70° C. 10 min) or b) enzymatically inactivated with 300 µM of the inhibitor nor-NOHA. The Arginases were then added to separate dishes on day 3 of the differentiation protocol. FIG. 26 illustrates the number of differentiated osteoclasts that could be enumerated in a differentiation assay supplemented with denatured and N(omega)-hydroxy-nor-arginine (nor-NOHA) treated recombinant human Arginase I (SEQ ID NO. 9) as compared to a control, untreated dish. Normal osteoclast counts were observed, which suggests that Arginine availability is a prerequisite for osteoclast formation. The data in FIG. 26 is presented as mean±SEM and n=2 mice per group, and are representative of one experiment. FIG. 26 demonstrates that blockage of osteoclastogenesis is dependent on the catalytic functions of Arginase I.

Figure 27:
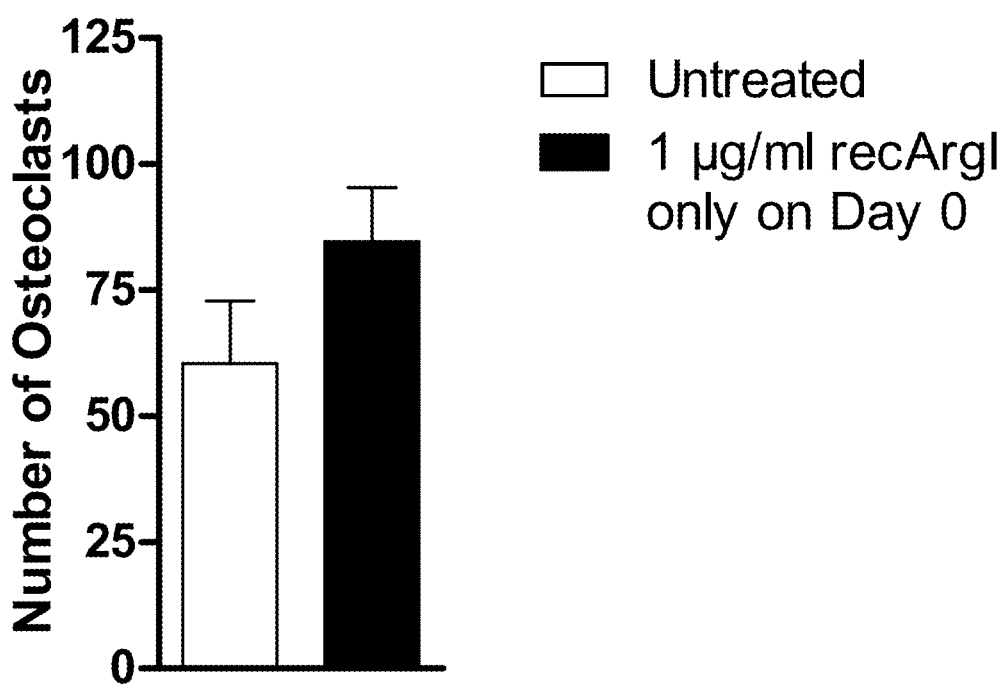
FIG. 27 is a graph illustrating an assay where addition of recombinant Arginase I to hematopoietic stem cells did not influence osteoclast formation.

Osteoclasts are formed by the fusion of many cells derived from circulating monocytes in the blood, which are derived from hematopoietic stem cells. To assess the role of Arginase I in the differentiation of hematopoietic stem cells, the differentiation protocol described above was performed with the addition of 1 µg/ml of recombinant human Arginase I on day 0. FIG. 27 demonstrates that the addition of a 1 µg/ml dosage of recombinant human Arginase I recombinant Arginase I to hematopoietic stem cells on day 0 of the differentiation protocol does not influence osteoclast formation. The data in FIG. 27 is presented as mean±SEM and n=4 mice per group. The data shows a combination of two independent experiments.

Figure 28:
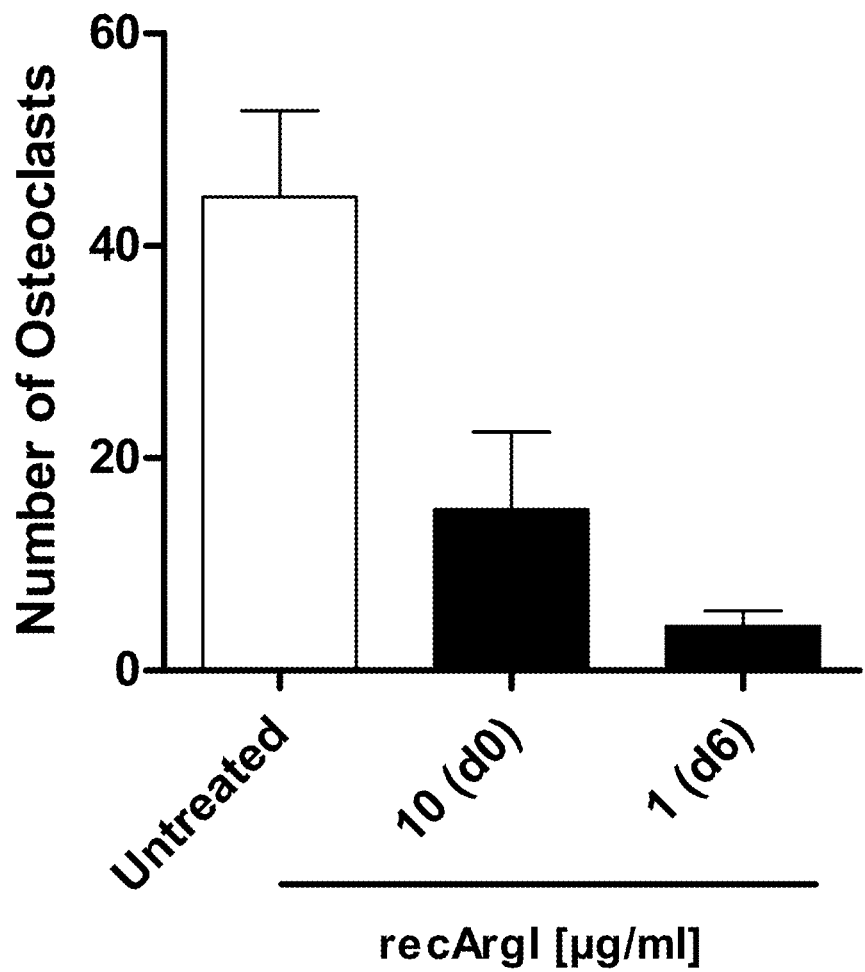
FIG. 28 is a graph illustrating the effects of different dosages of recombinant human Arginase I (recArgI) on day 0 or on day 6 osteoclastogenesis.

To assess the effects of 10 µg/ml dosages of recombinant human Arginase I in hematopoietic stem cells, the differentiation protocol described above was performed with the addition of 10 µg/ml of recombinant human Arginase I on days 0 and on day 6. FIG. 28 illustrates that addition of a 10 µg/ml dosage of recombinant human Arginase I on hematopoietic stem cells (day 0 of differentiation; "d0") can interfere with osteoclast formation. In addition, the addition of 1 µg/ml dosage of recombinant human Arginase I on cells that have been differentiated for 6 days (day 6 of differentiation; "d6") can still interfere with osteoclast formation. The data in FIG. 28 is presented as mean±SEM and n=2 mice per group, and are representative of one experiment.

Figure 29:
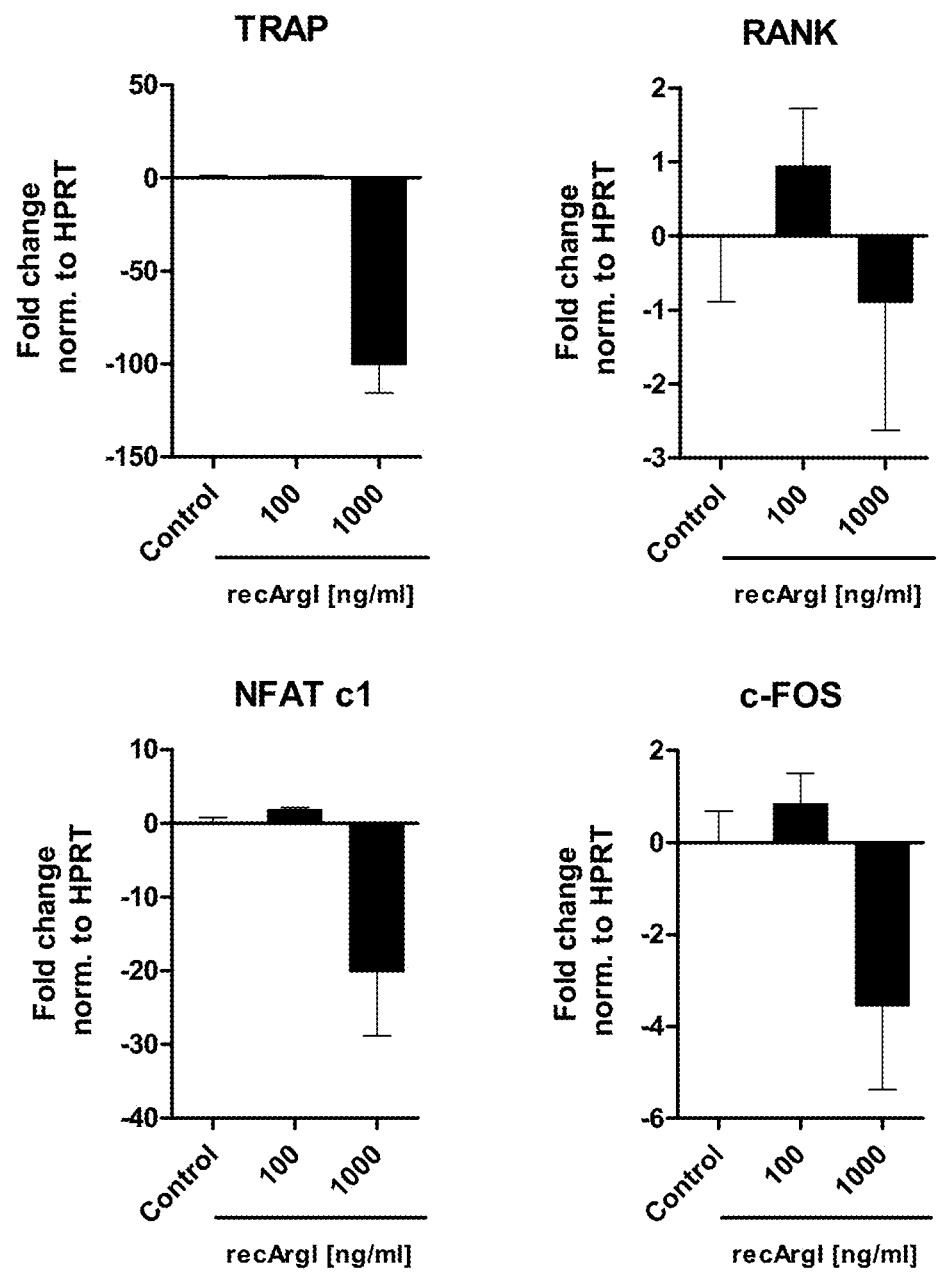
FIG. 29 is a graph illustrating the mRNA expression levels of osteoclastogenesis genes after 7 days of differentiation with and without incubation with recombinant human Arginase I (recArgI).

To assess the effects of different dosages of recombinant human Arginase I in the expression levels of genes involved in osteoclastogenesis, mRNA levels of relevant genes of osteoclastogenesis were measured after 7 days of differentiation (with and without incubation with recombinant human Arginase I). FIG. 29 illustrates the changes in expression levels of the TRAP, RANK, NFAT c1, and c-FOS genes during differentiation with and without recombinant human Arginase I. Messenger RNA levels of RANK, NFATc1 and c-FOS are increased after addition of 100 ng/ml recombinant human Arginase I, indicating a stimulating effect of lower Arginase I concentrations. Addition of 1,000 ng/ml recombinant human Arginase I correlates with a strong downregulation of the TRAP, RANK, NFAT c1, and c-FOS genes genes. The data in FIG. 29 is presented as mean±SEM and n=4 mice per group, and are two combined independent experiments.

Example 11. In-Vivo Modulation of Bone Conditions with Recombinant Human Arginase I A mouse model of osteoporosis was created by removing the ovaries of 10 week-old female mice. The procedure induced artificial menopause and bone loss in the mice and provided an in-vivo model for the study of osteoporosis. Up to 30 mg/kg of the recombinant human Arginases disclosed in SEQ ID NOs: 9 was administered to the mice twice weekly. Mice were sacrificed and evaluated at 4 weeks after the start of treatment. A histological analysis of the tibiae was performed to assess bone volume and destruction. The presence of osteoblasts and osteoclasts in this disease model were assessed using OsteoMeasure software (OsteoMetrics Inc., Atlanta).

EMBODIMENTS

Embodiment 1

A method of treating an inflammatory disease in a subject in need thereof, the method comprising administering to the subject a therapeutically-effective amount of a purified Arginase, or a functional fragment thereof.

Embodiment 2

The method of Embodiment 1, wherein the inflammatory disease is rheumatoid arthritis.

Embodiment 3

The method of Embodiment 1, wherein the inflammatory disease is multiple sclerosis.

Embodiment 4

The method of any one of Embodiments 1-3, wherein the purified Arginase is recombinant Arginase.

Embodiment 5

The method of any one of Embodiments 1-4, wherein the recombinant Arginase is pegylated.

Embodiment 6

The method of any one of Embodiments 1-5, wherein the pegylated recombinant Arginase is recombinant human Arginase I.

Embodiment 7

The method of any one of Embodiments 1-6, wherein the purified Arginase is SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

Embodiment 8

The method of any one of Embodiments 1-7, wherein the therapeutically-effective amount of the purified Arginase is from about 1 mg/Kg to about 10 mg/Kg.

Embodiment 9

The method of any one of Embodiments 1-8, wherein the therapeutically-effective amount of the purified Arginase is from about 10 mg/Kg to about 100 mg/Kg.

Embodiment 10

The method of any one of Embodiments 1-9, wherein the therapeutically-effective amount of the purified Arginase is greater than 100 mg/Kg.

Embodiment 11

The method of any one of Embodiments 1-10, wherein the purified Arginase provides an arginine plasma concentration in the subject that is lower than 120 μM.

Embodiment 12

The method of any one of Embodiments 1-11, wherein the purified Arginase provides an arginine plasma concentration in the subject that is lower than 80 μM.

Embodiment 13

The method of any one of Embodiments 1-12, wherein the purified Arginase provides an arginine plasma concentration in the subject that is lower than 10 μM.

Embodiment 14

The method of any one of Embodiments 1-13, wherein the administration is intravenous administration.

Embodiment 15

The method of any one of Embodiments 1-14, wherein the therapeutically-effective amount of a purified recombinant arginase is in a unit dosage form.

Embodiment 16

The method of any one of Embodiments 1-15, wherein the subject is a human.

Embodiment 17

The method of any one of Embodiments 1-16, wherein the Arginase is partially purified.

Embodiment 18

The method of any one of Embodiments 1-16, wherein the Arginase is substantially pure.

Embodiment 19

The method of any one of Embodiments 1-16, wherein the Arginase is at least 95% pure.

Embodiment 20

The method of Embodiment 19, wherein the Arginase is at least 99% pure.

Embodiment 21

A method of modulating inflammation, the method comprising administering to a subject a therapeutically-effective amount of a purified Arginase, or a functional fragment thereof, wherein the administration modulates the inflammation.

Embodiment 22

The method of Embodiment 21, wherein the purified Arginase is a recombinant Arginase.

Embodiment 23

The method of any one of Embodiments 21 and 22, wherein the recombinant Arginase is pegylated.

Embodiment 24

The method of any one of Embodiments 21-23, wherein the pegylated recombinant Arginase is pegylated recombinant human Arginase I.

Embodiment 25

The method of any one of Embodiments 21-24, wherein the purified Arginase inhibits T-cell polarization.

Embodiment 26

The method of any one of Embodiments 21-25, wherein the purified Arginase modulates cytokine release.

Embodiment 27

The method of any one of Embodiments 21-26, wherein the cytokine is Interleukin 6.

Embodiment 28

The method of any one of Embodiments 21-26, wherein the cytokine is Interferon gamma.

Embodiment 29

The method of any one of Embodiments 21-28, wherein the purified Arginase I comprises SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, or SEQ ID No. 16.

Embodiment 30

The method of any one of Embodiments 21-29, wherein the inflammation is associated with an autoimmune disorder.

Embodiment 31

The method of Embodiment 30, wherein the autoimmune disorder is multiple sclerosis.

Embodiment 32

The method of Embodiment 30, wherein the autoimmune disorder is rheumatoid arthritis.

Embodiment 33

The method of any one of Embodiments 21-32, wherein the administration of the purified Arginase provides a plasma level of arginine in the subject that is no greater than 10 µM.

Embodiment 34

The method of any one of Embodiments 31 or 32, wherein the therapeutically-effective amount of the purified Arginase is from about 1 mg/kg to about 10 mg/kg of the subject's body mass.

Embodiment 35

The method of any one of Embodiments 31 or 32, wherein the therapeutically-effective amount of the purified Arginase is from about 10 mg/kg to about 100 mg/kg of the subject's body mass.

Embodiment 36

The method of any one of Embodiments 31 or 32, wherein the therapeutically-effective amount of the purified Arginase is greater than 100 mg/kg of the subject's body mass.

Embodiment 37

The method of any one of Embodiments 21-36, wherein the therapeutically-effective amount of the purified Arginase is administered to the subject at least once over a period of 24 hours.

Embodiment 38

The method of any one of Embodiments 21-37, wherein the therapeutically-effective amount of the purified Arginase is administered to the subject at least once over a period of 48 hours.

Embodiment 39

The method of any one of Embodiments 21-38, wherein the therapeutically-effective amount of the purified Arginase is administered to the subject at least once over a period of 1 week.

Embodiment 40

The method of any one of Embodiments 21-39, wherein the therapeutically-effective amount of the purified Arginase is administered to the subject at least once over a period of 2 weeks.

Embodiment 41

The method of any one of Embodiments 21-40, wherein the subject is a human.

Embodiment 42

A method of modulating an immune response, the method comprising administering to a subject a therapeutically-effective amount of a purified Arginase, or a functional fragment thereof, wherein the administration modulates the immune response.

Embodiment 43

The method of Embodiment 42, wherein the purified Arginase is a recombinant Arginase.

Embodiment 44

The method of Embodiment 43, wherein the recombinant Arginase is pegylated.

Embodiment 45

The method of Embodiments 44, wherein the pegylated recombinant Arginase is pegylated recombinant human Arginase I.

Embodiment 46

The method of any one of Embodiments 42-45, wherein the purified Arginase comprises SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, or SEQ ID No. 16.

Embodiment 47

The method of any one of Embodiments 42-46, wherein the modulating the immune response suppresses the immune system of a subject

Embodiment 48

The method of Embodiment 47, wherein the suppression of the immune system of the subject facilitates a cell, a tissue, or an organ transplant into the subject.

Embodiment 49

A use of a purified recombinant arginase, or a functional fragment thereof, in the preparation of a medicament for treating an inflammatory disease in a subject.

Embodiment 50

The use of Embodiment 49, wherein the inflammatory disease is rheumatoid arthritis.

Embodiment 51

The use of Embodiment 49, wherein the inflammatory disease is multiple sclerosis.

Embodiment 52

The use of Embodiment 49, wherein the purified recombinant arginase is a pegylated recombinant human Arginase I.

Embodiment 53

The use of Embodiment 52, wherein the medicament comprises less than 1000 mg of the purified recombinant arginase.

Embodiment 54

The use of Embodiment 53, wherein the medicament comprises less than 100 mg of the purified recombinant arginase.

Embodiment 55

The use of Embodiment 54, wherein the medicament comprises less than 10 mg of the purified recombinant arginase.

Embodiment 56

The use of Embodiment 55, wherein the medicament comprises less than 1 mg of the purified recombinant arginase.

Embodiment 57

The use of Embodiment 49, wherein the medicament provides an arginine plasma concentration in the subject that is lower than 120 μM.

Embodiment 58

The use of Embodiment 49, wherein the medicament provides an arginine plasma concentration in the subject that is lower than 80 μM.

Embodiment 59

The use of Embodiment 49, wherein the medicament provides an arginine plasma concentration in the subject that is lower than 10 μM.

Embodiment 60

The use of Embodiment 49, wherein the administration is intravenous administration.

Embodiment 61

The use of Embodiment 49, wherein the subject is human.

Embodiment 62

A pharmaceutical composition comprising, a purified recombinant human Arginase I protein, or a functional fragment thereof, and at least one polyethylene glycol oligomer.

Embodiment 63

The pharmaceutical composition of Embodiment 62, wherein the pegylated recombinant human Arginase I protein comprises at least two polyethylene glycol oligomers.

Embodiment 64

The pharmaceutical composition of Embodiment 62, wherein each polyethylene glycol oligomer weighs from about 20 kilodaltons and about 40 kilodaltons.

Embodiment 65

The pharmaceutical composition of Embodiment 63, wherein the pegylated recombinant human Arginase I pro-

Embodiment 66

The pharmaceutical composition of Embodiment 62, wherein the polyethylene glycol oligomer weighs about 5 kilodaltons.

Embodiment 67

The pharmaceutical composition of Embodiment 62, wherein the polyethylene glycol oligomer is conjugated to a cysteine residue of the purified recombinant human Arginase I.

Embodiment 68

The pharmaceutical composition of Embodiment 62, wherein the polyethylene glycol oligomer is conjugated to an amine residue of the purified recombinant human Arginase I protein.

Embodiment 69

The pharmaceutical composition of Embodiment 62, wherein the polyethylene glycol oligomer is conjugated to the N-terminus of the purified recombinant human Arginase I protein.

Embodiment 70

The pharmaceutical composition of Embodiment 62, wherein the pharmaceutical composition is packaged as a kit.

Embodiment 71

A method of treating a bone disease in a subject in need thereof, the method comprising administering to the subject a therapeutically-effective amount of a purified Arginase, or a functional fragment thereof.

Embodiment 72

The method of Embodiment 71, wherein the bone disease is osteoporosis.

Embodiment 73

The method of Embodiments 71 and 72, wherein the osteoporosis is associated with an osteoclast dysfunction.

Embodiment 74

The method of any one of Embodiments 71-73, wherein the purified Arginase is recombinant Arginase.

Embodiment 75

The method of any one of Embodiments 71-74, wherein the recombinant Arginase is pegylated.

Embodiment 76

The method of any one of Embodiments 71-75, wherein the pegylated recombinant Arginase is recombinant human Arginase I.

Embodiment 77

The method of Embodiment 76, wherein the pegylated recombinant human Arginase comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

Embodiment 78

The method of any one of Embodiments 71-77, wherein the therapeutically-effective amount of the purified Arginase is from about 1 mg/Kg to about 10 mg/Kg.

Embodiment 79

The method of Embodiment 78, wherein the therapeutically-effective amount of the purified Arginase is from about 10 mg/Kg to about 100 mg/Kg.

Embodiment 80

The method of Embodiment 79, wherein the therapeutically-effective amount of the purified Arginase is greater than 100 mg/Kg.

Embodiment 81

The method of any one of Embodiments 71-79, wherein the purified Arginase provides an arginine plasma concentration in the subject that is lower than 120 µM.

Embodiment 82

The method of Embodiment 81, wherein the purified Arginase provides an arginine plasma concentration in the subject that is lower than 80 µM.

Embodiment 83

The method of Embodiment 82, wherein the purified Arginase provides an arginine plasma concentration in the subject that is lower than 10 µM.

Embodiment 84

The method of any one of Embodiments 71-83, wherein the administration is intravenous administration.

Embodiment 85

The method of any one of Embodiments 71-84, wherein the therapeutically-effective amount of a purified recombinant arginase is in a unit dosage form.

Embodiment 86

The method of any one of Embodiments 71-85, wherein the subject is a human.

Embodiment 87

The method of any one of Embodiments 71-86, wherein the Arginase is partially purified.

Embodiment 88

The method of any one of Embodiments 71-87, wherein the Arginase is substantially pure.

Embodiment 89

The method of any one of Embodiments 71-88, wherein the Arginase is at least 95% pure.

Embodiment 90

The method of Embodiment 89, wherein the Arginase is at least 99% pure.

---

What is claimed is:

1. A method of treating rheumatoid arthritis in a subject in need thereof, the method comprising administering to the subject suffering from rheumatoid arthritis a therapeutically-effective amount of a purified pegylated Arginase I or a functional fragment thereof, wherein the purified pegylated Arginase I or functional fragment thereof treats the rheumatoid arthritis by inhibiting T-cell polarization.

2. The method of claim 1, wherein the purified pegylated Arginase I is a purified pegylated recombinant Arginase I.

3. The method of claim 2, wherein the purified pegylated recombinant Arginase I is a purified pegylated recombinant human Arginase I.

4. The method of claim 1, wherein the therapeutically-effective amount of the purified pegylated Arginase I or the functional fragment thereof is from about 1 mg/Kg to about 100 mg/Kg of the subject's weight.

5. The method of claim 1, wherein the therapeutically-effective amount of the purified pegylated Arginase I or functional fragment thereof is about 10 mg/Kg.

6. The method of claim 1, wherein the purified pegylated Arginase I or the functional fragment thereof provides an arginine plasma concentration in the subject that is lower than 120 μM.

7. The method of claim 1, wherein the purified pegylated Arginase I or the functional fragment thereof provides an arginine plasma concentration in the subject that is lower than 10 μM.

8. The method of claim 1, wherein the administration is intravenous administration.

9. The method of claim 1, wherein the subject is a human.

10. The method of claim 1, wherein the purified pegylated Arginase I or the functional fragment thereof is at least 95% pure.

11. The method of claim 1, wherein the therapeutically-effective amount of the purified pegylated Arginase I or the functional fragment thereof is administered to the subject at least once over a period of 24 hours.

12. The method of claim 11, wherein the therapeutically-effective amount of the purified pegylated Arginase I or the functional fragment thereof is administered to the subject at least once over a period of 1 week.

13. The method of claim 1, wherein the purified pegylated Arginase I or the functional fragment thereof modulates cytokine release in the subject.

14. The method of claim 13, wherein the cytokine is Interleukin 6.

15. The method of claim 13, wherein the cytokine is Interferon gamma.

16. A method of treating rheumatoid arthritis in a subject in need thereof, the method comprising administering to the subject a therapeutically-effective amount of a purified pegylated Arginase I or a functional fragment thereof, wherein the purified pegylated Arginase I or the functional fragment thereof reduces a pain associated with rheumatoid arthritis in the subject.

17. The method of claim 16, wherein the purified pegylated Arginase I or the functional fragment thereof inhibits T-cell polarization.

18. The method of claim 16, wherein the pain is joint pain.

19. The method of claim 16, wherein the purified pegylated Arginase I or the functional fragment thereof reduces a swelling in the arthritic subject.

20. The method of claim 16, wherein the subject is a human.

21. A method of treating rheumatoid arthritis in a subject in need thereof, the method comprising administering to the subject a composition comprising a purified pegylated human Arginase I, wherein the purified pegylated human Arginase I comprises an amino acid sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

22. The method of claim 21, wherein the purified pegylated human Arginase I comprises the amino acid sequence of SEQ ID NO: 9.

23. The method of claim 21, wherein the purified pegylated human Arginase I comprises the amino acid sequence of SEQ ID NO: 1.

24. The method of claim 21, wherein the purified pegylated human Arginase I is pegylated via amine conjugation, cysteine (SH) conjugation, or N-terminal modification with a PEG oligomer.

25. The method of claim 24, wherein the purified pegylated human Arginase I is pegylated via amine conjugation with a PEG oligomer.

26. The method of claim 25, wherein the PEG oligomer weighs less than about 10 kDa.

27. The method of claim 25, wherein the PEG oligomer is methoxy poly(ethylene glycol) succinimidyl proprionate (mPEG-SPA).

28. The method of claim 24, wherein the purified pegylated human Arginase I has low immunogenicity.

29. The method of claim 21, wherein the purified pegylated human Arginase I is expressed from bacterial cells or insect cells.

30. The method of claim 1, wherein the rheumatoid arthritis is associated with IL-17 inflammation.

* * * * *